US009945763B1

(12) United States Patent
Tacha et al.

(10) Patent No.: US 9,945,763 B1
(45) Date of Patent: Apr. 17, 2018

(54) METHODS AND SYSTEMS FOR IMMUNOHISTOCHEMISTRY HEAT RETRIEVAL OF BIOLOGICAL SAMPLES

(75) Inventors: David Tacha, San Ramon, CA (US); Thomas Maxwell, Danville, CA (US); Evan Barker, Concord, CA (US); Hoa Nguyen, Oakley, CA (US); Ravishankar Melkote, Fremont, CA (US)

(73) Assignee: Biocare Medical, LLC, Concord, CA (US)

(*) Notice: Subject to any disclaimer, the term of this patent is extended or adjusted under 35 U.S.C. 154(b) by 582 days.

(21) Appl. No.: 13/401,653

(22) Filed: Feb. 21, 2012

Related U.S. Application Data

(60) Provisional application No. 61/444,469, filed on Feb. 18, 2011.

(51) Int. Cl.
| | | |
|---|---|---|
| *G01N 1/28* | (2006.01) | |
| *G01N 1/30* | (2006.01) | |
| *G01N 1/34* | (2006.01) | |
| G01N 1/44 | (2006.01) | |
| G01N 33/53 | (2006.01) | |
| G01N 35/00 | (2006.01) | |

(52) U.S. Cl.
CPC .............. *G01N 1/30* (2013.01); *G01N 1/34* (2013.01); *G01N 1/44* (2013.01); *G01N 33/53* (2013.01); *G01N 2035/0091* (2013.01)

(58) Field of Classification Search
CPC ............ G01N 1/30; G01N 1/31; G01N 1/312; G01N 1/44; G01N 33/53; G01N 33/5306; A47J 27/0802; A47J 27/08; A47J 27/086; A47J 27/088; A47J 27/09; A47J 27/092
See application file for complete search history.

(56) References Cited

U.S. PATENT DOCUMENTS

| | | | |
|---|---|---|---|
| 4,146,414 | A | 3/1979 | Stomby |
| 4,341,736 | A | 7/1982 | Drbal et al. |
| 4,436,822 | A | 3/1984 | Eseifan |
| 4,569,758 | A | 2/1986 | Sandulyak et al. |
| 4,635,791 | A | 1/1987 | Jackson et al. |
| 4,949,069 | A | 8/1990 | Wilson |
| 5,023,187 | A | 6/1991 | Koebler et al. |
| 5,024,933 | A | 6/1991 | Yang et al. |
| 5,124,203 | A | 6/1992 | Leatherman |
| 5,232,664 | A | 8/1993 | Krawak et al. |
| 5,246,665 | A | 9/1993 | Tyranski et al. |
| 5,308,460 | A | 5/1994 | Mazid et al. |
| 5,319,974 | A | 6/1994 | Lenz et al. |
| 5,344,637 | A | 9/1994 | Camiener |
| 5,425,918 | A | 6/1995 | Healey et al. |
| 5,439,649 | A | 8/1995 | Tseung et al. |
| 5,444,218 | A | 8/1995 | Zelniker et al. |
| 5,567,458 | A | 10/1996 | Wu |
| 5,595,707 | A | 1/1997 | Copeland et al. |
| 5,645,114 | A | 7/1997 | Bogen et al. |
| 5,650,327 | A | 7/1997 | Copeland et al. |
| 5,654,199 | A | 8/1997 | Copeland et al. |
| 5,654,200 | A | 8/1997 | Copeland et al. |
| 5,839,091 | A | 11/1998 | Rhett et al. |
| 5,842,353 | A | 12/1998 | Kuo-Liang |
| 5,947,167 | A | 9/1999 | Bogen et al. |
| 5,948,359 | A | 9/1999 | Kalra et al. |
| 5,985,669 | A | 11/1999 | Palander et al. |
| 6,045,759 | A | 4/2000 | Ford et al. |
| 6,093,574 | A | 7/2000 | Druyor-Sanchex et al. |
| 6,096,271 | A | 8/2000 | Bogen et al. |
| 6,173,643 | B1 | 1/2001 | Qian |
| 6,192,945 | B1 | 2/2001 | Ford et al. |
| 6,283,014 | B1 | 9/2001 | Ng et al. |
| 6,296,809 | B1 | 10/2001 | Richards et al. |
| 6,303,323 | B1 | 10/2001 | Laskey et al. |
| 6,349,264 | B1 | 2/2002 | Rhett et al. |
| 6,352,861 | B1 | 3/2002 | Copeland et al. |
| 6,358,473 | B1 | 3/2002 | Coello et al. |
| 6,391,624 | B1 | 5/2002 | Megerle |
| 6,451,551 | B1 | 9/2002 | Zhan et al. |
| 6,489,167 | B1 | 12/2002 | Morgan et al. |
| 6,495,106 | B1 | 12/2002 | Kalra et al. |
| 6,534,008 | B1 | 3/2003 | Angros et al. |
| 6,537,818 | B2 | 3/2003 | Richards et al. |
| 6,541,261 | B1 | 4/2003 | Bogen et al. |

(Continued)

FOREIGN PATENT DOCUMENTS

| | | |
|---|---|---|
| CA | 2851101 | 2/2017 |
| WO | 9739328 A1 | 10/1997 |

(Continued)

OTHER PUBLICATIONS

Canfora, G. et al. "Remotely accessible laboratory for electronic measurement teaching." Computer Standards and Interfaces (2004) 26 489-499.*

Taylor, Clive R. et al. "Comparative study of antigen retrieval heating methods: Microwave, microwave and pressure cooker, autoclave, and steamer." Biotechnic and Histochemistry (1996) 71 263-270.*

Nikolov, Georgi Todorov et al. "Data logging system for pressure monitoring." Electronics (2005).*

Leong, Anthony S.-Y. et al. "Superheating antigen retrieval." Applied Immunohistochemistry and Molecular Morphology (2002) 10 263-268.*

Pyle, D. L. "Chapter 7. Process control." Chemical Engineering for the Food Industry. Blackie A & P, 1997. Edited by P.J. Fryer et al.*

(Continued)

*Primary Examiner* — Christopher Adam Hixson
(74) *Attorney, Agent, or Firm* — Santangelo Law Offices, PC

(57) ABSTRACT

Heat induced antigen retrieval systems for biological specimens may include a sealable heating pressure chamber, a programmable process controller, a nonpareil operating element, and perhaps even a substantially user-disencumbering autonomous processing component of a plurality of biological samples perhaps using various user selected protocols, and the like.

15 Claims, 54 Drawing Sheets

(56) References Cited

U.S. PATENT DOCUMENTS

| | | |
|---|---|---|
| 6,554,798 B1 | 4/2003 | Christensen et al. |
| 6,580,056 B1 | 6/2003 | Tacha |
| 6,582,921 B2 | 6/2003 | Mirkin et al. |
| 6,582,962 B1 | 6/2003 | Richards et al. |
| 6,598,474 B2 | 7/2003 | Purpura et al. |
| 6,632,598 B1 | 10/2003 | Zhang et al. |
| 6,635,225 B1 | 10/2003 | Thiem et al. |
| 6,649,368 B1 | 11/2003 | Aghassi et al. |
| 6,735,531 B2 | 5/2004 | Rhett et al. |
| 6,746,851 B1 | 6/2004 | Tseung et al. |
| 6,783,733 B2 | 8/2004 | Bogen et al. |
| 6,800,249 B2 | 10/2004 | De la Torre-Bueno |
| 6,827,901 B2 | 12/2004 | Copeland et al. |
| 6,855,292 B2 | 2/2005 | Angros |
| 6,855,552 B2 | 2/2005 | Towne et al. |
| 6,855,559 B1 | 2/2005 | Christensen |
| 6,866,881 B2 | 3/2005 | Prentice et al. |
| 6,903,207 B2 | 6/2005 | Mirkin et al. |
| 6,943,029 B2 | 9/2005 | Copeland et al. |
| 6,995,020 B2 | 2/2006 | Capodieci et al. |
| 6,998,270 B2 | 2/2006 | Tseung et al. |
| 7,025,937 B2 | 4/2006 | Plank |
| 7,067,325 B2 | 6/2006 | Christensen et al. |
| 7,070,951 B2 | 7/2006 | Zhang et al. |
| 7,074,175 B2 | 7/2006 | Hany et al. |
| 7,115,386 B2 | 10/2006 | Posthuma |
| 7,118,918 B2 | 10/2006 | Copeland et al. |
| 7,198,752 B2 | 4/2007 | Thiem |
| 7,217,392 B2 | 5/2007 | Bogen et al. |
| 7,226,788 B2 | 6/2007 | De la Torre-Bueno |
| 7,250,301 B2 | 7/2007 | Angros |
| 7,287,388 B2 | 10/2007 | Dorenkamp et al. |
| 7,300,452 B2 | 11/2007 | Gleich et al. |
| 7,303,725 B2 | 12/2007 | Reinhardt et al. |
| 7,303,729 B2 | 12/2007 | Plank |
| 7,318,913 B2 | 1/2008 | Loeffler et al. |
| 7,351,194 B2 | 4/2008 | Gleich |
| 7,359,536 B2 | 4/2008 | Hays et al. |
| 7,400,983 B2 | 7/2008 | Feingold et al. |
| 7,410,753 B2 | 8/2008 | Hopkins et al. |
| 7,435,383 B2 | 10/2008 | Tseung et al. |
| 7,468,161 B2 | 12/2008 | Reinhardt et al. |
| 7,470,541 B2 | 12/2008 | Copeland et al. |
| 7,476,362 B2 | 1/2009 | Angros et al. |
| 7,481,980 B2 | 1/2009 | Gausepohl |
| 7,494,823 B2 | 2/2009 | Sukumar |
| 7,501,283 B2 | 3/2009 | Hersch et al. |
| 7,510,555 B2 | 3/2009 | Kanzuis |
| 7,550,298 B2 | 6/2009 | Towne et al. |
| 7,553,672 B2 | 6/2009 | Bogen et al. |
| 7,584,019 B2 | 9/2009 | Feingold et al. |
| 7,585,964 B2 | 9/2009 | Palanisamy et al. |
| 7,593,787 B2 | 9/2009 | Feingold et al. |
| 7,603,201 B2 | 10/2009 | Feingold et al. |
| 7,615,371 B2 | 11/2009 | Kram |
| 7,618,807 B2 | 11/2009 | Lemme et al. |
| 7,622,077 B2 | 11/2009 | Angros et al. |
| 7,627,381 B2 | 12/2009 | Kanzius et al. |
| 7,632,461 B2 | 12/2009 | Angros |
| 7,648,678 B2 | 1/2010 | Favuzzi et al. |
| 7,718,435 B1 | 5/2010 | Bogen et al. |
| 7,722,811 B2 | 5/2010 | Konrad et al. |
| 7,744,817 B2 | 6/2010 | Bui |
| 7,758,809 B2 | 7/2010 | Favuzzi et al. |
| 7,767,152 B2 | 8/2010 | Stead et al. |
| 7,820,381 B2 | 10/2010 | Lemme et al. |
| 7,838,283 B2 | 11/2010 | Erickson et al. |
| 7,850,912 B2 | 12/2010 | Favuzzi et al. |
| 7,867,443 B2 | 1/2011 | Key et al. |
| 7,872,213 B2 | 1/2011 | DeLeon et al. |
| 7,875,242 B2 | 1/2011 | Shah |
| 7,875,245 B2 | 1/2011 | Favuzzi et al. |
| 7,897,106 B2 | 3/2011 | Angros et al. |
| 7,901,941 B2 | 3/2011 | Tseung et al. |
| 7,935,534 B2 | 5/2011 | Lemme et al. |
| 7,937,228 B2 | 5/2011 | Feingold et al. |
| 7,951,612 B2 | 5/2011 | Angros et al. |
| 7,960,178 B2 | 6/2011 | Key et al. |
| 8,062,897 B2 | 11/2011 | Capodieci et al. |
| 8,501,434 B2 | 8/2013 | Barker et al. |
| 8,765,476 B2 | 7/2014 | Avantsa et al. |
| 9,442,049 B2 | 9/2016 | Barker et al. |
| 2002/0072122 A1 | 6/2002 | Copeland et al. |
| 2003/0092029 A1 | 5/2003 | Josephson et al. |
| 2003/0124729 A1 | 7/2003 | Christensen et al. |
| 2003/0175852 A1 | 9/2003 | Kalra et al. |
| 2004/0009098 A1 | 1/2004 | Torre-Bueno |
| 2004/0033163 A1 | 2/2004 | Tseung et al. |
| 2004/0058328 A1 | 3/2004 | Chan et al. |
| 2004/0266015 A1 | 12/2004 | Favuzzi et al. |
| 2005/0164374 A1 | 7/2005 | Kram |
| 2006/0019302 A1 | 1/2006 | Lemme et al. |
| 2006/0088928 A1 | 4/2006 | Sweet et al. |
| 2006/0134793 A1 | 6/2006 | Key et al. |
| 2006/0148063 A1 | 6/2006 | Favuzzi et al. |
| 2006/0153436 A1 | 7/2006 | Haras |
| 2006/0153736 A1 | 7/2006 | Kalra et al. |
| 2006/0246524 A1 | 11/2006 | Bauer et al. |
| 2006/0265133 A1 | 11/2006 | Cocks et al. |
| 2006/0281116 A1 | 12/2006 | Angros et al. |
| 2007/0048770 A1 | 3/2007 | Jackel et al. |
| 2007/0196909 A1 | 8/2007 | Showalter et al. |
| 2007/0231889 A1 | 10/2007 | Angros et al. |
| 2008/0038836 A1 | 2/2008 | Reinhardt et al. |
| 2008/0102006 A1 | 5/2008 | Kram et al. |
| 2008/0176769 A1 | 7/2008 | Rank et al. |
| 2008/0194034 A1 | 8/2008 | Erickson et al. |
| 2008/0213804 A1 | 9/2008 | Erickson et al. |
| 2008/0318305 A1 | 12/2008 | Angros |
| 2009/0004691 A1 | 1/2009 | Erickson et al. |
| 2009/0029392 A1 | 1/2009 | Josephson et al. |
| 2009/0069335 A1 | 3/2009 | Ji et al. |
| 2009/0090855 A1 | 4/2009 | Kobold et al. |
| 2009/0181398 A1 | 7/2009 | Bauer et al. |
| 2009/0258362 A1 | 10/2009 | Brees et al. |
| 2009/0263857 A1 | 10/2009 | Gourevitch |
| 2009/0272730 A1* | 11/2009 | Friel et al. ............... 219/439 |
| 2010/0003189 A1 | 1/2010 | Tlsty et al. |
| 2010/0009429 A1 | 1/2010 | Angros |
| 2010/0028978 A1 | 2/2010 | Angros |
| 2010/0068096 A1 | 3/2010 | Angros |
| 2010/0068102 A1 | 3/2010 | Angros |
| 2010/0136613 A1* | 6/2010 | O'Leary ............... A01N 1/0231 435/40.52 |
| 2010/0164489 A1 | 7/2010 | Lukaszew et al. |
| 2011/0150725 A1 | 6/2011 | Angros et al. |
| 2011/0151504 A1 | 6/2011 | Avantsa et al. |
| 2013/0309688 A1 | 11/2013 | Barker et al. |

FOREIGN PATENT DOCUMENTS

| | | |
|---|---|---|
| WO | 2004059287 A2 | 7/2004 |
| WO | 2005024385 A2 | 3/2005 |
| WO | 2010074915 A2 | 7/2010 |
| WO | 2010078476 A1 | 7/2010 |
| WO | 2011060387 A1 | 5/2011 |
| WO | 2012048154 A1 | 4/2012 |

OTHER PUBLICATIONS

Quenby, S. M. et al. "Oncogenes and tumour suppressor genes in first trimester human fetal gonadal development." Molecular Human Reproduction (1999) 5 737-741.*

Travis, J. W. et al. "Development, implementation, and adoption of expert systems in plant pathology." Annual Reviews of Phytopathology (1991) 29 343-360.*

Elliot, Chance et al. "National Instruments LabVIEW: a programming environment for laboratory automation and measurement." J. of the Association for Laboratory Automation (2007) 12 17-24.*

Leica TP 1020 Automatic Tissue Processor Instruction Manual. Dec. 2000.*

(56) References Cited

OTHER PUBLICATIONS

BioCare Medical, 904-003 Decloaking Chamber™ Plus Manual, at least as early as Feb. 18, 2011.
BioCare Medical, DC2002 Digital Decloaking Chamber Operation Handbook, at least as early as Feb. 18, 2011.
http://www.emsdiasum.com/microscopy/products/histology/retriever.aspx; Electron Microscopy Sciences Technical Data Sheet; 4 pages.
U.S. Appl. No. 61/444,469, filed Feb. 18, 2011.
Biocare Medical LLC, IntelliPath Automated Slide Stainer Brochure, Oct. 21, 2007, 3 pages.
Aveyard, R., et al. Capillary condensation of vapours between two solid surfaces: effects of line tension and surface forces; Surfactant Science Group, Department of Chemistry, University of Hull, Hull UK; Phys. Chem. Chem. Phys, 1999, 1, 155-163.
Bouaidat, S. et al. Surface-directed capillary sytsem; theory, experiments and applicants; The Royal Society of Chemistry 2005, Lap Chip, 2005, 5, 827-836.
Finn, R. Capillary Surface Interfaces, Notices of the AMS; vol. 46, No. 7, pp. 770-781, Aug. 1999.
Bhushan, B. et al., Adhesion and stiction: Mechanisms, measurement techniques, and methods for reduction; J. Vac. Sol. Technol. B 21(6). Nov./Dec. 2003.
Wang, L, et al. Capillary Forces between Submillimeter Spheres and Flat Surfaces at Constant Liquid Volumes; Chin. Phys. Lett. vol. 26, No. 12 (2009).
Montero, C. The Antigen-Antibody Reaction in Immunohistochemistry; The Journal of Histochemistry & Cytochemistry; vol. 51(1); 1-4, 2003.
Hiratsuka, K. et al. Water droplet lubrication between hydrophilic and hydrophobic surfaces; IOP Science; 2007 J. Phys.: Conf. Ser. 89 (2007) 012012.
Potteli, K. K. Cancer Detection using Nanoparticles; ECG653 Project Report; Fall 2008.
Perez-Madrid, A. et al., Brownian Motion in the Presence of a Temperature Gradient, arXiv:cond-mat19505137v1, submitted on May 26, 1995.

Hocking, L.M. et al.; The Spreading of a Drop by Capillary Action, J. Fluid Mech. (1982) vol. 121, pp. 425-442.
Fowler, Michael; "Viscosity, Introduction: Friction at the Moledular Level", Uva. Jun. 26, 2007, 15 Pages.
Aculon SAMP Technology for Best in Class Surface Treatments, 2 Pages (date unknown).
Abstracts from Session 3A of the 79th ACS Colloid and Surface Science Symposium Jun. 12-15, 2005, https://www.clarkson.edu/camp/acs/general.htm,last update May 30, 2005 (17 pages).
Tacha et al. History and Overview of Antigen Retrieval: Methodologies and Critical Aspects. The Journal of Histotechnology, vol. 25, No. 4, Dec. 2002. 6 pages.
15 Biocare Medical Presents Decloaking Chamber Pro. The complete system for heat retrieval, quality control, CAP and JCOH laboratory inspection. Biocare Medical. 2 pages. (date unknown).
18 Decloaking Chamber Pro, Digital Programmable Pressure Cooker for HIER from Biocare Medical. Jul. 27, 2006. 1 page.
Electron Microscopy Sciences, The Retriever for Formalin-fixed, Paraffin Embedded Tissues. http://www.emsdiasum.com/microscopy/products/histology/retrieverasp. Feb. 14, 2012. 4 pages.
Taylor, et al. Comparative Study of Antigen Retrieval Heating Methods: Microwave, Microwave and Pressue Cooker, Autoclave, and Steamer. Department of Pathology, University of Southern California School of Medicine, Los Angeles. vol. 71, No. 5. Copyright 1996. 8 pages.
22 Operation Instructions for the Next Generation Decloaking Chamber (Digital Pressure Cooker with QC Program). Mar. 31, 2001. 11 pages.
16 Digital Decloaking Chamber | Operation Handbook. Biocare Medical. Aug. 10, 2007.20 pages—this was previously cited as 2011!.
17 Digital Decloaking Chamber Manual. Pressure system for heat-induced epitope retrieval. Biocare Medical. Nov. 2009. 25 pages.
Chinese Patent Application No. 201180050858.8 Notice of Allowance dated Jul. 5, 2016. 3 pages.
European Application No. 11831630.6; filed May 6, 2011 Office Action dated Jul. 13, 2016, 6 pages.

\* cited by examiner

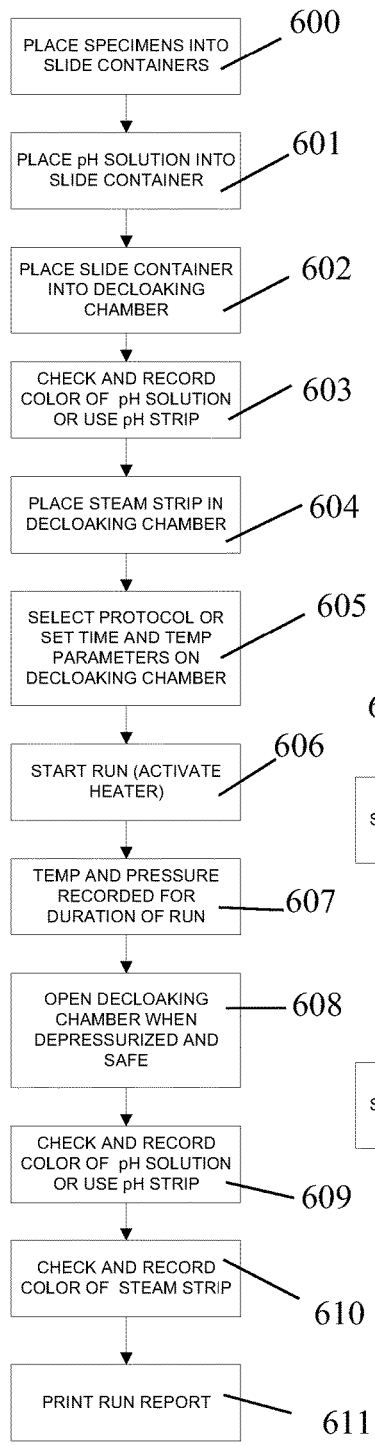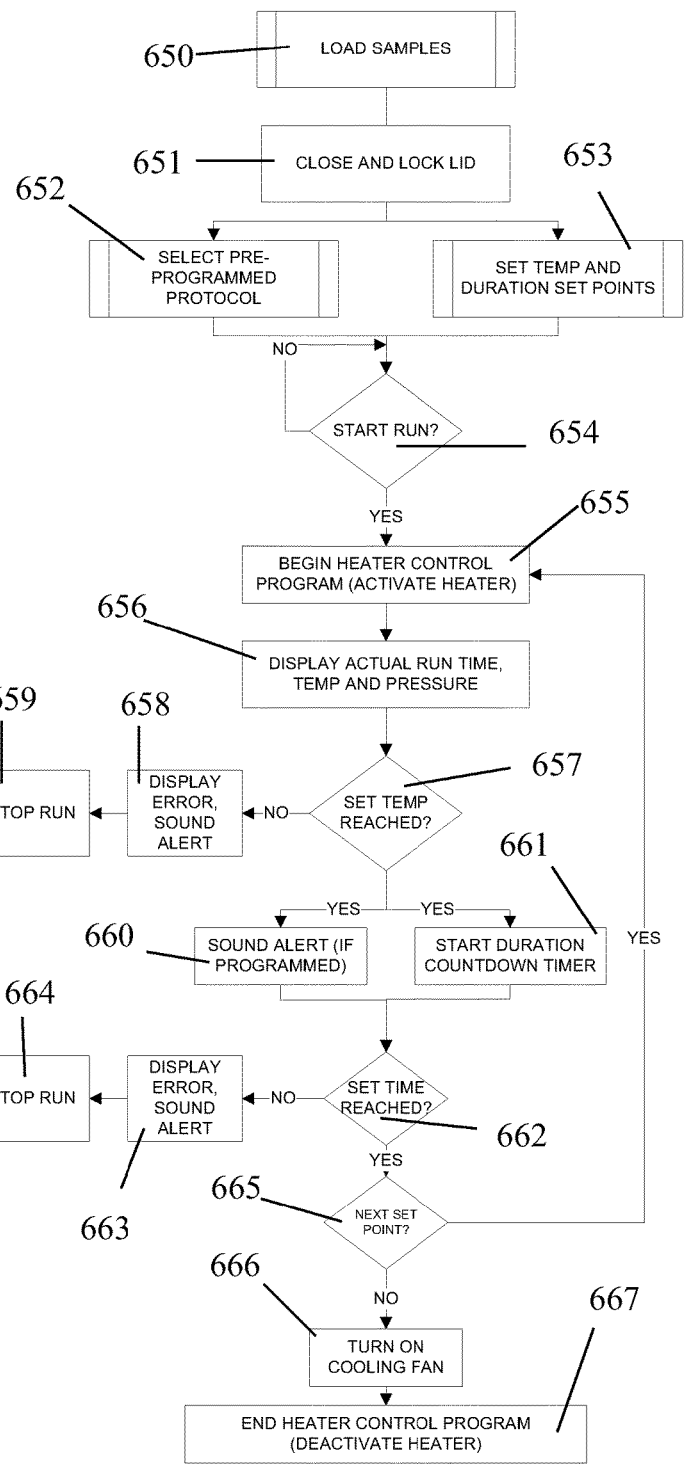
FIG. 15
FIG. 16

712

PROTOCOL

| TISSUE TYPE | ANTIBODY | AR SOLUTION |
|---|---|---|
| PROSTATE | PIN 4 | DIVA |

716

PROTOCOL

BIOCARE HIGH TEMP
BIOCARE LOW TEMP
USER PROTOCOL ANIMAL 1

MAIN MENU

HELP SELECT

BIOCARE HIGH TEMP

THE DECLOAKER IS FILLED WITH 100 ML OF DISTILLED WATER

THE 3 TISSUE TEK CONTAINERS ARE LOADED IN THE DECLOAKER WITH 200 ML OF AR SOLUTION OR DISTILLED WATER

721

BIOCARE HIGH TEMP

THE DECLOAKER IS FILLED WITH 100 ML OF DISTILLED WATER

THE 3 TISSUE TEK CONTAINERS ARE LOADED IN THE DECLOAKER WITH 200 ML OF AR SOLUTION OR DISTILLED WATER

722

BIOCARE HIGH TEMP

THE DECLOAKER IS FILLED WITH 100 ML OF DISTILLED WATER

THE 3 TISSUE TEK CONTAINERS ARE LOADED IN THE DECLOAKER WITH 200 ML OF AR SOLUTION OR DISTILLED WATER

MAIN MENU    START    HELP

723

RECOMMEND
PROTOCOL

TISSUE TYPE

HUMAN
PROSTATE
LIVER
LUNG

ANIMAL
BONE

ANTIBODY

ENTER NEW
PIN 4
TTF 1
CK 20
CEA

AR SOLUTION

ENTER NEW
BORG
REVEAL
DIVA
EDTA
TARGET

MAIN MENU

HELP

RECOMMEND
PROTOCOL

| TISSUE TYPE | ANTIBODY | AR SOLUTION |
|---|---|---|
| PROSTATE | PIN 4 | |
| | | BORG |
| | | DIVA |

MAIN MENU          HELP

RECOMMEND
PROTOCOL

TISSUE TYPE
PROSTATE

ANTIBODY
PIN 4

AR SOLUTION
DIVA

MAIN MENU

SELECT

HELP

729

ALARM

CHIME

VOICE

731

ALARM

CHIME

VOICE

734

ALARM

CHIME

VOICE

736

NEW PROTOCOL

PLEASE PROTOCOL NAME

MAIN MENU    SAVE    HELP

FIG. 53

METHODS AND SYSTEMS FOR IMMUNOHISTOCHEMISTRY HEAT RETRIEVAL OF BIOLOGICAL SAMPLES

This is a U.S. Non-Provisional Patent Application claiming priority to and the benefit of U.S. Provisional Patent Application No. 61/444,469, filed Feb. 18, 2011, hereby incorporated by reference herein.

BACKGROUND OF THE INVENTION

This invention relates generally to methods and apparatus related to heat induced antigen retrieval systems of biological specimens to protect, preserve, unmask or even enhance antigens or epitopes for further analysis.

Medical analysis of human or animal tissue specimens may include embedding the specimens in paraffin, cutting thin slices from the paraffin blocks, and placing the slices on microscope slides. The specimens are stained for improved viewing under a microscope. For further analysis, immunohistochemistry or similar techniques may be used, wherein monoclonal or polyclonal antibodies are used to identify tumors, infectious diseases, tissue constituents, etc. Some of the specimens may require the application of a heat retrieval method to permit the antibodies or probes access to the targeted antigen/epitope or sequence. The heat retrieval method may include placing a retrieval solution on the slides and heating the slides to between about 80° C. and about 120° C. or perhaps even between about ambient room temperature to about 128° C. in a heating device such as a microwave, steamer, rice cooker, pressure cooker, or autoclave. Using a pressure cooker raises the boiling point of the solution and prevents it from boiling off at maximum cooker temperature, and also speeds up the process. After heating, the slides are removed from the heating device for immunohistochemistry analysis.

A major problem with heating slides in a conventional cooking device such as a microwave or pressure cooker is that the temperature and pressure cannot be monitored for precise and reliable results as well as other system deficiencies including the need for at least some automation. According to laboratory governing bodies that issue operating standards for quality control, such as the College of American Pathologists (CAP), daily quality control measures should be implemented for such laboratory testing. Typical guidelines issued by a governing body are as follows: 1. Laboratory tests using a heating device should have the temperature recorded. 2. Laboratory tests using pressure should have the pressure recorded. 3. The pH of solutions for heat retrieval procedures should be recorded at the temperature used. 4. Any electrical water bath should have a 3-prong power plug.

Conventional cooking devices cannot efficiently measure temperature, pressure, or pH. In the past, if a device does not measure temperature, it cannot be used for complying with laboratory quality control standards. Another problem is that past devices may not automatically adjust the total heating time to compensate for different amounts of materials in the cooker, since more massive contents must be heated longer than with less contents. Additional heating device systems are discussed in U.S. Pat. No. 6,580,056 to Tacha, hereby incorporated by reference in its entirety.

SUMMARY OF THE INVENTION

The present invention may include, in embodiments, systems and methods for processing of biological samples for deparaffinization and even antigen retrieval. It is an object of the present invention, in embodiments, to provide a substantially user-disencumbering autonomous processing component of biological samples.

It is another object of the present invention, in embodiments, to provide nonpareil operation of a sealable heating pressure chamber device perhaps to allow more efficient processing of biological samples.

It is yet another object of the present invention, in embodiments, to provide dynamically responsive processing of biological samples perhaps to allow automatic dynamic reactions to various processing elements.

Naturally, further objects, goals and embodiments of the inventions are disclosed throughout other areas of the specification, figures, and claims.

BRIEF DESCRIPTION OF THE DRAWINGS

FIG. 15 is an example of a flowchart of an embodiment of a quality control process for using a sealable heating pressure chamber system.

FIG. 16 is an example of a flowchart of the operation of an embodiment of a controller in accordance with embodiments of the present invention.

FIG. 40 is an example of a recommended protocol screen for a user interface system in accordance with embodiments of the present invention.

Figure 42:
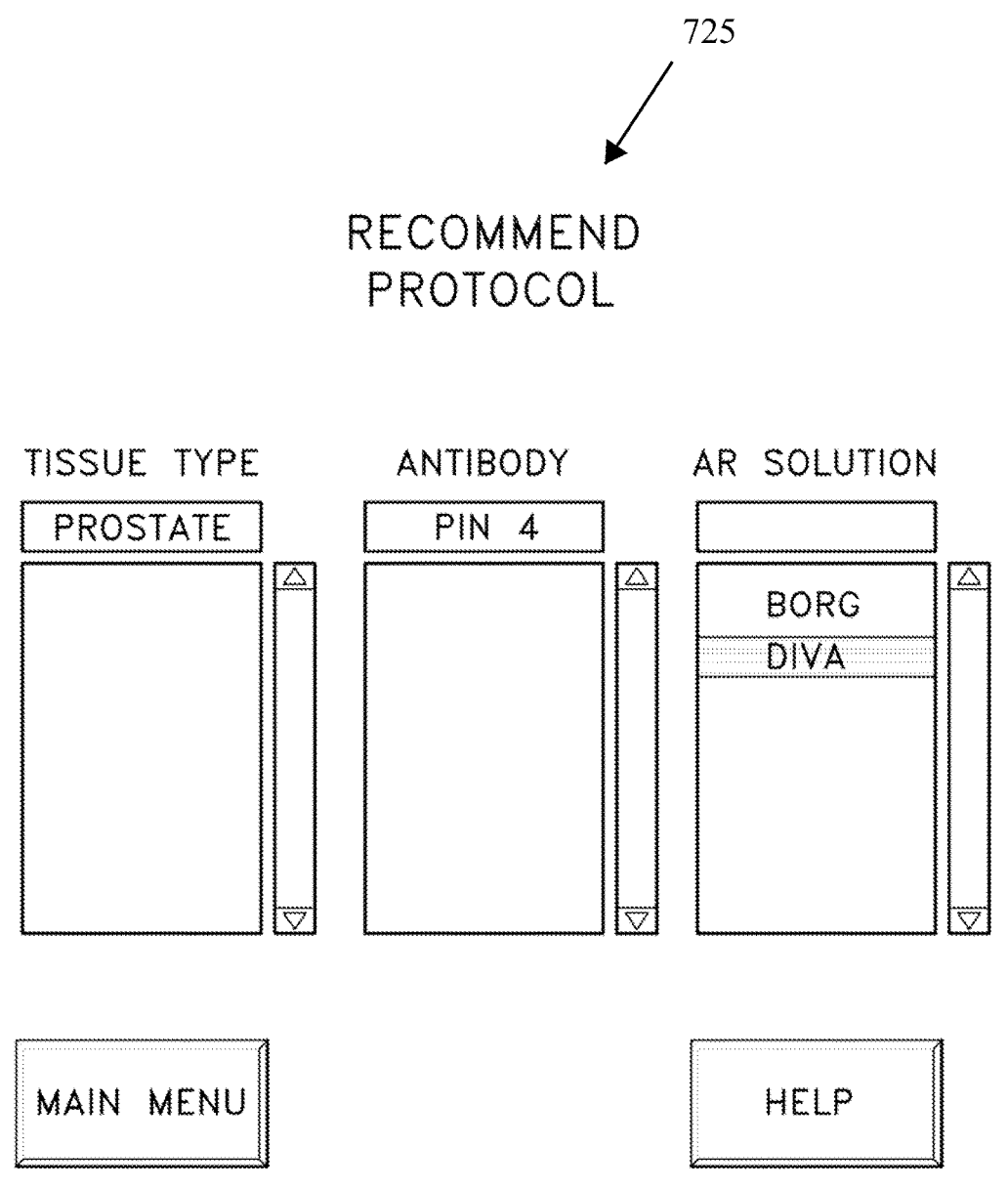

FIG. 42 is an example of an alternative recommended protocol screen for a user interface system in accordance with embodiments of the present invention.

FIG. 53 is an example of a new protocol screen for a user interface system in accordance with embodiments of the present invention.

DETAILED DESCRIPTION OF THE PREFERRED EMBODIMENTS

The present invention includes a variety of aspects, which may be combined in different ways. The following descriptions are provided to list elements and describe some of the embodiments of the present invention. These elements are listed with initial embodiments, however it should be understood that they may be combined in any manner and in any number to create additional embodiments. The variously described examples and preferred embodiments should not be construed to limit the present invention to only the explicitly described systems, techniques, and applications. Further, this description should be understood to support and encompass descriptions and claims of all the various embodiments, systems, techniques, methods, devices, and applications with any number of the disclosed elements, with each element alone, and also with any and all various permutations and combinations of all elements in this or any subsequent application.

In general, embodiments of the present invention may provide efficient systems and methods for antigen retrieval processing of biological specimens. Some embodiments may provide semi-automated biological specimen antigen retrieval pressure cooker device-type systems and some embodiments may provide methods of semi-automatically retrieving antigens from biological specimens. In semi-automated systems and methods some elements or steps may be accomplished by a machine perhaps making it automated and other elements or steps may be accomplished manually. Non-limiting examples of manual components include, but are not limited to, user supplying liquid to a sealable heating pressure chamber; user covering a lid of a sealable heating pressure chamber; user sealing a sealable heating pressure chamber; user placing slides in a sealable heating pressure chamber; user placing loaded containers in a sealable heating pressure chamber; user-entering at least one protocol; any combination thereof; and the like. A biological sample may include, but is not limited to, an embedded biological sample, a biological tissue sample, a biological fixed sample, a formalin-fixed sample, a paraffin embedded biological tissue sample, and the like. A slide or plurality of slides as may be discussed herein is not meant to limit the invention and a slide may be any kind of biological sample support which may provide utility for a biological sample to be processed in a sealable heating pressure chamber and the like embodiments.

Figure 8:
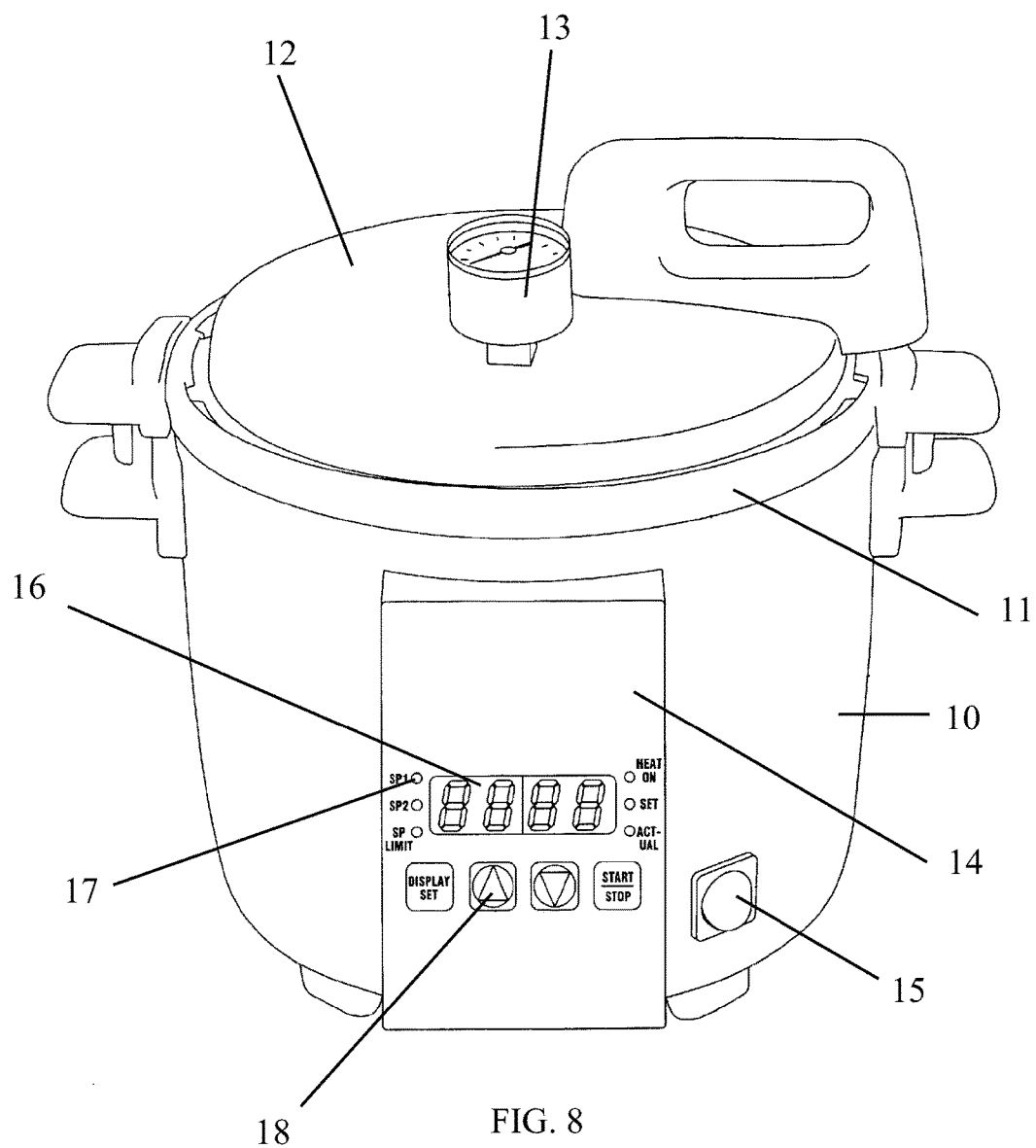
FIG. 8 is a front perspective view of an alternative example of an embodiment of a sealable heating pressure chamber.

In embodiments of the present invention, an example of a biological specimen heating device for immunohistochemistry procedures may be shown in a front perspective view in FIG. 8. An electric pressure cooker 10 may include a pressure chamber 11 (only the top rim is shown), a removable lid 12 covering pressure chamber 11, a pressure gauge 13 attached to lid 12, a controller 14 attached to a front side, and perhaps even a power switch 15 attached to the front side. A pressure gauge 13 may be communicably connected to an internal surface of lid 12 for sensing the pressure inside cooker and may be calibrated to read from about 0 psi to at least about 30 psi. A controller 14 may be arranged to control and even display a cooker temperature and perhaps even a control heating time. Controller 14 perhaps even a programmable process controller or even an automatic antigen retrieving processor controller may include a digital controller or perhaps even a SBC (single board computer), although an analog controller may be provided or display. Controller 14 may include a display 16, indicator lights 17, and perhaps even a keypad 18 or even a touch-screen panel. Controller 14 may integrate a temperature control, a timer control, and even a time/temperature/pressure display.

Figure 1:
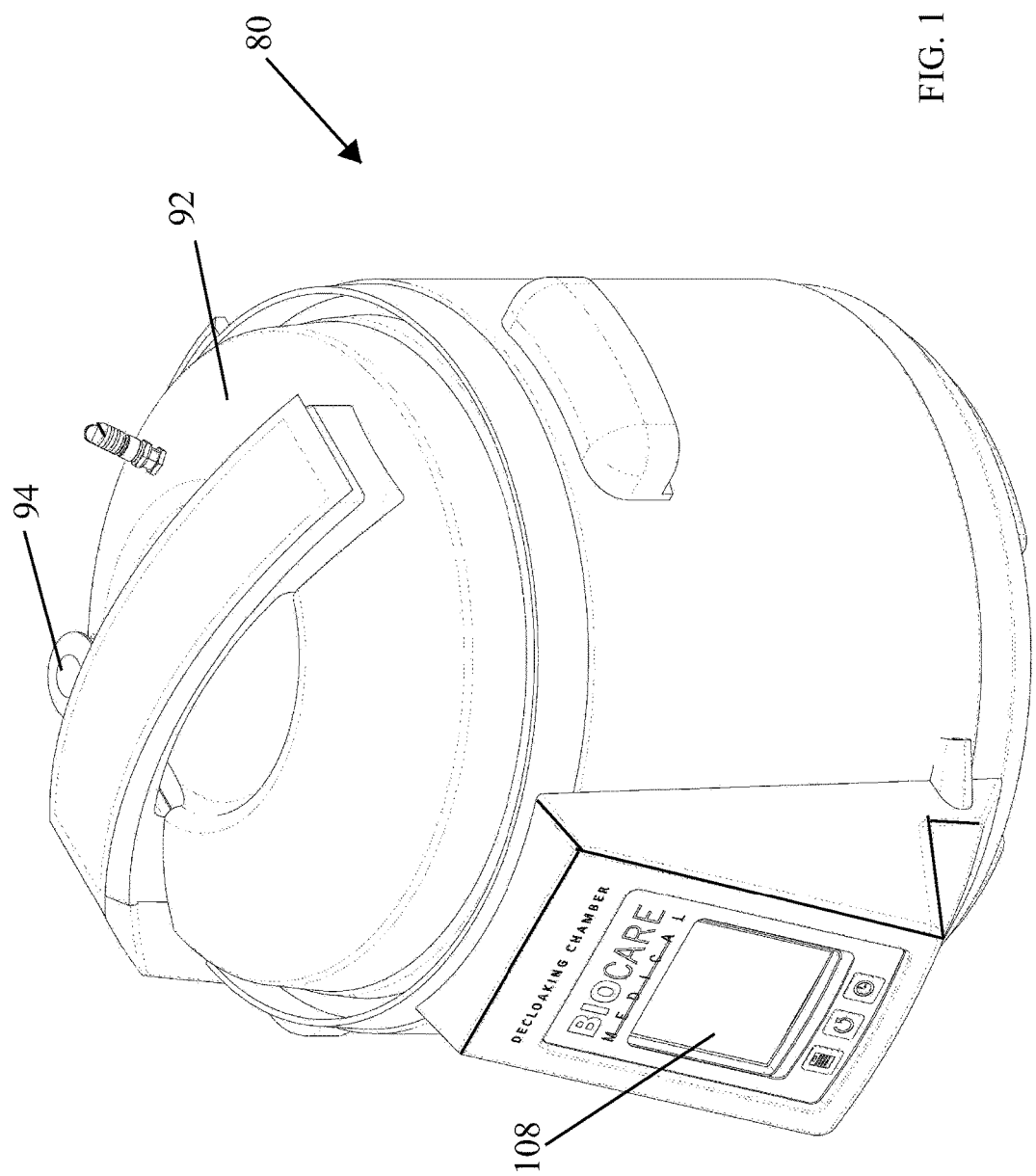
FIG. 1 is a front perspective view of an example of an embodiment of a sealable heating pressure chamber device in a closed position.
Figure 2:
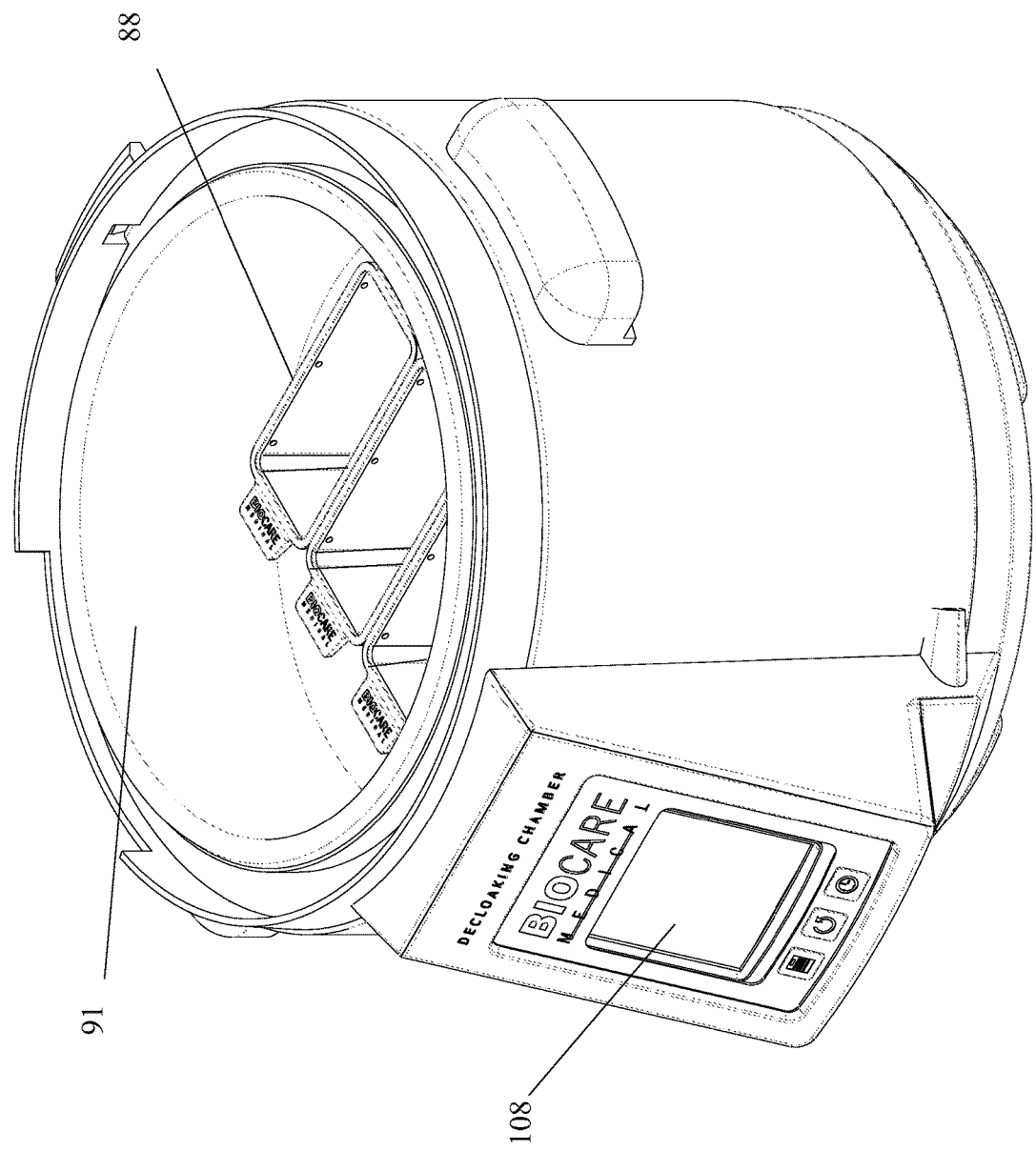
FIG. 2 is a front perspective view of an example of an embodiment of a sealable heating pressure chamber device in an open position.
Figure 3:
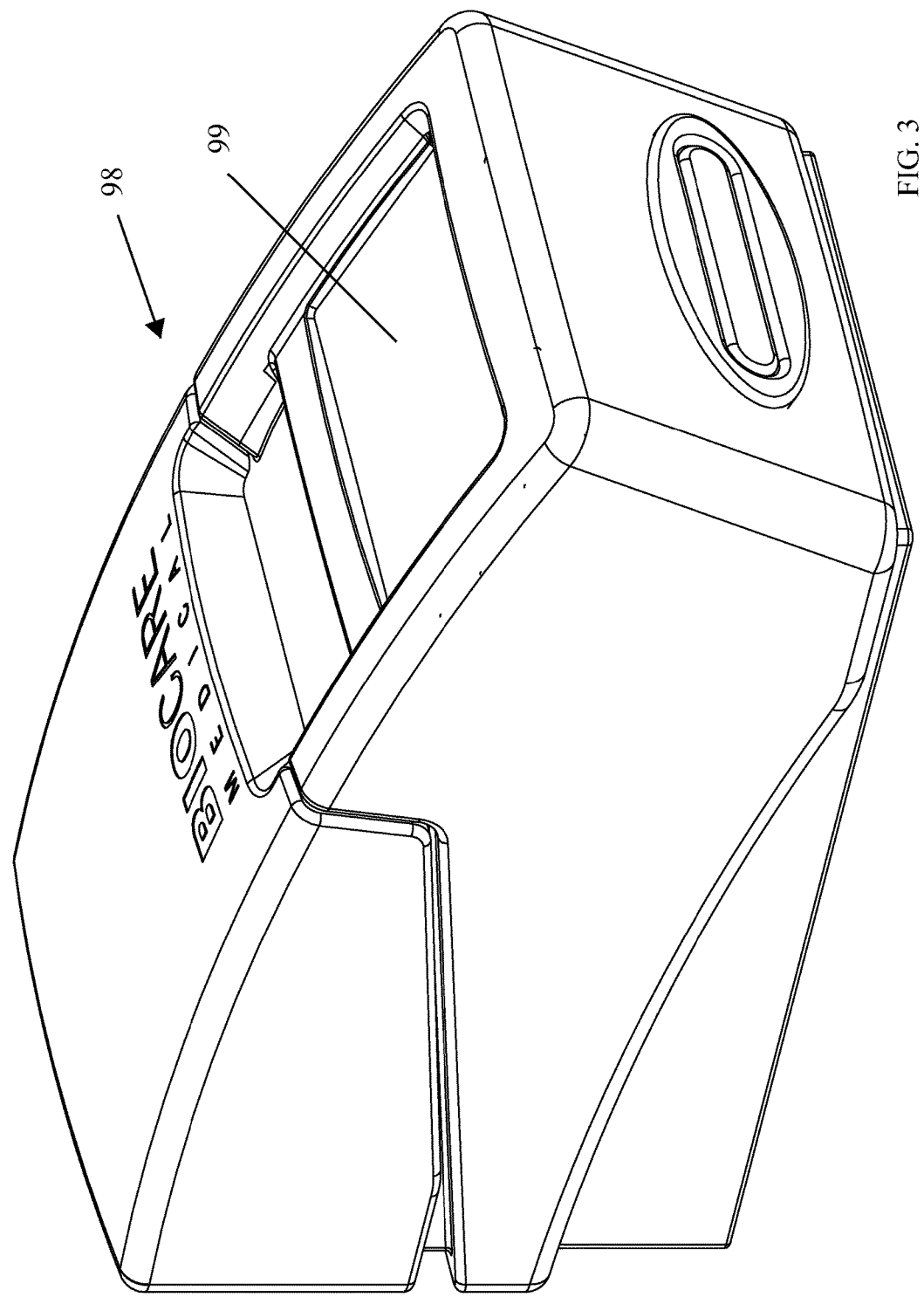
FIG. 3 is a front perspective view of an example of an alternative embodiment of a sealable heating pressure chamber device in a closed position.
Figure 4:
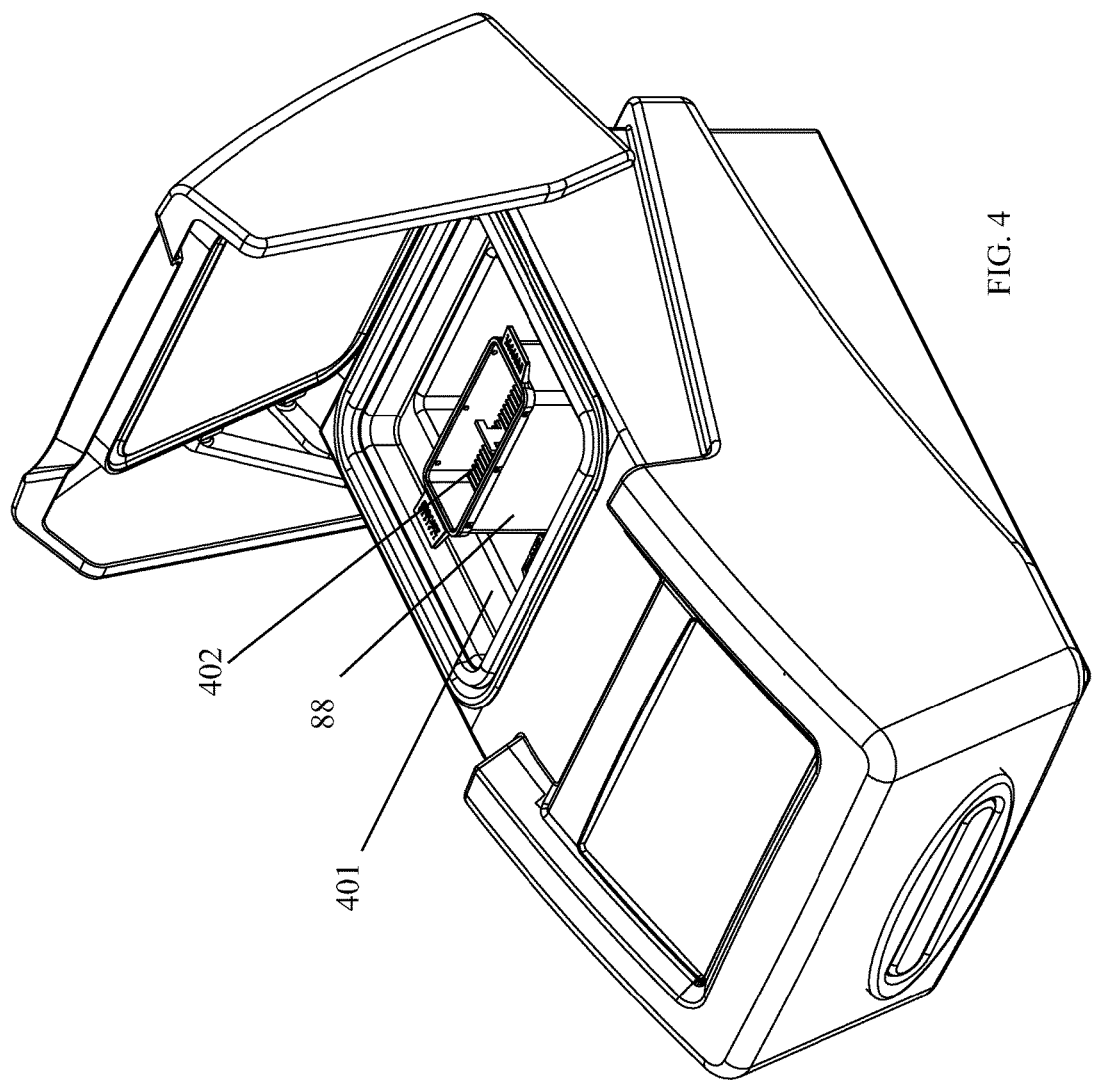
FIG. 4 is a front perspective view of an example of an alternative embodiment of a sealable heating pressure chamber device in an open position.

In other embodiments of the present invention, a sealable heating pressure chamber (80) may be provided such as shown in FIG. 1 and FIG. 2. A lid (92) such as a sealable lid may be provided as well as a pressure release valve (94) in various embodiments. A computer with a display (108) may be provided on or even near a sealable heating pressure chamber device. An internal chamber (91) of a sealable heating pressure chamber (80) may be configured to receive a plurality of slides or may even be configured to receive at least one slide container (88) which may each hold a plurality of slides. A slide container (88) may be a vertical slide position holder, a metal container, a horizontal slide position holder, a multi-slotted container, a combination slide and solution holder, and the like in various embodiments. In FIG. 2, three slide containers (88), perhaps even multi-slide containers, may be placed in a sealable heating pressure chamber. Of course, any number of slides and even any number of containers may be used in a sealable heating pressure chamber. As but one non-limiting example, a slide placement may be configured to receive up to about 96 slides. In an alternative design, FIG. 3 and FIG. 4 show an example of a sealable heating pressure chamber (98) and a display (99). A display (99) may show a variety of different items such as, but not limited to, the following elements: pressure, temperature, time, protocol information, user-selection options, graphical display of real-time run progress, process error warning indicators, combination thereof, and the like. FIG. 4 shows an alternative design of an internal chamber (401) of a sealable heating pressure chamber system. As discussed herein, a slide container (88) may provide slots (402) perhaps to hold a plurality of slides.

Figure 5A:
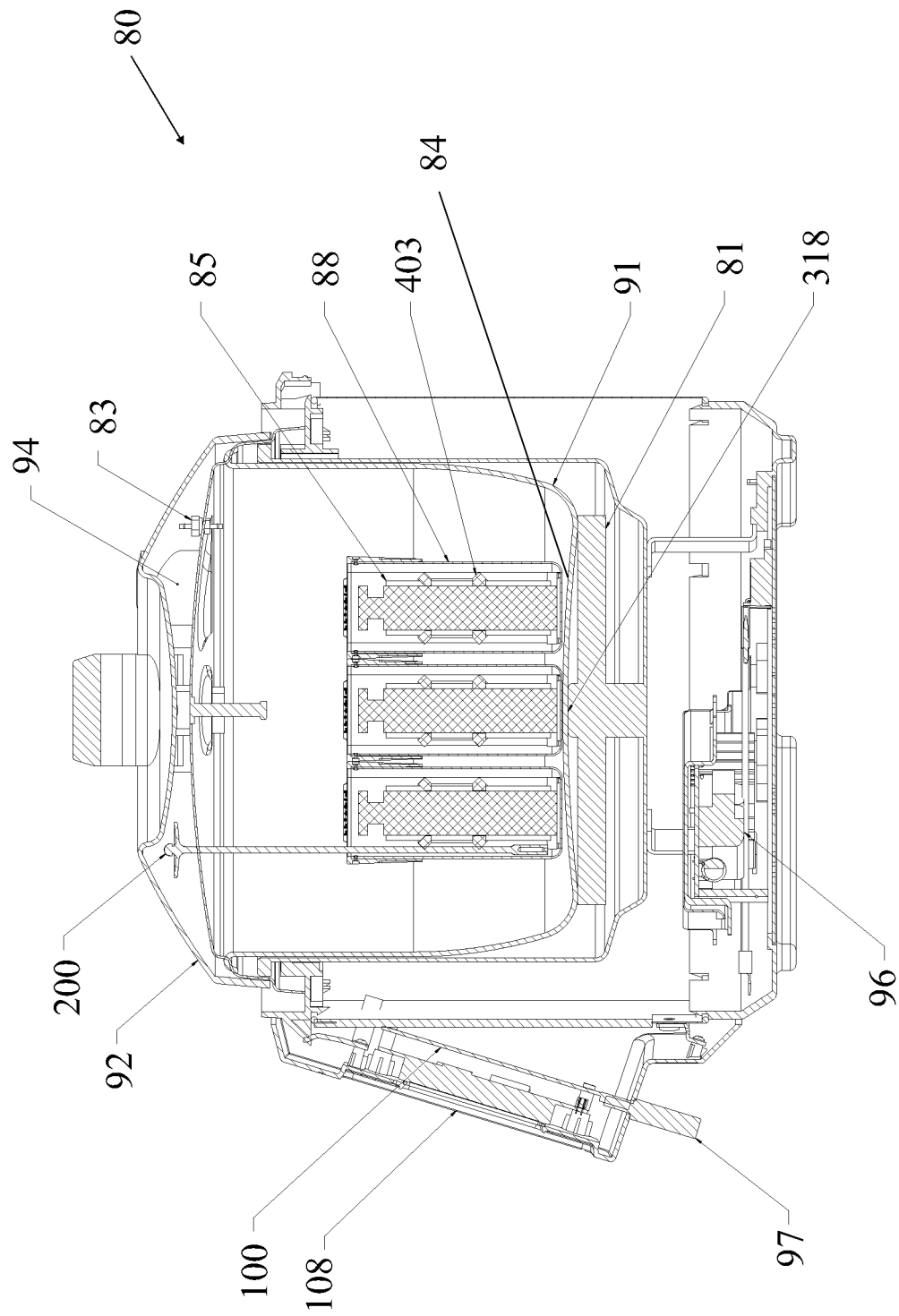
FIG. 5A is a sectional side view of an example of an embodiment of a sealable heating pressure chamber device.
Figure 5B:
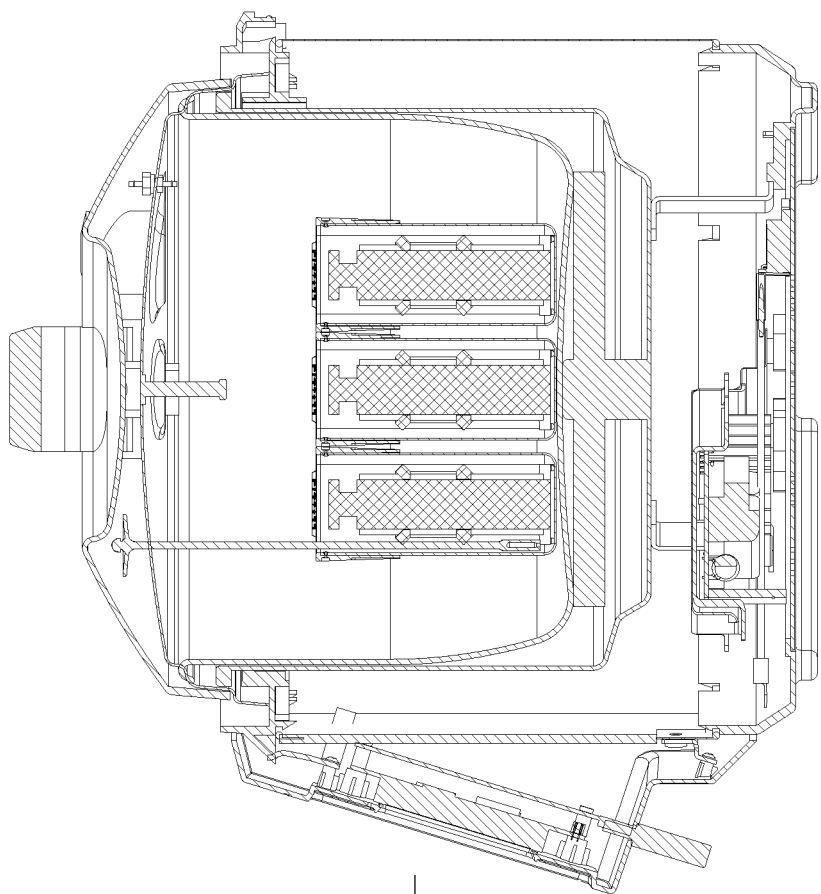
FIG. 5B is a sectional side view of an example of an embodiment of a sealable heating pressure chamber device with a remotely monitoring processing component.

As may be understood from FIG. 5A and FIG. 5B, a sealable heating pressure chamber may include various different elements. As a non-limiting example, a sealable heating pressure chamber (80) may have an internal chamber (91) and may have a controller (100) and a display (108) perhaps on the exterior of the sealable heating pressure chamber. Data storage (97) may be provided and may be removable, connectable, downloadable, or the like. A lid (92) may be provided perhaps with a pressure release valve (94) and even a pressure sensor (83). A lid (92) may be sealable perhaps with a sealing gasket or the like. An internal temperature sensor (200) may be provided to sense a temperature within a sealable heating pressure chamber or perhaps even within a slide container. A temperature sensor may sense the an internal chamber temperature, a temperature of a slide, a temperature of a biological sample, a temperature of a solution, a temperature of a liquid, or the like within or perhaps at any location in a sealable heating pressure chamber. As discussed herein, a slide (85) may be contained in a slide container (88). Within the slide container, the present invention may provide at least one slide holder (403) which may be functional to allow placement of a slide inside a container and may even hold a slide so that it may not interfere with other slides and can be processed effectively. A sealable heating pressure chamber may provide a slide placement (84) perhaps even a slide container placement where slides or slide containers may be placed in the sealable heating pressure chamber. For example, a slide placement (84) may be located near or at a bottom of a chamber; however any location in a chamber may be used. A heater (81) may be provided to allow a sealable heating pressure chamber to be heated. A heat source temperature sensor (318) may be provided perhaps near a heater (81) such as a heat source. A power board (96) may also be provided. Each of these non-limiting examples may be used individually or may even be combined in various embodiments of the present invention. As may be understood from FIG. 5B, in embodiments, a computer with a display with may be a remotely monitoring processing component (106) such as a removable device as will be discussed herein.

Figure 6:
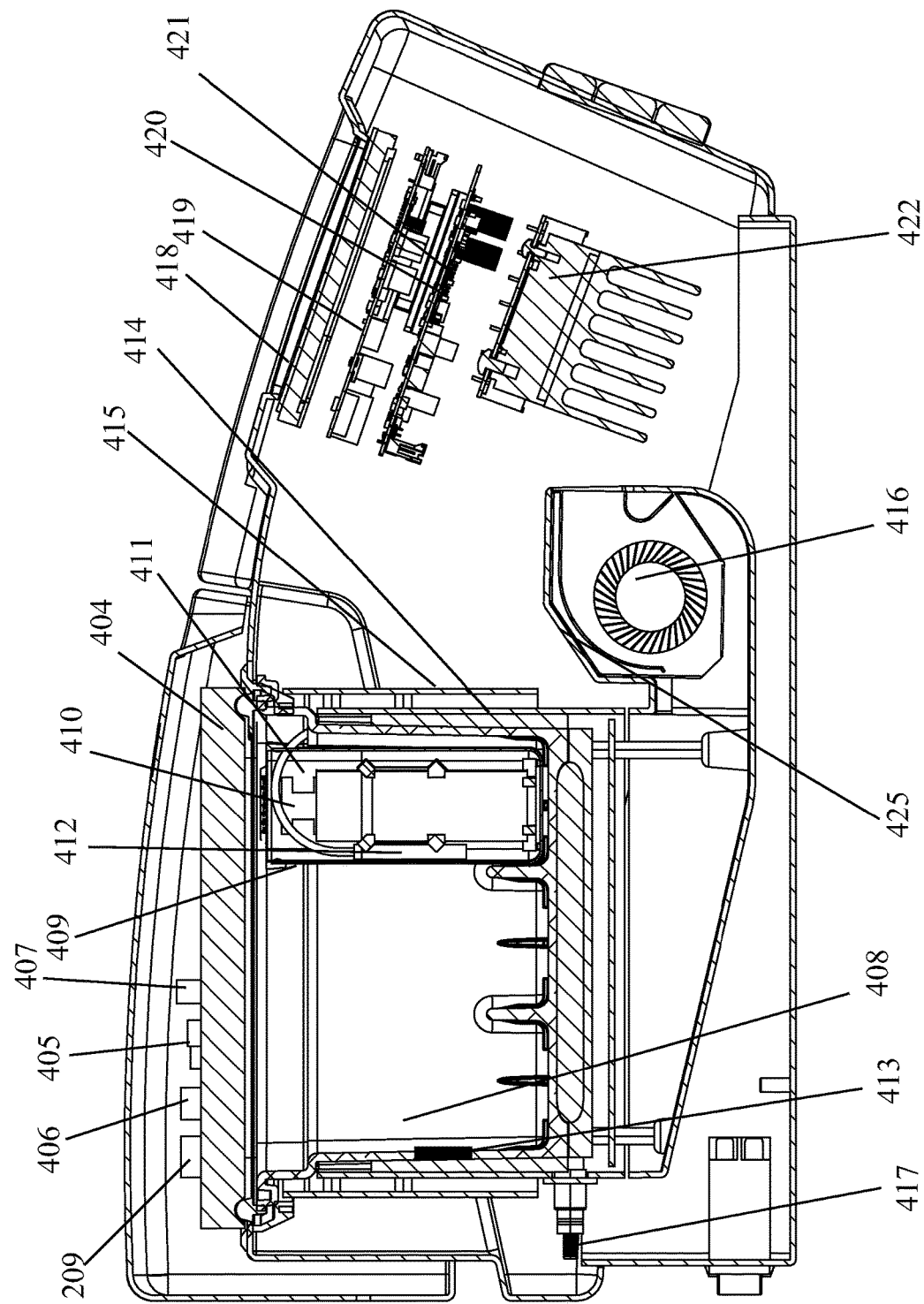
FIG. 6 is a sectional side view of an alternative example of an embodiment of a sealable heating pressure chamber device.

FIG. 6 shows a partial side view an example of a system, in various embodiments, which may include, but is not limited to: a lid (404); a pressure release valve (405) to perhaps control pressure during operation; a pressure safety valve (406) to perhaps release pressure if recommended levels may be exceeded; a pressure sensor (407) to detect chamber pressure; an air circulating pump (209) to perhaps circulate air in the chamber during slide drying; a pressure chamber (408) which may be an internal chamber; specimen containers (409); a slide holder (410); slides (411) (with perhaps biological samples, not shown); a temperature probe (412) to perhaps sense a solution such as a pH solution temperature directly; a temperature sensor (413) to perhaps sense a common liquid temperature as well as perhaps even detect over-temperature conditions due to insufficient or no common liquid in the chamber; an inner (414) and outer (415) plenums perhaps used to direct cooling air over the cooling fins integrated into the chamber; a fan (416) perhaps used to exhaust hot air from the instrument through the fan plenum (425); a heater element (417); a display (418); a computer module (419) which may have master control of all functional aspects of the instrument; an analog control board (420) which may receive and convert analog signals from sensors and may even send information to the digital control board (421) which may communicate all functional parameters to the computer module; a power control board (422) to perhaps convert and control incoming power and distribute to elements of the instrument; any permutation or combination of the above; and the like.

Figure 7:
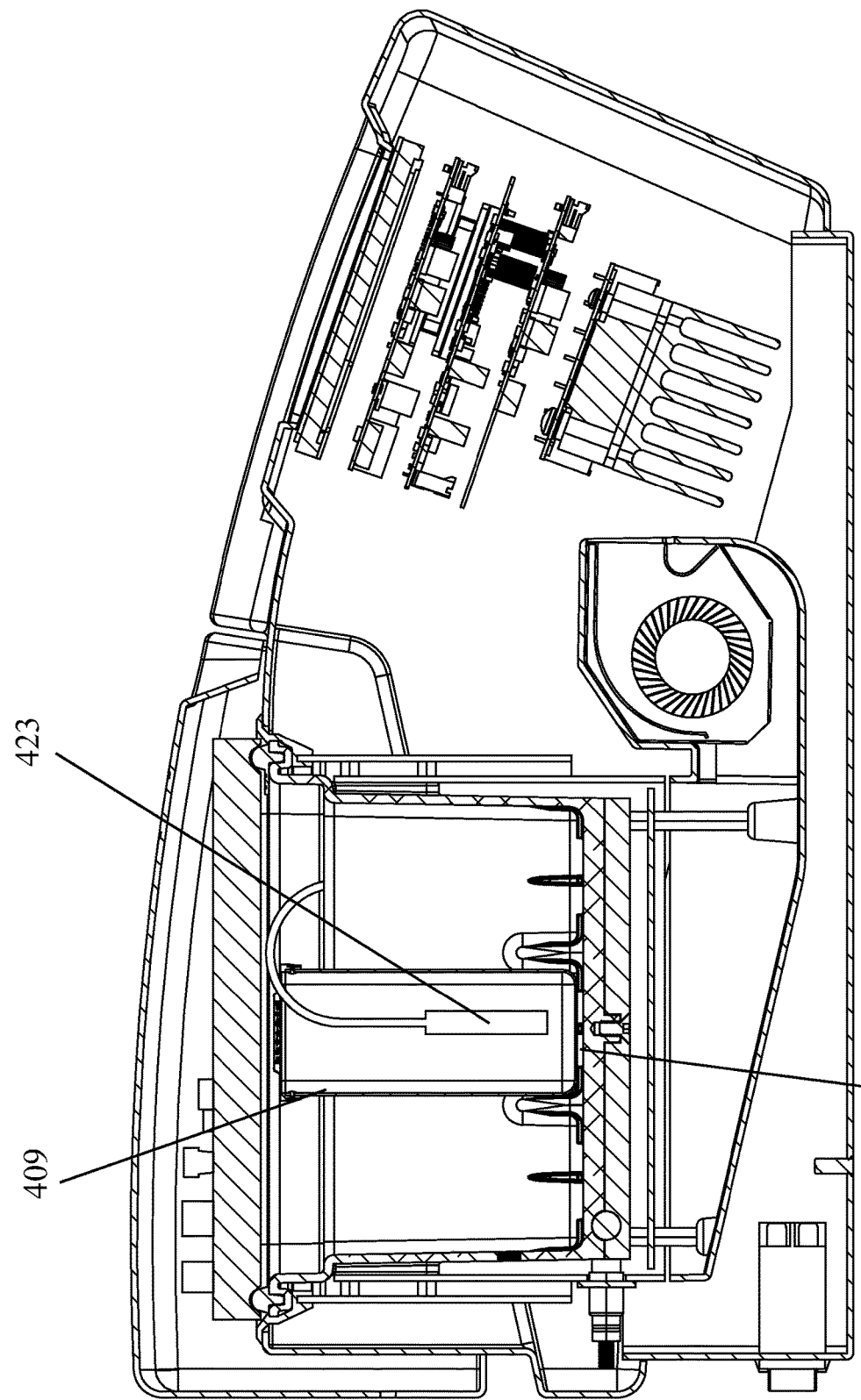
FIG. 7 is a sectional side view of an alternative example of an embodiment of a sealable heating pressure chamber device.

FIG. 7 shows an alternative example of a temperature probe (423) in a container. FIG. 7 also shows an example of a separate slide container placement (424) for at least one slide container (409) in accordance with some embodiments of the present invention. Other embodiments of the present invention may include a flow chart describing an operation of a remote time as shown in FIG. 9, a process flow map of an example of operational software interface as shown in FIG. 10, and perhaps even an alternative flow chart for a heating pressure chamber system as shown in FIG. 11.

Figure 9:
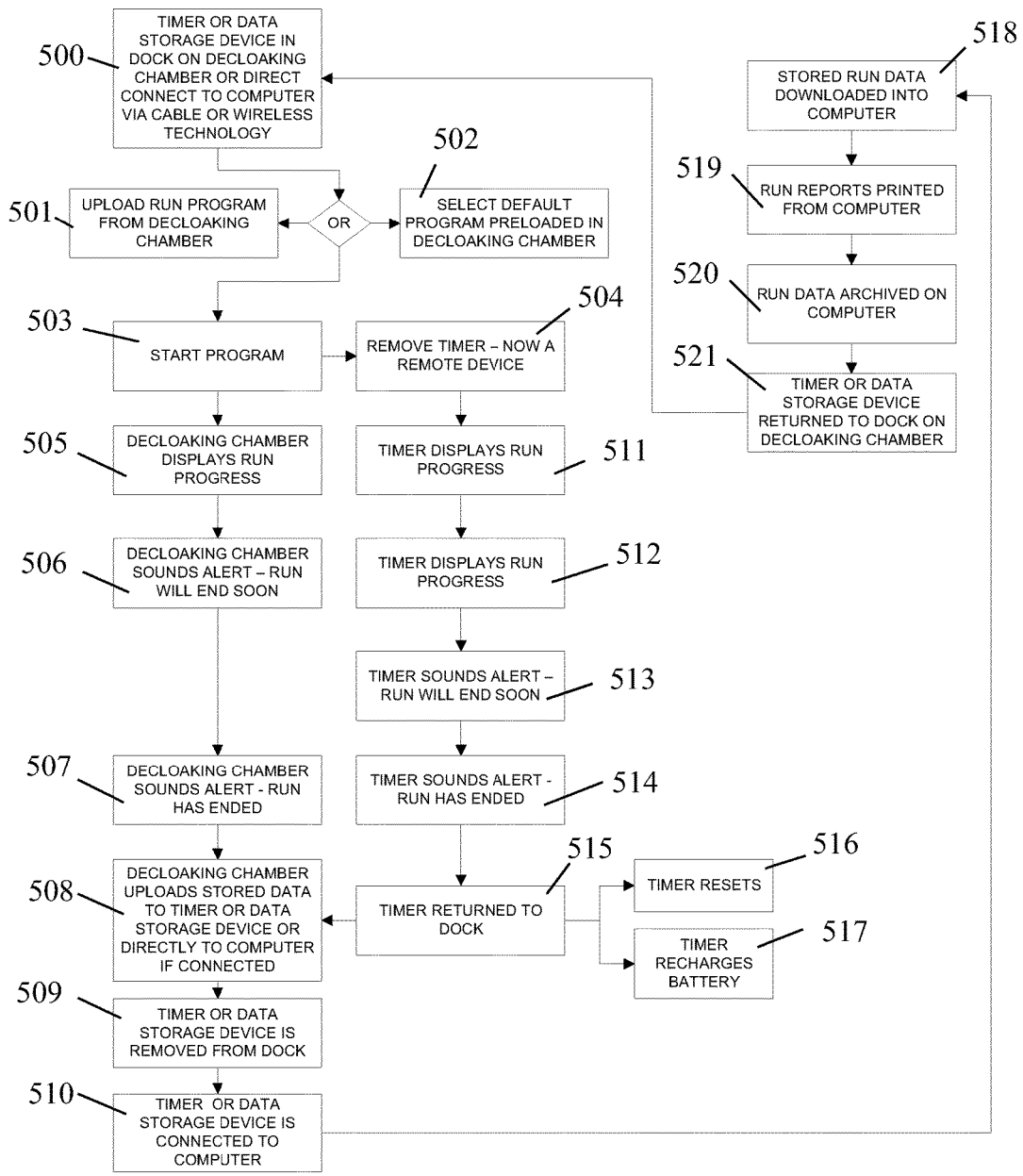
FIG. 9 is an example of a flow chart for the operation of a remote device in accordance with embodiments of the present invention.

As represented in FIG. 9, various embodiments of the present invention may include operation of a remote device. A remote device, perhaps a timer, remote timer, a data storage device, a remote alarm, a plurality of remote alarms, a remote error indicator, a remote card or the like systems may be docked on a chamber or may even be removably connected to a pressure chamber perhaps through a computer with a direct connection, cable, wireless technology, or the like (500). A run program may be uploaded from a chamber (501) or a user may select a default program perhaps preloaded in a chamber computer device (502). A program may be started (503) and a chamber may display a run progress (505) of at least one program run. A chamber may provide an alert, such as a sound alert, alerting that the run may end soon (506). A chamber may sound an alert that a run has ended (507). A chamber may upload stored data to a device such as a timer or data storage device or may even upload directly to a computer (508). A program may be started (503) and a device may be removed from a docking placement or the like so that it may be a remote device (504). A remote device may display a run progress (511), a remote device may display an updated run progress (512) such that it may be a continuous run progress or even a continuously responsive dynamic run progress. A remote device may sound an alert that a run may end soon (513) and a remote device may even sound an alert that a run has ended (514). A user may return a remote device to a dock (515) so that it can be uploaded with stored data from a chamber (508). A remote device may be reset (516) or may even be recharged (517). After a device, which may be a remote device, a storage device, a flash drive, or the like may be uploaded with data from the chamber, it may be removed (509) and connected to a computer (510). Stored run data may be downloaded into a computer (518) where run reports may be printed from a computer (519) and run data may be archived on a computer (520). A device may be returned to a dock on a chamber (521) for another processing run or the like.

Figure 10:
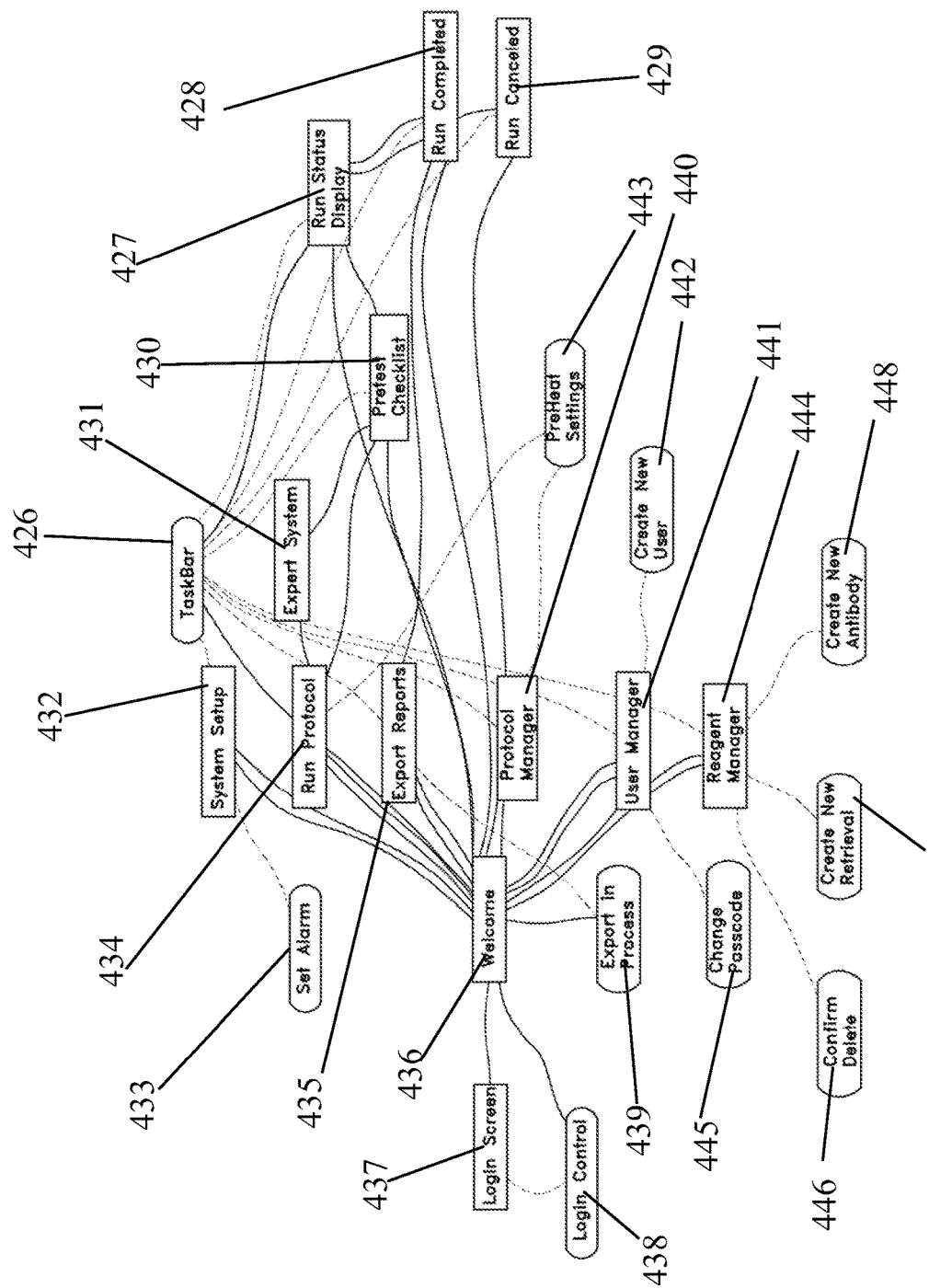
FIG. 10 is a process flow map of an example of an operational software interface in accordance with embodiments of the present invention.

Examples of an operational software interface of a sealable heating pressure chamber system may include various elements as represented in FIG. 10. An example of an operation software interface may include, but is not limited to, a task bar (426), system setup (432), set alarm (433), a run protocol (434), an expert system (431), run status display (427), export reports (435), pretest checklist (430), run completed (428), run canceled (429), login screen (437), welcome (436), protocol manager (440), login control (438), export in process (439), user manager (441), change protocol (445), confirm delete (446), create new protocol (447), create new antibody (448), create new user (442), preheat settings (443), any combination thereof, and the like.

Figure 11:
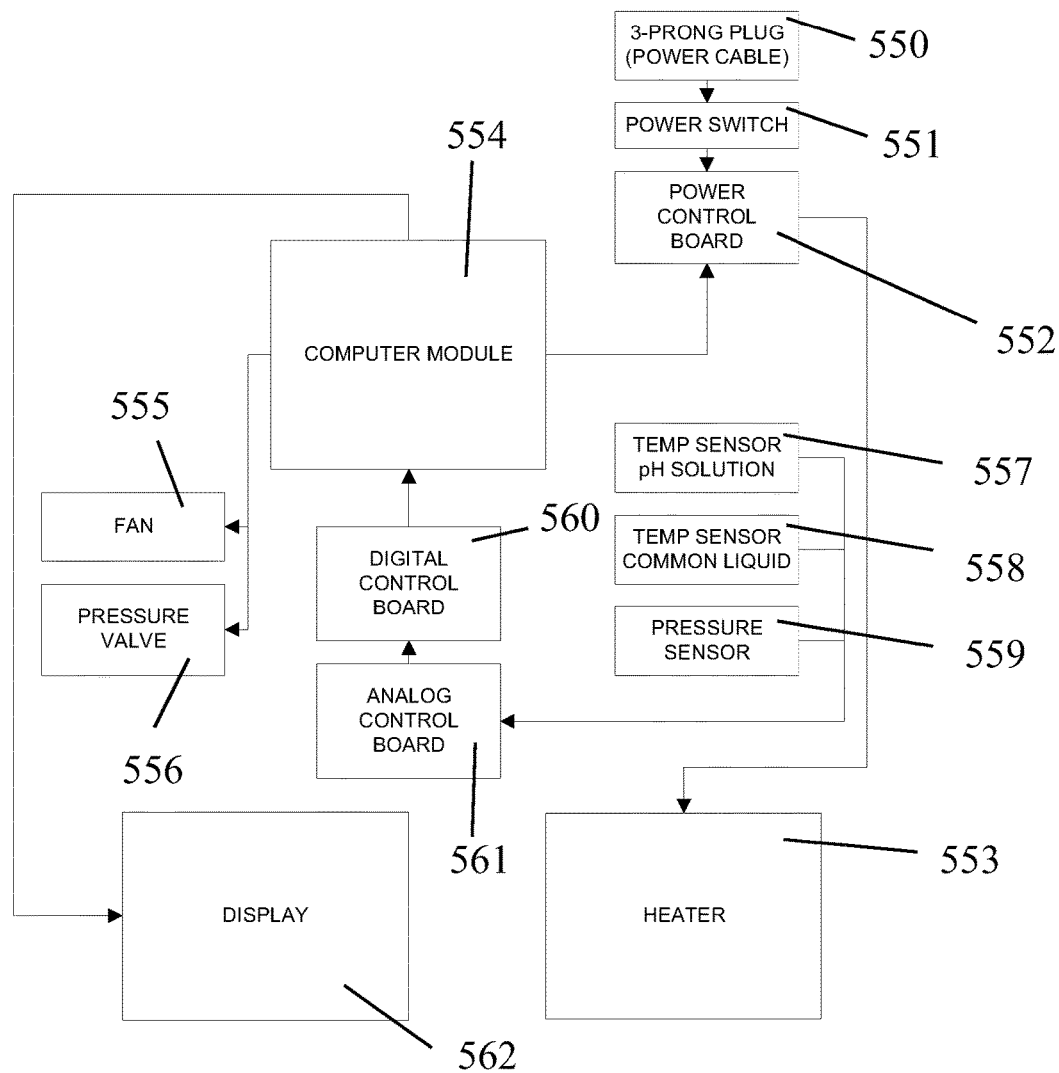
FIG. 11 is an example of a block diagram of operational components of an embodiment of a sealable heating pressure chamber device.

A sealable heating pressure chamber system may use a variety of operational components including but not limited to a power cable such as a 3-prong plug (550), a power switch (551), a power control board (552), a heater (553), a temperature sensor of a pH solution (557), a temperature sensor of a common liquid (558), a pressure sensor (559), an analog control board (561), a digital control board (560), a computer module (554), a fan (555), a pressure valve (556), a display (562), any combination thereof, and the like as represented in FIG. 11.

Figure 12:
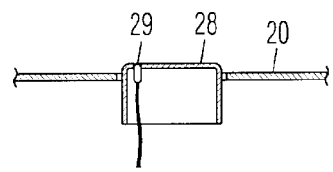
FIG. 12 is a sectional view of an embodiment of a temperature sensor in accordance with embodiments of the present invention.

A sectional view of a sensor button (28) in heating element (20) is shown in FIG. 12 in accordance with some embodiments of the present invention. A sensor button (28) may be a common feature in many pressure cookers and rice cookers. A pressure chamber (not shown) may be typically positioned on top of sensor button (28). A temperature sensor (29) may be attached to sensor button (28), perhaps inside a hole extending through a top surface of sensor button (28).

Figure 13:
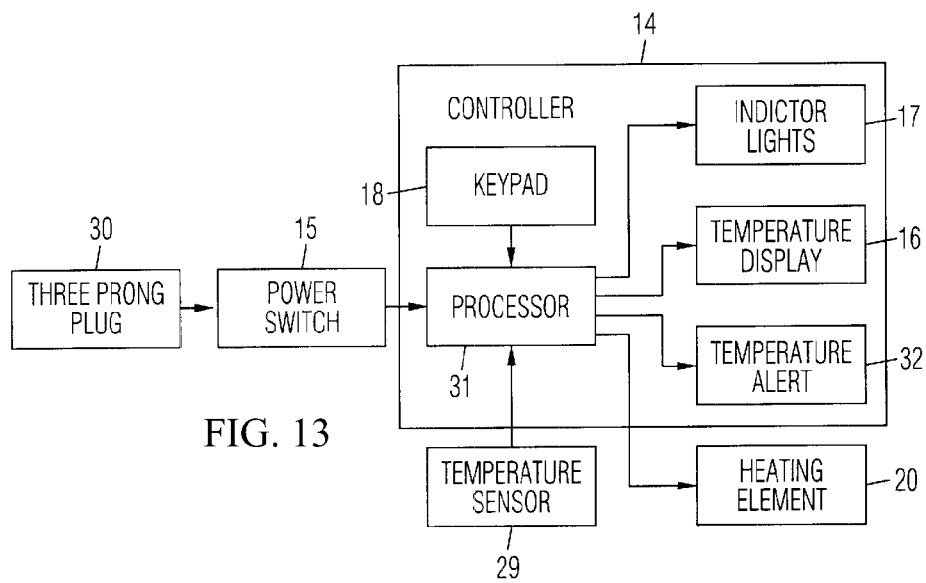
FIG. 13 is a schematic block diagram of an embodiment of a sealable heating pressure chamber system in accordance with embodiments of the present invention.

An example of a schematic block diagram of the heating device is shown in FIG. 13. A three-prong plug (30) that includes a ground connector may be provided for meeting laboratory governing body operating standards. Plug (30) may be connected to power switch (15) which provides power to controller (14). Controller (14) may include a processor (31) connected to keypad (18), indicator lights (17), display (16), a temperature alert (32), temperature sensor (29), and perhaps even a heating element (20). A temperature alert (32) may be an audio and/or visual alert or the like.

Figure 14:
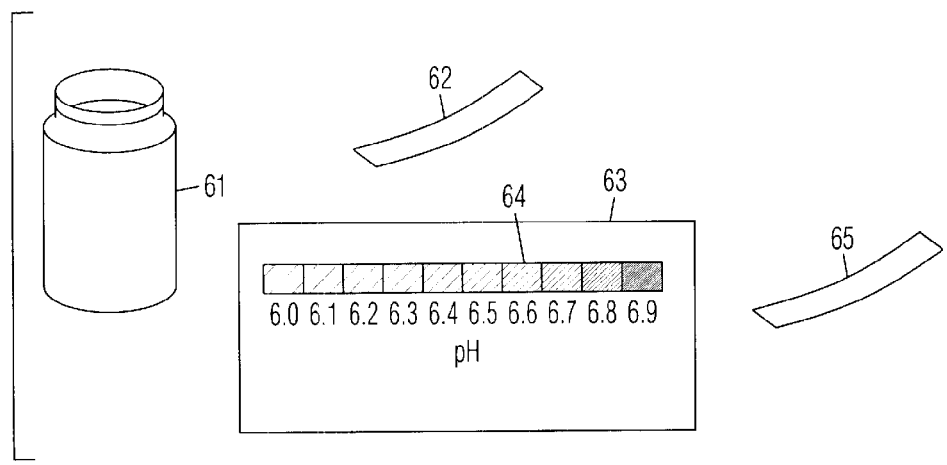
FIG. 14 is a front view of an example of an embodiment using quality control devices used with a sealable heating pressure chamber system.

As shown in FIG. 14, quality control devices for use with the present heating device includes a first pH indicator or pH indicating retrieval solution (61), a second pH indicator or pH strip (62), a heat adjusted color chart (63) with a temperature adjusted color range 64, and perhaps even a heat and pressure sensitive steam strip (65). An example of the use of a device may be disclosed in conjunction with FIG. 8.

The programming and operation of a controller may include, in embodiments, after power up, a maximum cooker temperature may be set, and the timer may be set. When the start button may be pressed, the heating element may be activated. The actual temperature may be measured by a temperature sensor and may be continuously updated and displayed. When the set temperature may be reached, a timer may be started to maintain the set temperature for the set duration. When a timer expires, the temperature alert may be sounded, and the heating element may be deactivated. The actual temperature may be continually displayed and updated even after the timer expires. Since more massive materials may require longer a heating time to reach the set temperature and vice versa, starting the timer after the set temperature has been reached may automatically adjust the total heating time to compensate for the mass of the materials being heated.

Alternatively, the processor may be arranged to enable the setting of a plurality of set points, wherein each set point may be comprised of a temperature and timer duration. When the start button may be pressed or even activated, a heating element may be activated perhaps until the first set point has been reached, and then may be deactivated. When a start button may be pressed or otherwise activated again without turning off the controller, a heating element can be activated again until a second set point has been reached, and so forth. The first set point may be a maximum temperature, and the second set point may be a keep-warm temperature. The second set point may also be a cooling down period in which the temperature is set at about 0 to keep the heating element turned off. When the second set point has been reached, an alert may be sounded to notify the user that the cooker has cooled and depressurized enough to be opened safely.

As represented in FIG. 16, system and methods may include, but are not limited to, loading samples such as slides supporting biological samples (650); closing and locking a lid (651) which may include any kind of locking feature such as, but not limited to, a safety lock, lid lock, drain lock, and the like; selecting pre-programmed protocol (652); selecting set temperature and duration set points (653); starting a run (654); begin heater control program with perhaps activation of a heater (655); display actual run time, temperature, and/or even pressure (656); reaching a set temperature (657); if a set temperature has not been reached, displaying an error, alarm, sound alert, or the like (658), and perhaps stopping a run (659); if a set temperature has been reached, sounding an alert if programmed (660) and perhaps even start a duration countdown timer (661); reaching a set time; if a set time has not been reached, displaying an error, alarm, sound alert or the like (663), and perhaps even stopping a run (664); if a set time has been reached, proceeding to a next set point (665) which may include continuing onto step (655) or may turn on a cooling fan (666) and end heating control program to deactivate a heater (667); any combination thereof, and the like.

To comply with laboratory governing body operating regulations, such as CAP guidelines, embodiments of the present invention may include a quality control method for using the heating device in the flowchart in FIG. 15. In embodiments, a small container of heat sensitive pH indicating retrieval solution may be placed in a chamber. A biological specimen may be placed in the pH indicating retrieval solution. Alternatively, the specimen can be placed in a non-pH indicating retrieval solution, but the pH strip may be used instead.

As represented in FIG. 15, systems and methods may include, but are not limited to, placing specimens such as biological samples into slide containers (600); placing a pH solution into a slide container (601); placing a slide container into a sealable heating pressure chamber (602); checking and recording a color of a pH solution or even using a pH strip (603); placing a steam strip in a sealable heating pressure chamber (604); selecting protocol, a set time, a temperature or the like parameters for processing in a chamber (605); start a run such as by activating a heater (606); recording temperature and pressure for a duration of a run (607); open a chamber when it may be depressurized and perhaps safe (608); checking and recording a color of a pH solution or using a pH strip (609); checking and recording a color of a steam strip (610); printing a run report (611); any combination thereof; and the like.

Embodiments of the present invention may provide a user interface in conjunction with antigen retrieval device as may be understood individually or perhaps even sequentially from the examples in FIGS. 17-54. In one perspective, a non-keyboard-based interface system may be used for operation of antigen retrieval device. A user interface system may include software buttons perhaps through a touch screen LCD panel. Some if not all operation control of an antigen retrieval device may be controlled through software. This type of expert system may allow a user to choose the desired antibody and a system may automatically calculate and may even set reaction protocols including but not limited to the temperature, pressure, time, solution, combinations thereof, and the like protocols. Embodiments may include a system which visually tracks the current temperature and perhaps even pressure of the system during operation and may even provide an alarm option should a particular process need attention or provide user awareness or the like. It is noted that in embodiments, a control system such as a touch screen panel, computer, display or other device, may be directly connected or perhaps even indirectly connected to an antigen retrieval device. Indirect connections may include wireless communications, the Internet, through intermediary connections, or the like.

Figure 17:
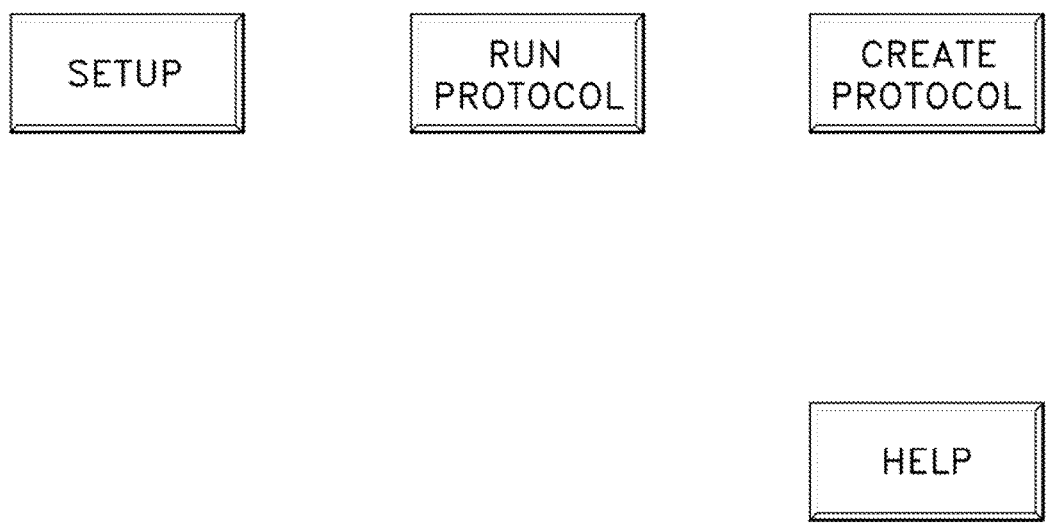
FIG. 17 is an example of an initial touch screen for a user interface system in accordance with embodiments of the present invention.
Figure 18:
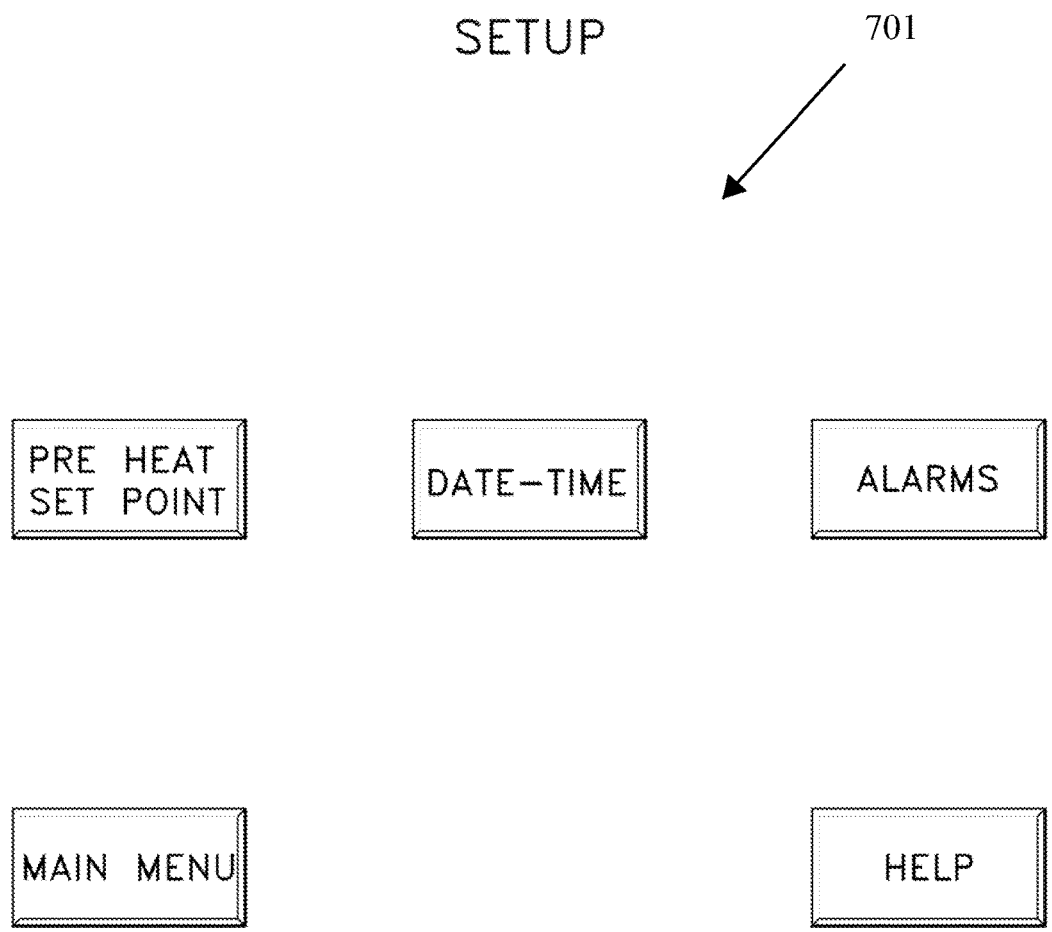
FIG. 18 is an example of a setup screen for a user interface system in accordance with embodiments of the present invention.
Figure 19:
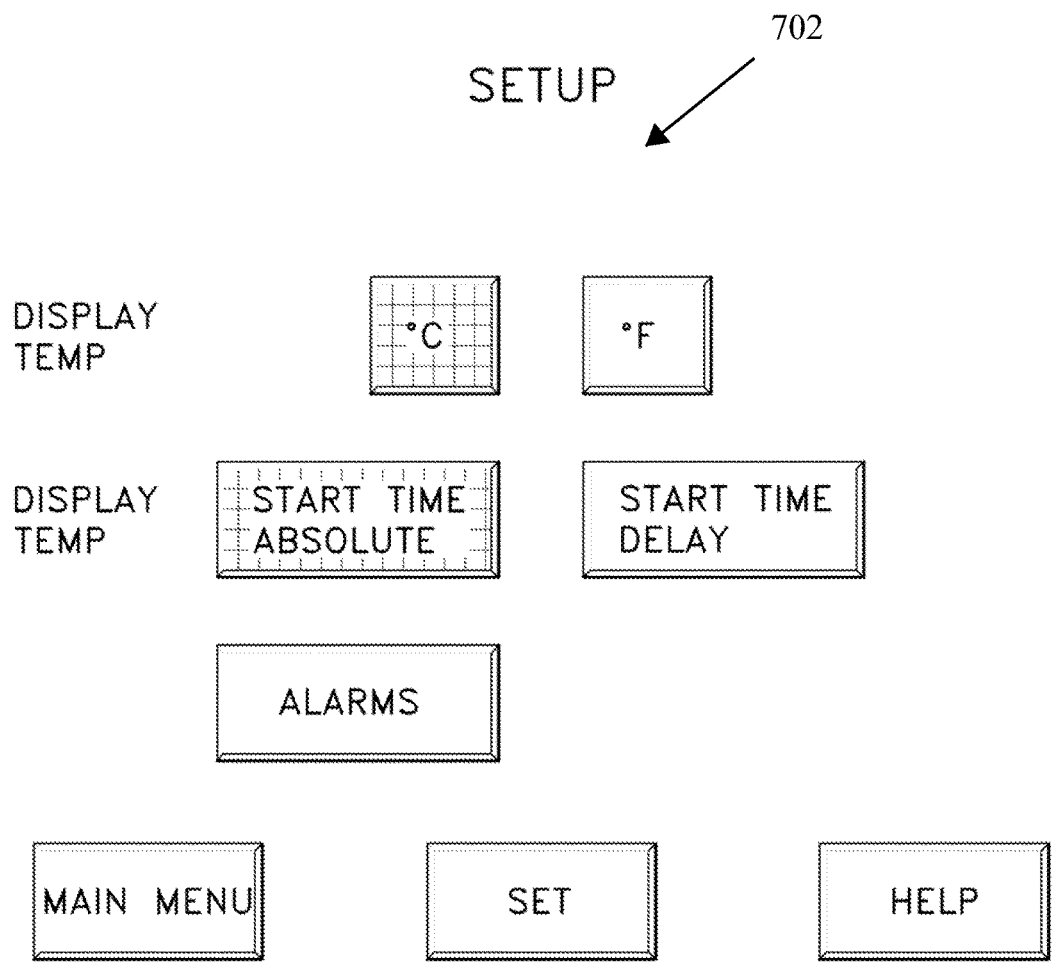
FIG. 19 is an example of an alternative setup screen for a user interface system in accordance with embodiments of the present invention.
Figure 20:
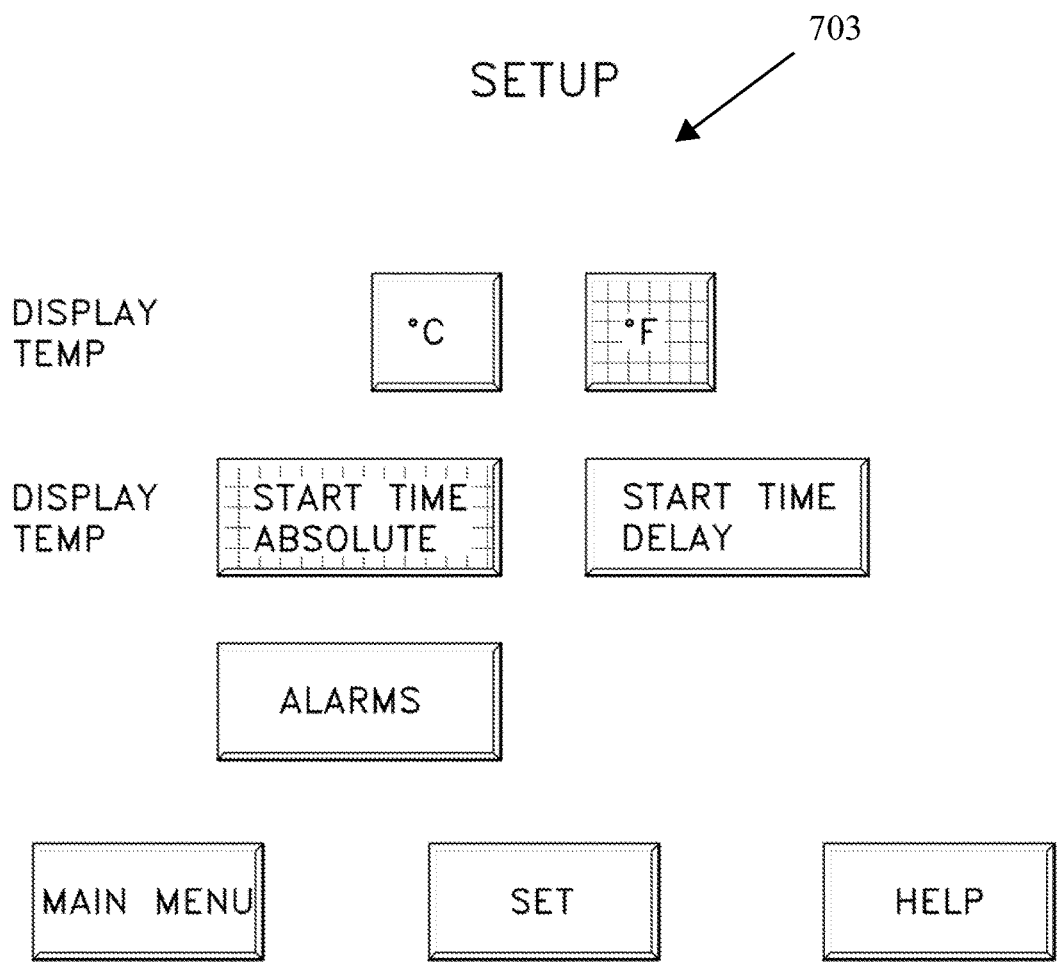
FIG. 20 is an example of an alternative setup screen for a user interface system in accordance with embodiments of the present invention.
Figure 21:
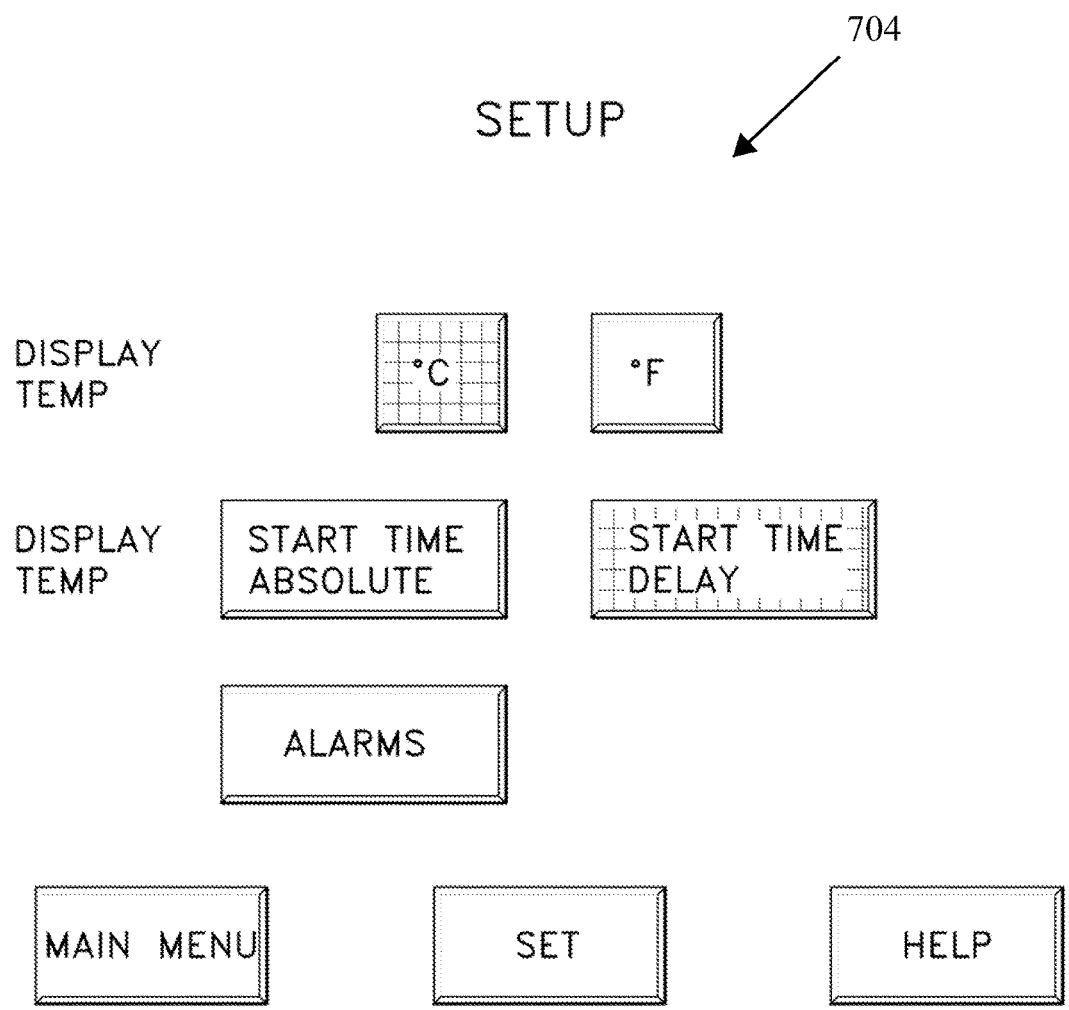
FIG. 21 is an example of an alternative setup screen for a user interface system in accordance with embodiments of the present invention.
Figure 22:
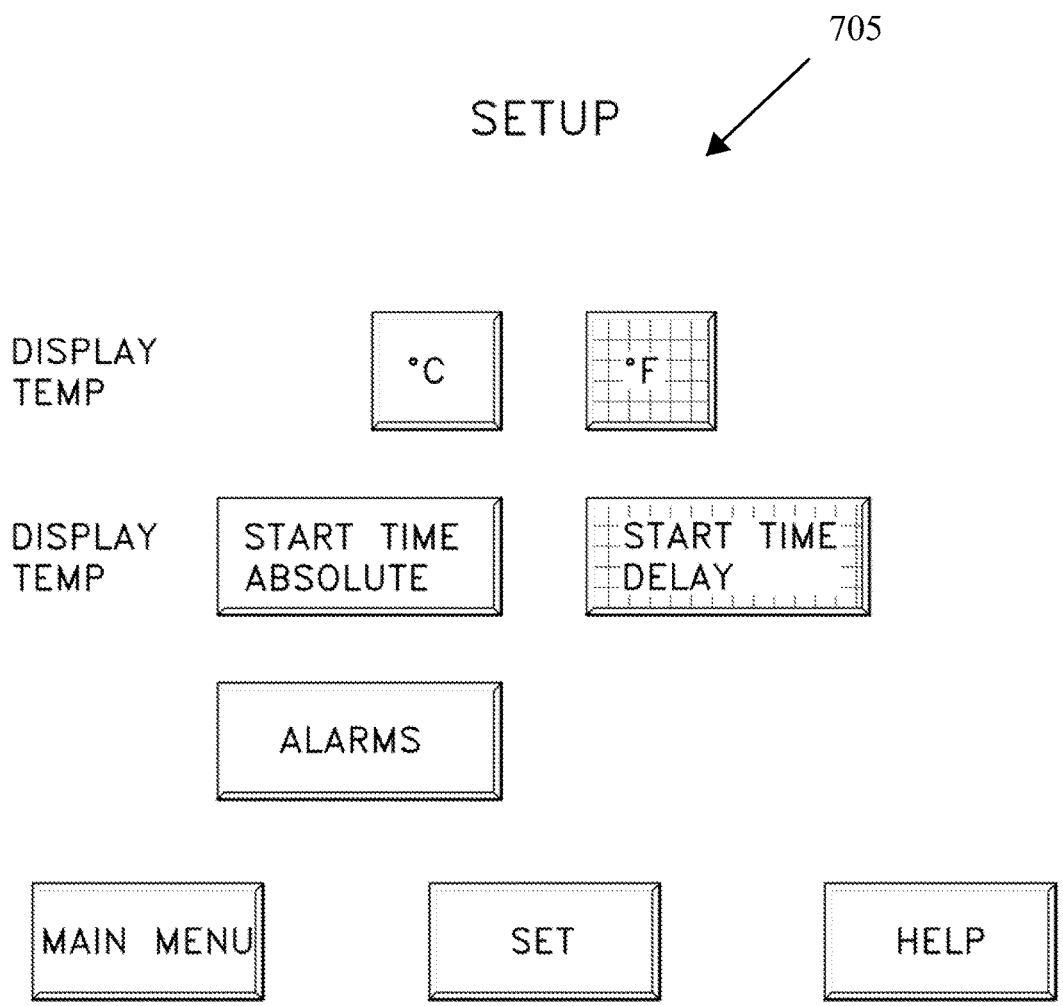
FIG. 22 is an example of an alternative setup screen for a user interface system in accordance with embodiments of the present invention.
Figure 23:
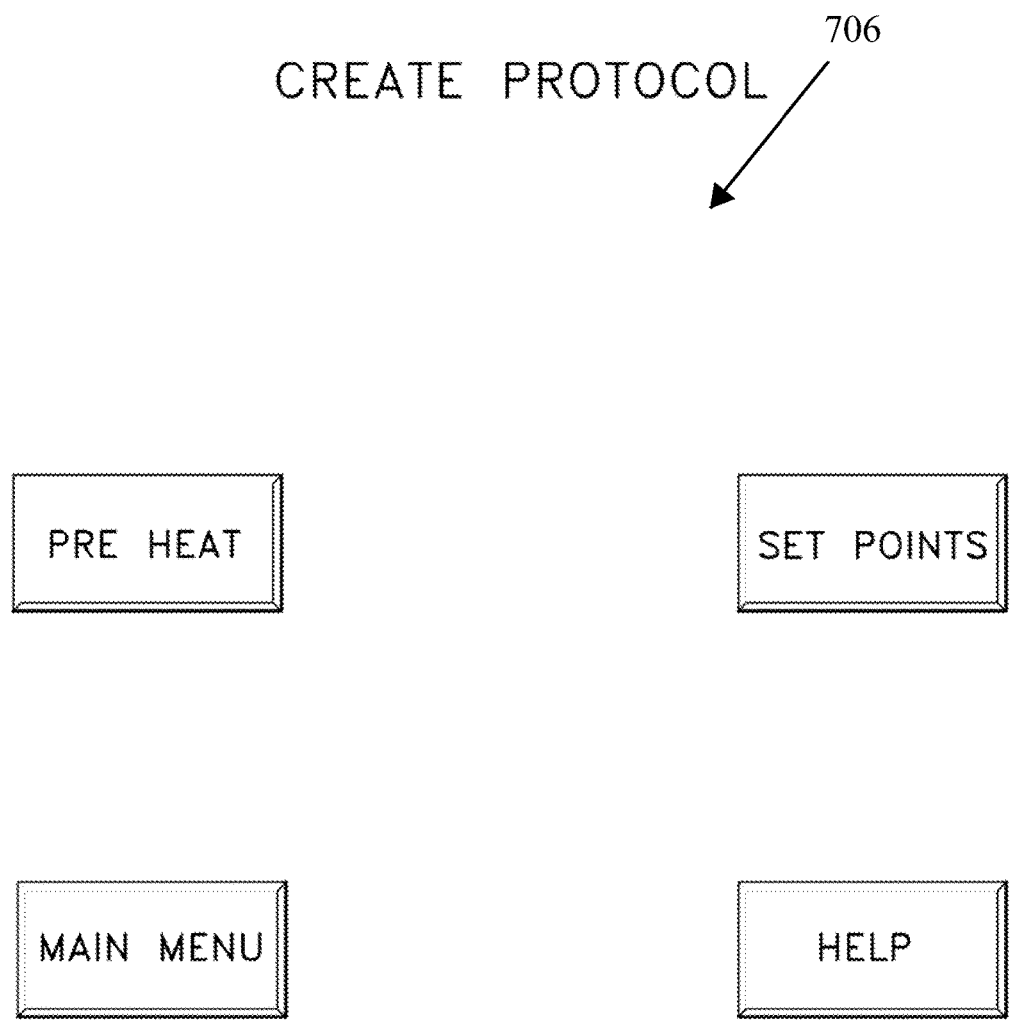
FIG. 23 as an example of a create protocol screen for a user interface system in accordance with embodiments of the present invention.
Figure 24:
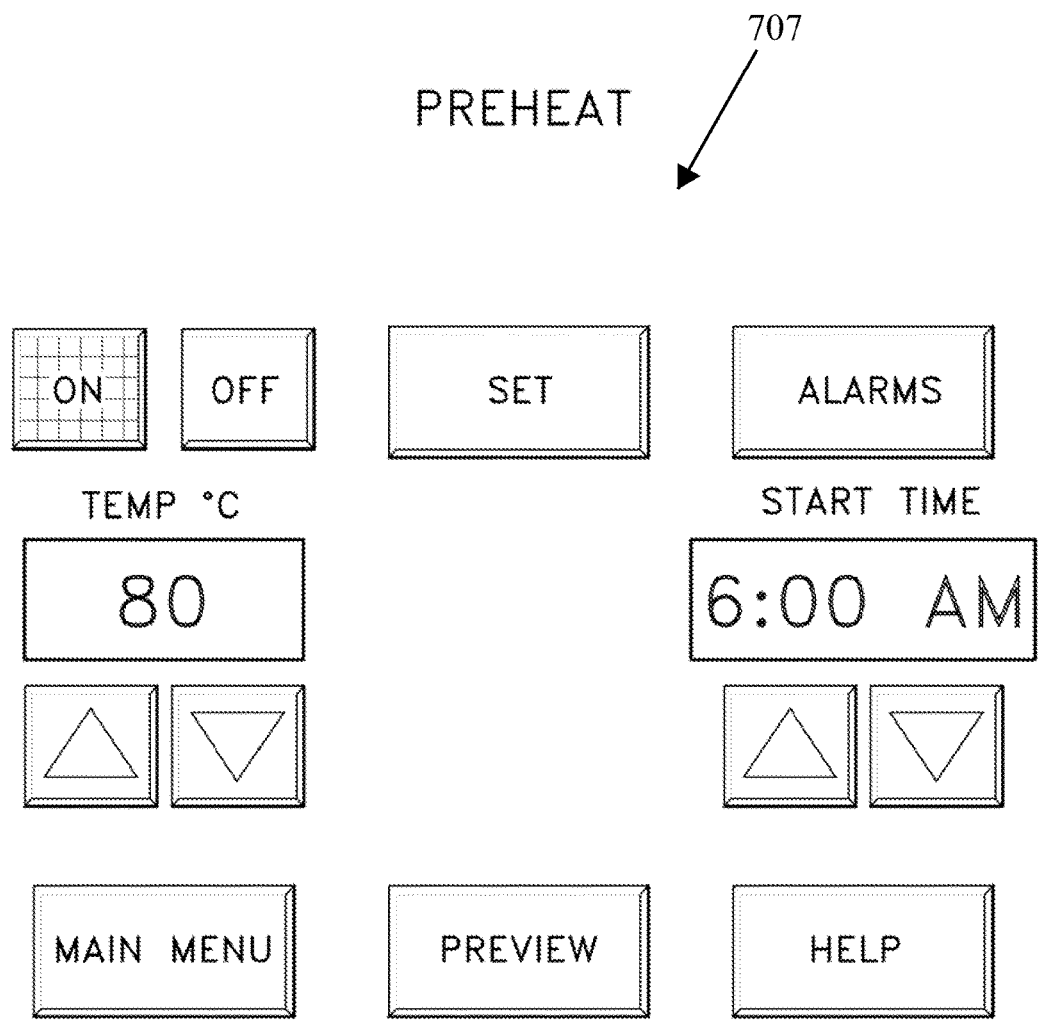
FIG. 24 is an example of a preheat screen for a user interface system in accordance with embodiments of the present invention.
Figure 25:
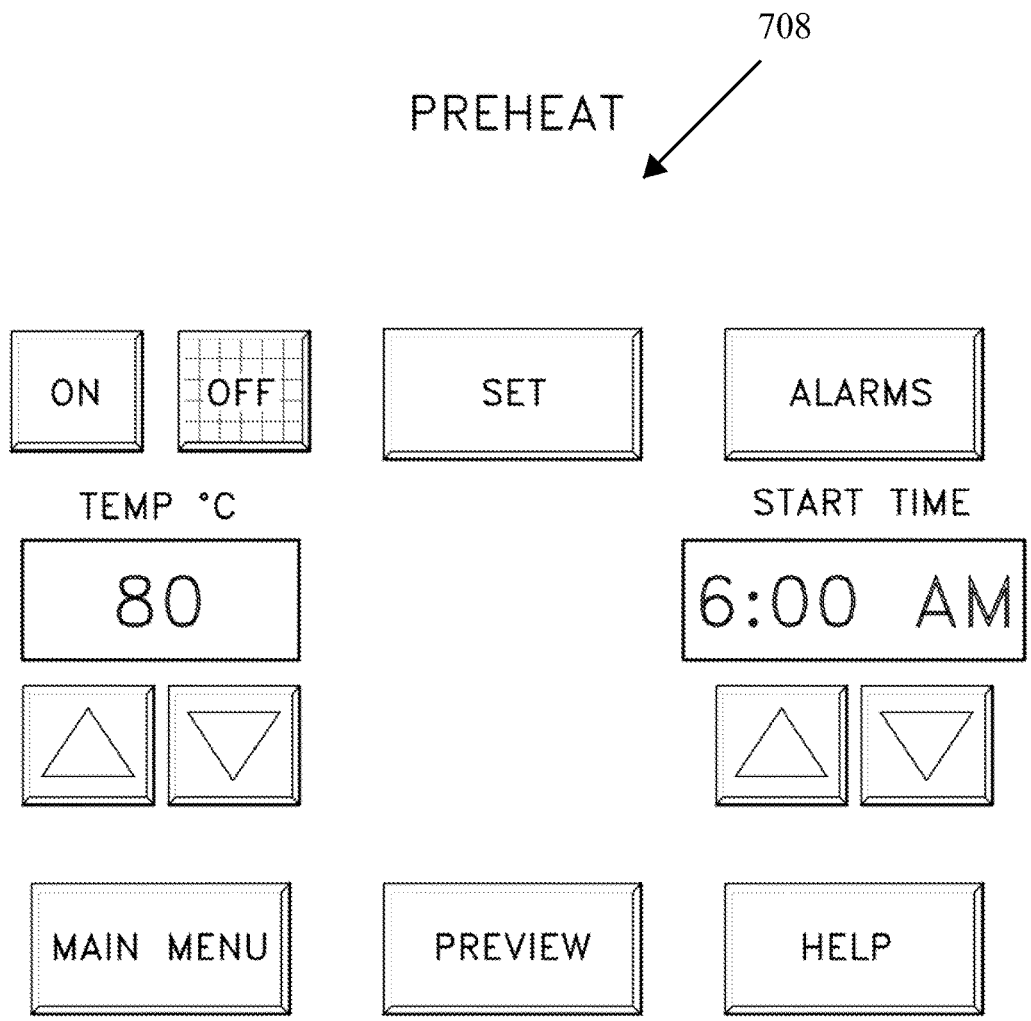
FIG. 25 is an example of an alternative preheat screen for a user interface system in accordance with embodiments of the present invention.
Figure 26:
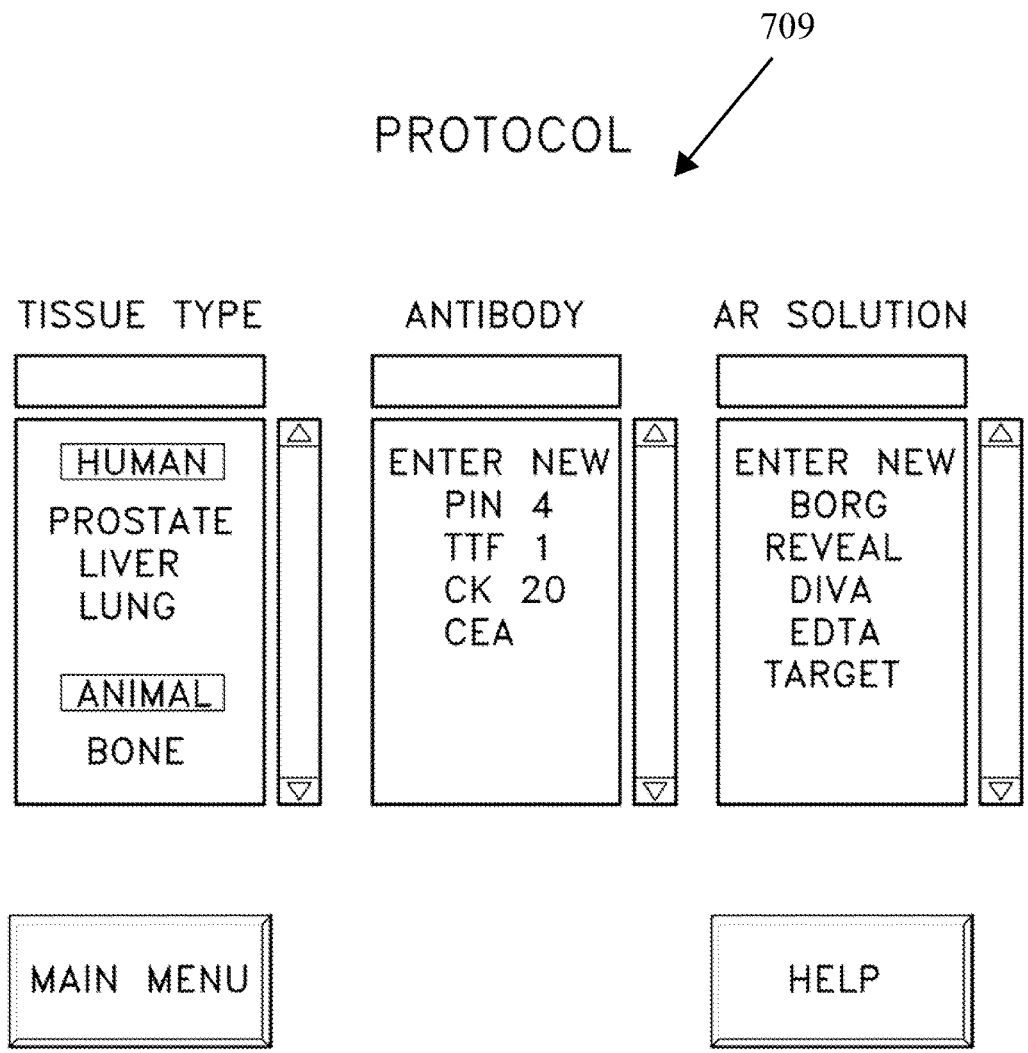
FIG. 26 is an example of a protocol screen for a user interface system in accordance with embodiments of the present invention.

As mentioned, embodiments of the present invention may provide an interface system in which a user may utilize in setting up and starting a sealable heating pressure chamber system. Interactions with a controller, a process controller, a programmable process controller, automatic antigen retrieving process controller and even a processor of a sealable heating pressure chamber system may include a touch screen, a pen-activated screen, a keyboard entry, a mouse entry, voice activation, any combination thereof, and the like. FIG. 17 shows an example of an initial screen (700) which may be provided on a display of a chamber system, including but not limited to, a setup, run protocol, create protocol, and help options. A starter element (801) may be a run protocol screen, a start button, a user-activated start, or the like. FIG. 18 shows an example of a setup screen (701) which may be provided on a display of a chamber system, including but not limited to, a pre heat set point, a date-time, alarms, main menu, and help options. FIG. 19 shows an example of a set up screen (702) where a display temperature may be selected in degrees Celsius or degrees Fahrenheit, a display temperature may be selected as a start time absolute or start time delay, alarms may be selected, in addition to a main menu, a set, and perhaps even a help option available for selection as a user may navigate through controller options. FIG. 19 shows that a display temperature in degrees Celsius and a display temperature in start time absolute have been selected by a user (702). FIG. 20 shows that a display temperature in degrees Fahrenheit and a display temperature in start time absolute have been selected by a user (703). FIG. 21 shows that a display temperature in degrees Celsius and a display temperature in start time delay have been selected by a user (704). FIG. 22 shows that a display temperature in degrees Fahrenheit and a display temperature in start time delay have been selected by a user (705). FIG. 23 shows an example of a create protocol screen (706) providing preheat, set points, main menu, and help options. FIG. 24 shows an example of a preheat screen (707) providing on, off, set, alarms, temperature setting, temperature up, temperature down, start time setting, start time up, start time down, main menu, preview, and help options. In FIG. 24, an "on" selection has been made by a user in a preheat screen. In FIG. 25, an "off" selection has been made by a user in a preheat screen (708). An example of a protocol screen (709) is shown in FIG. 26 where tissue type, antibody type, antigen retrieval solution type may be selected from a list of options to provide a user-selected protocol (804) as well as providing a main menu and help option.

Of course, many different types of protocol may be available with an antigen retrieval system including, but not limited to, user-selected protocol, pre-heating protocol, a temperature setting, pressure setting, a pre-programmed protocol, a newly created protocol, an alarm protocol, a tissue type, an antibody type, an antigen retrieval solution, a ramp, a soak, a high temperature protocol, a low temperature protocol, a pre-start checklist, a delay start time, processing protocol, a special protocol timing; a special protocol solution; a protocol utilizing a heat retrieval solution as a retrieval buffer; a protocol utilizing a citrate buffer as a retrieval buffer; a protocol utilizing EDTA as retrieval buffer; a protocol utilizing a Tris buffer as a retrieval buffer; a protocol utilizing a retrieval buffer in combination with a digestion; a protocol designed for over-fixed tissues; a protocol utilizing a retrieval buffer in combination with a light enzyme digestion; a protocol designed for a specific antibody; a protocol designed for a specific antibody-antigen combination; a protocol utilizing overnight incubation; a protocol utilizing overnight incubation with a citrate buffer; a protocol utilizing overnight incubation with a Tris buffer; a protocol utilizing overnight incubation at about 4 degrees Celsius; a protocol utilizing special enzyme procedures; a protocol utilizing trypsin for retrieval of keratin AE1/AE3; a protocol utilizing a high molecular weight cytokeratin antibody; a protocol utilizing a high molecular weight cytokeratin antibody for basal cells; a protocol utilizing a high molecular weight cytokeratin antibody for prostate samples; a protocol utilizing a high Tris pH buffer retrieval solution followed by about a one minute digestion; a protocol designed without substantially any regard to a fixation time; a protocol utilizing a temperature between about 75 degrees Celsius and about 80 degrees Celsius; a protocol designed for simultaneously processing multiple varying biological samples; a protocol utilizing a temperature between about 75 degrees Celsius and about 80 degrees Celsius with an incubation time between about 12 hours and about 16 hours; a protocol designed to adapt morphology at a temperature of about 95 degrees Celsius for between about 45 and about 60 minutes of steaming, any combination thereof, and the like.

Figure 27:
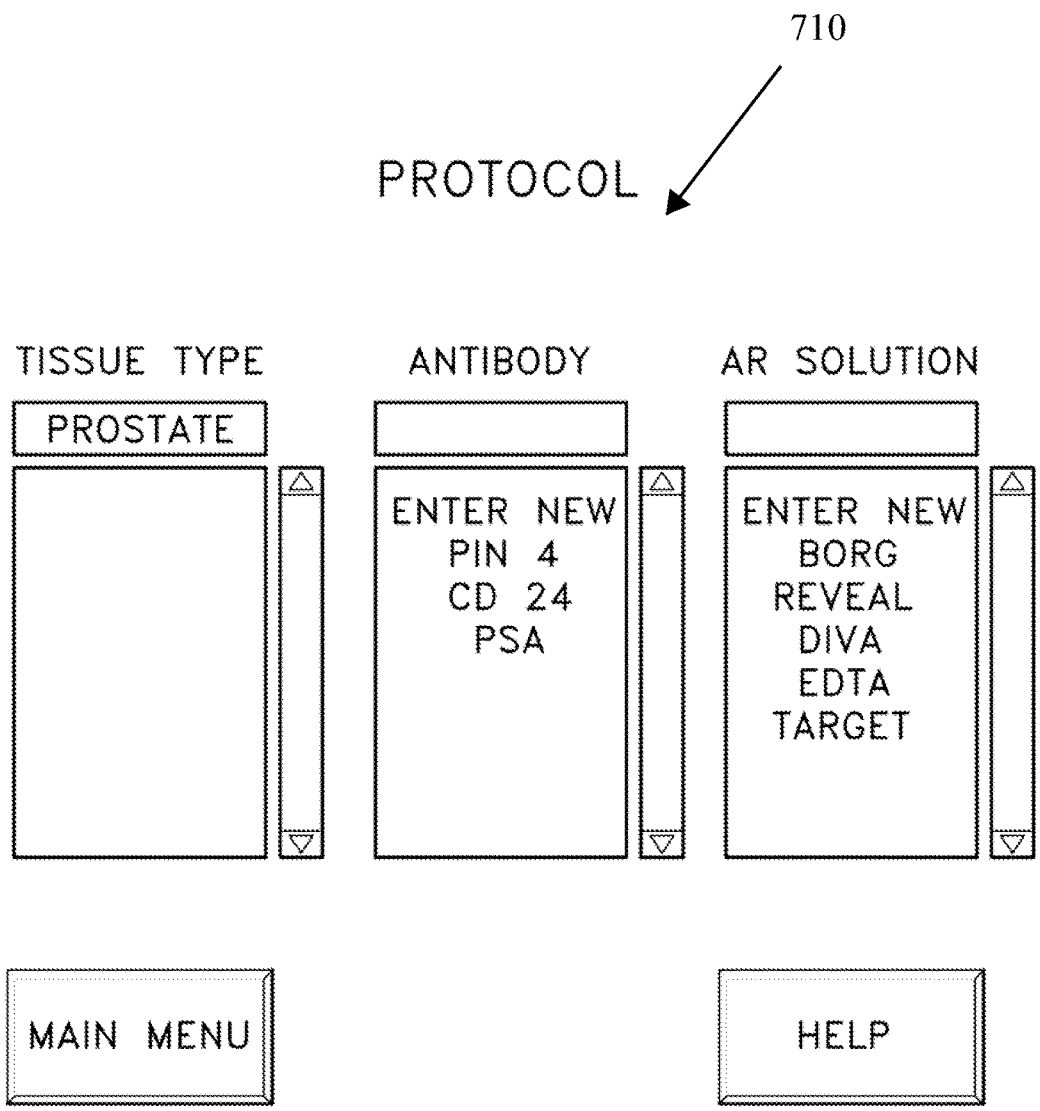
FIG. 27 is an example of an alternative protocol screen for a user interface system in accordance with embodiments of the present invention.
Figure 28:
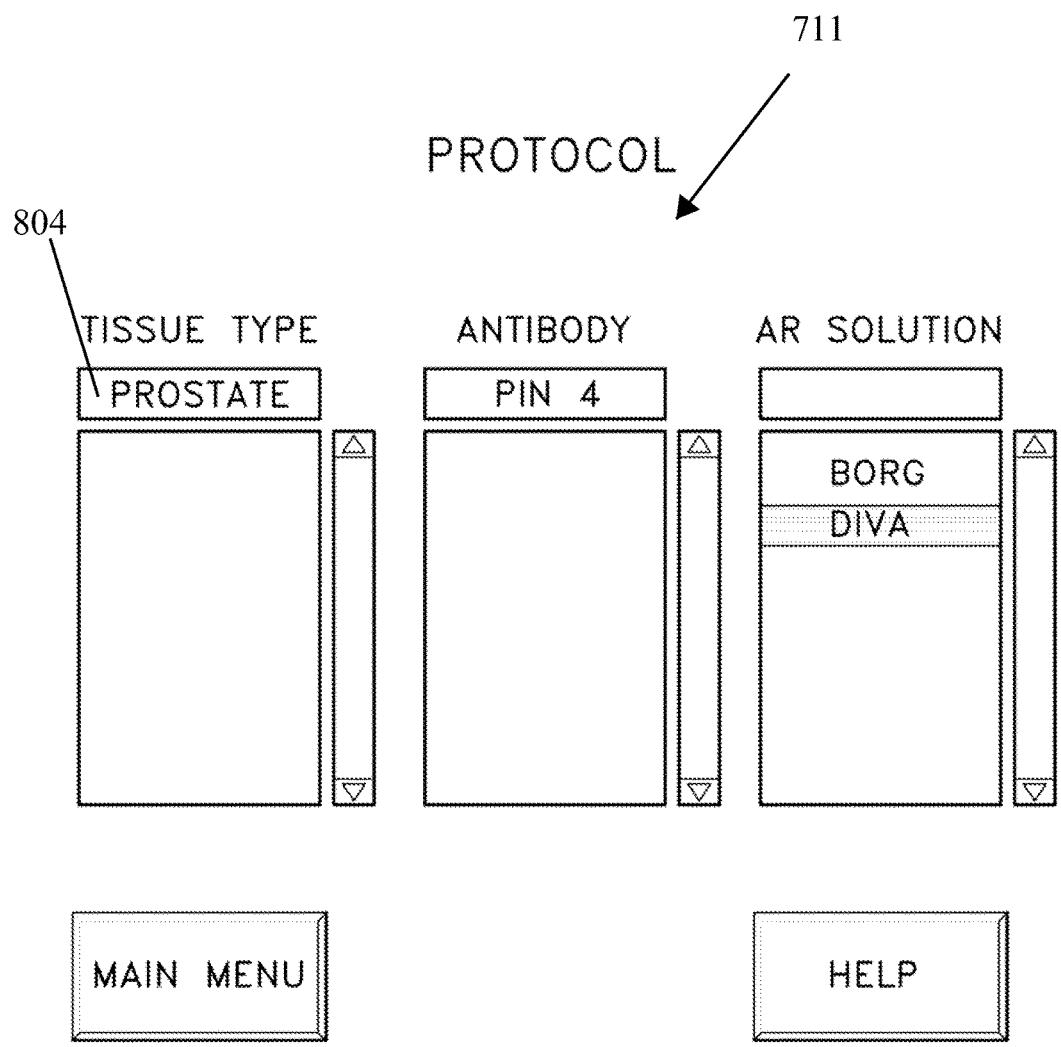
FIG. 28 is an example of an alternative protocol screen for a user interface system in accordance with embodiments of the present invention.
Figure 29:
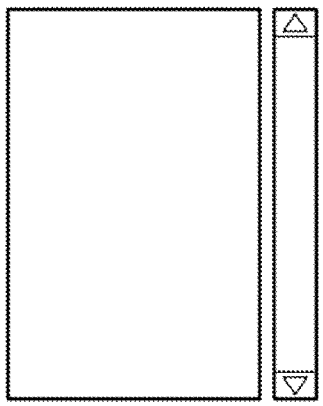
FIG. 29 is an example of an alternative protocol screen for a user interface system in accordance with embodiments of the present invention.
Figure 29:
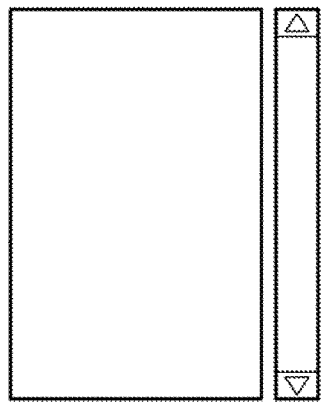
Figure 29:
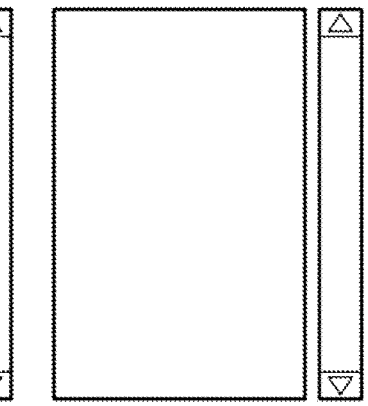
Figure 29:
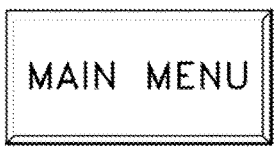
Figure 29:
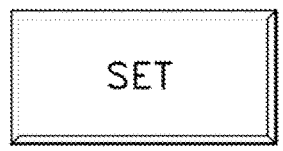
Figure 29:
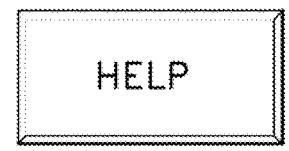
Figure 30:
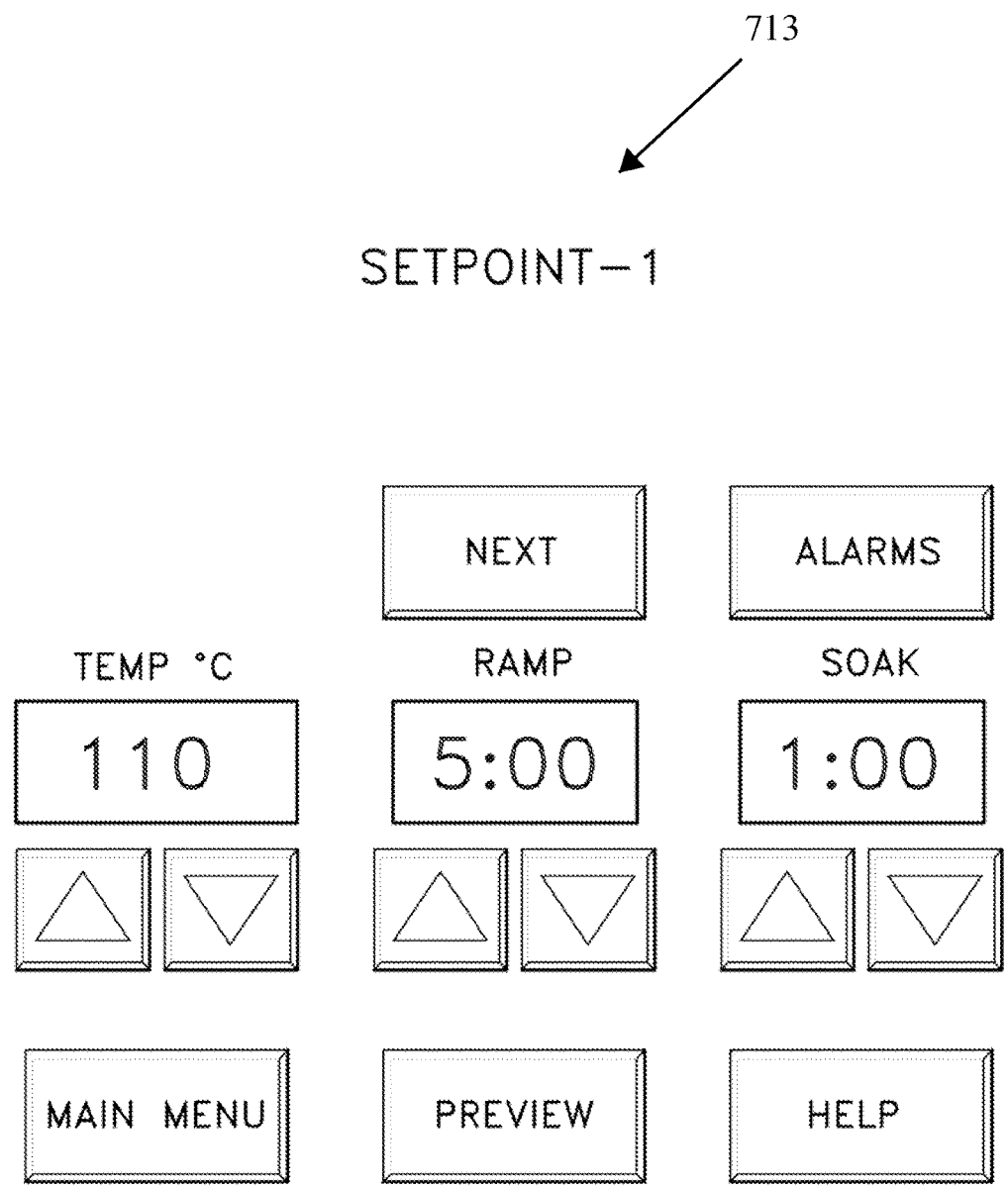
FIG. 30 is an example of a first set point screen for a user interface system in accordance with embodiments of the present invention.
Figure 31:
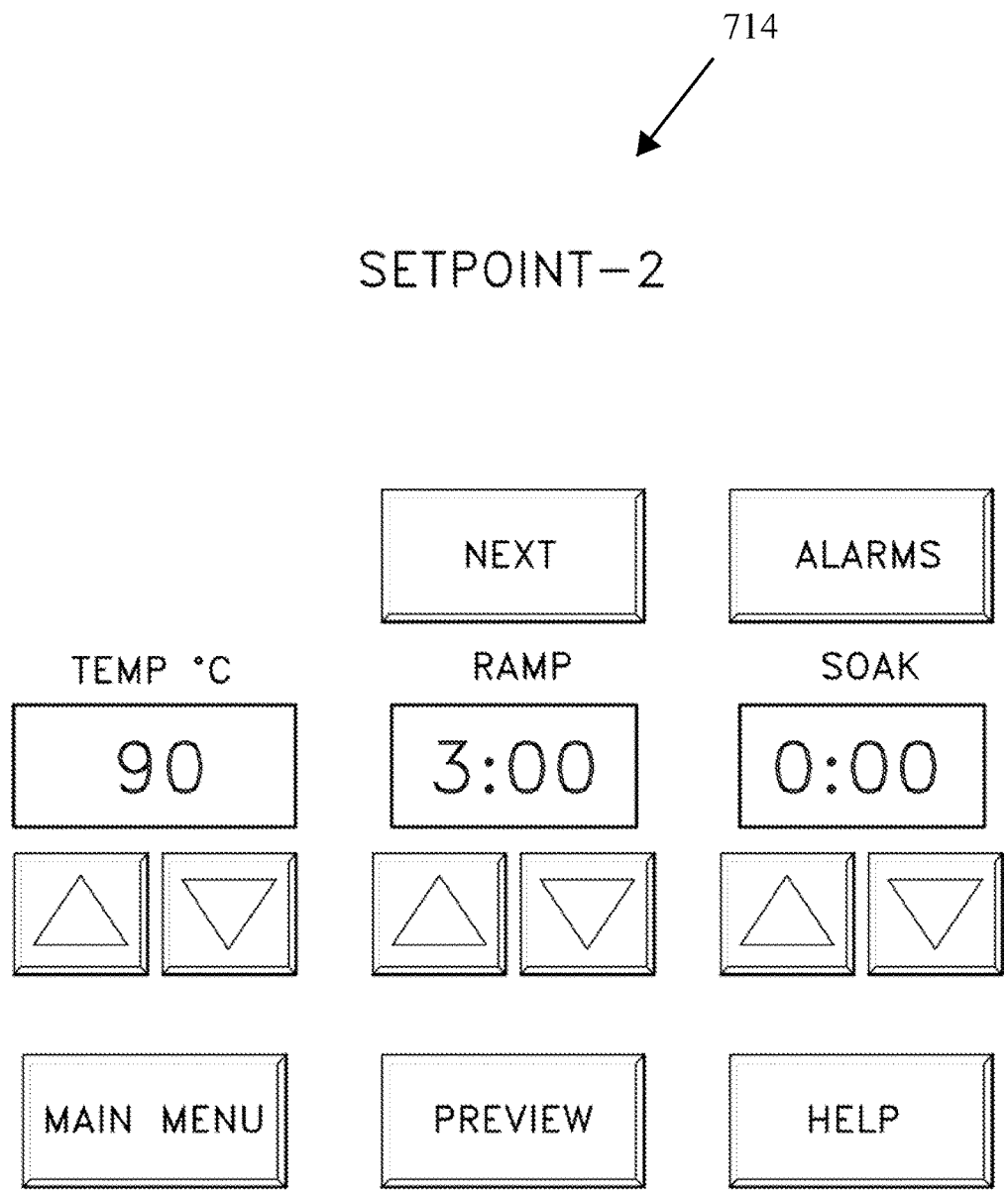
FIG. 31 is an example of a second set point screen for a user interface system in accordance with embodiments of the present invention.
Figure 32:
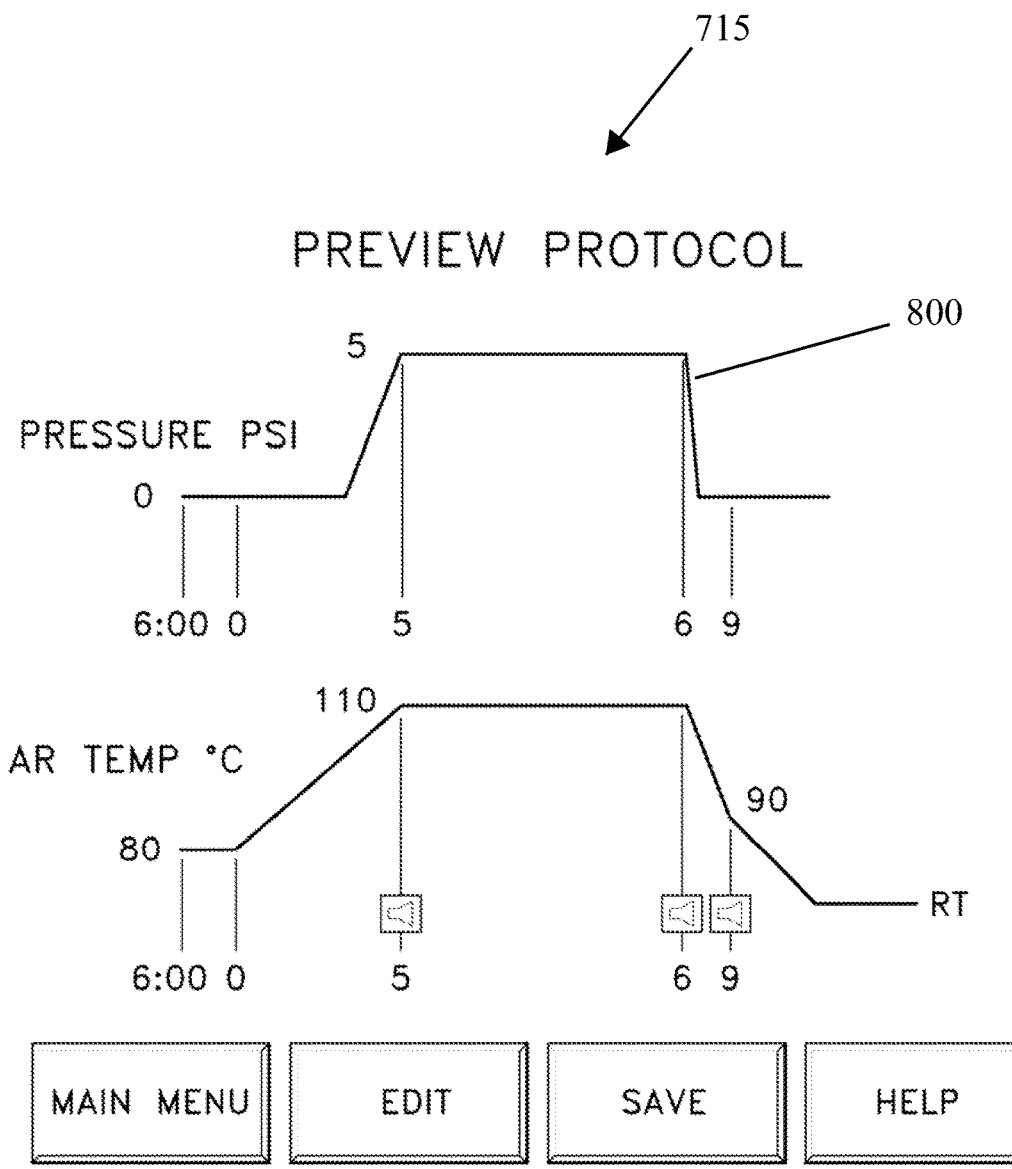
FIG. 32 is an example of a preview protocol screen for a user interface system in accordance with embodiments of the present invention.
Figure 33:
FIG. 33 is an example of an alternative protocol screen for a user interface system in accordance with embodiments of the present invention.
Figure 34:
FIG. 34 is an example of an alternative protocol screen for a user interface system in accordance with embodiments of the present invention.
Figure 35:
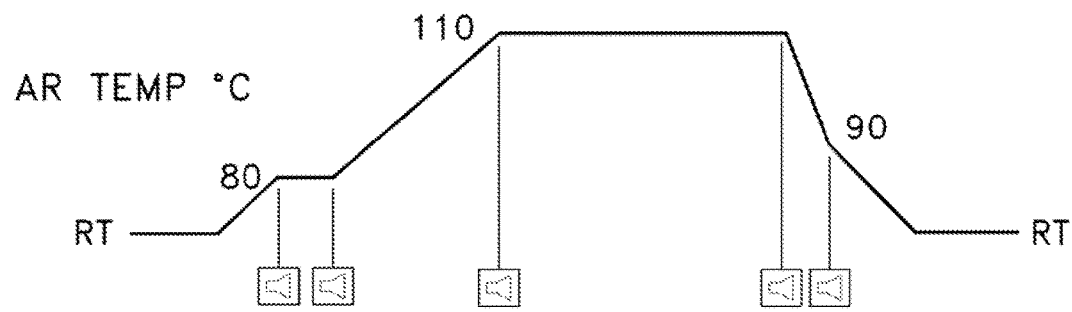
FIG. 35 is an example of a high temp screen showing preheat on for a user interface system in accordance with embodiments of the present invention.
Figure 36:
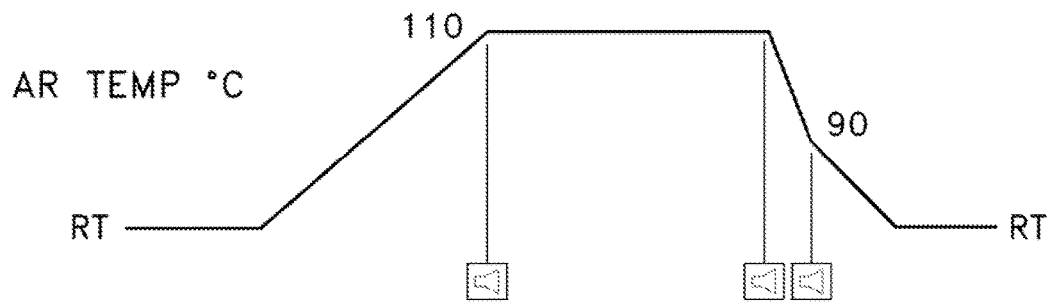
FIG. 36 is an example of a high temp screen showing preheat off for a user interface system in accordance with embodiments of the present invention.
Figure 37:
FIG. 37 is an example of a high temp screen with a checklist for a user interface system in accordance with embodiments of the present invention.
Figure 37:
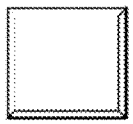
Figure 37:
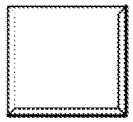
Figure 37:
Figure 37:
Figure 38:
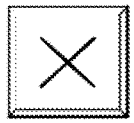
FIG. 38 is an example of an alternative high temp screen with a checklist for a user interface system in accordance with embodiments of the present invention.
Figure 38:
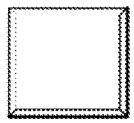
Figure 38:
Figure 38:
Figure 39:
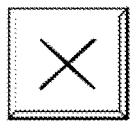
FIG. 39 is an example of an alternative high temp screen with a checklist for a user interface system in accordance with embodiments of the present invention.
Figure 39:
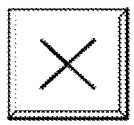

FIG. 27 shows an example of a protocol screen (710) where a prostate tissue has been selected by a user from the tissue type options, including but not limited to human, prostate, liver, lung, animal, bone, and the like. FIG. 28 shows an example of a protocol screen (711) where a PIN 4 antibody has been selected by a user from the antibody options, including but not limited to, enter new, PIN 4, TIF1, CK 20, CEA, and the like. FIG. 29 shows an example of protocol screen (712) where a DIVA antigen retrieval solution selected by a user from the AR solution options, including but not limited to, enter new, BORG, REVEAL, DIVA, EDTA, TARGET, and the like. FIG. 30 shows an example of a first setpoint screen (713) where a temperature may be displayed and may be increased or decreased, a ramp time may be displayed and may be increased or decreased, a soak time may be displayed and may be increased or decreased, as well as providing next, alarms, main menu, preview, and help options. FIG. 31 shows an example of a second setpoint screen (714) perhaps similar to a first setpoint screen. FIG. 32 shows an example of a preview protocol screen (715) where a graphic representation of a pressure for at least one processing program run (800) may be visually displayed; a graphic representation of a temperature for at least one processing run may be visually displayed, along with alarms; as well as providing main menu, edit, save, and help options. FIG. 33 shows an example of a protocol screen (716) where protocol options may include a high temperature, low temperature, user protocol animal 1, or the like for user selection as well as providing a main menu and help options. Additional protocol options which may be found in a protocol screen (716) may include low pressure protocol, high pressure protocol, and the like. FIG. 34 shows an example of a protocol screen (717) where high temperature protocol has been selected by a user. FIG. 35 shows an example of a high temperature screen (718) where a graphic representation of a temperature for at least one processing run along with alarms may be displayed, providing that pre heat has been selected "on", and also providing a main menu, next, and help options. FIG. 36 shows an example of a high temperature screen (719) similar to FIG. 35 providing that a pre heat has been selected "off". FIG. 37 shows an example of checklist screen (720) showing an example of a user checklist for a high temperature protocol which may prompt a user to review a checklist such as to ensure that water has been added to a chamber or that containers have been loaded perhaps with antigen retrieval solution or water along with main menu and help options. A checklist may include any type of element for to check perhaps before a processing run such as, but not limited to, temperature setting, pressure setting, pH setting; parameter setting; fluid level; correct fluid, correctly loaded slides, and the like. FIG. 38 shows an example of a checklist screen (721) for a high temperature protocol where a user has selected that they have filled a chamber with 100 mL of distilled water. FIG. 39 shows an example of a checklist screen (722) for a high temperature protocol where a user has selected that they have loaded containers and solution into a chamber.

Figure 41:
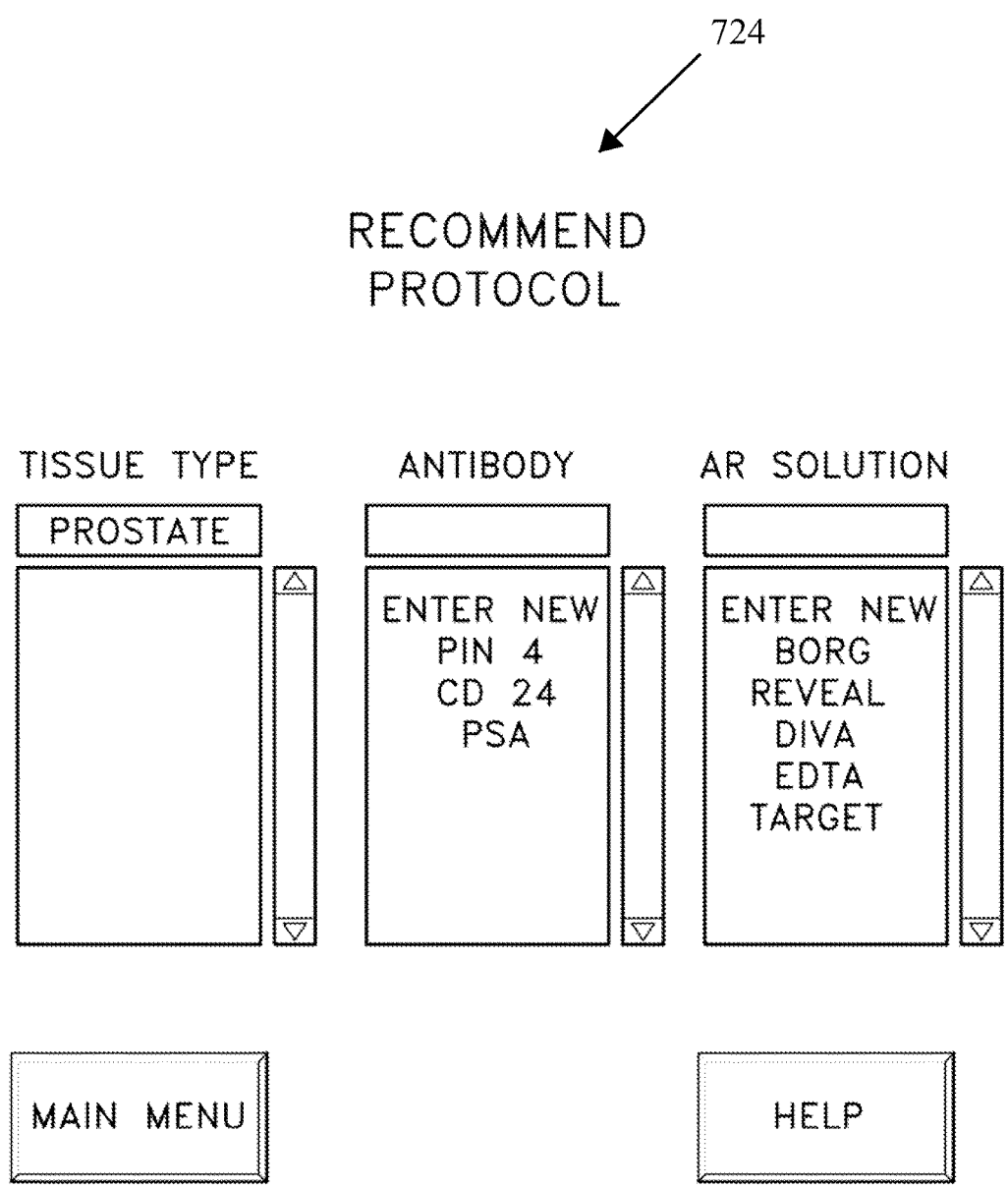
FIG. 41 is an example of an alternative recommended protocol screen for a user interface system in accordance with embodiments of the present invention.
Figure 43:
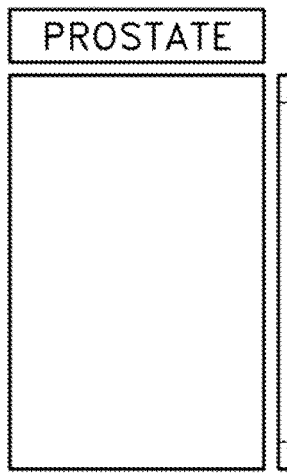
FIG. 43 is an example of an alternative recommended protocol screen for a user interface system in accordance with embodiments of the present invention.
Figure 43:
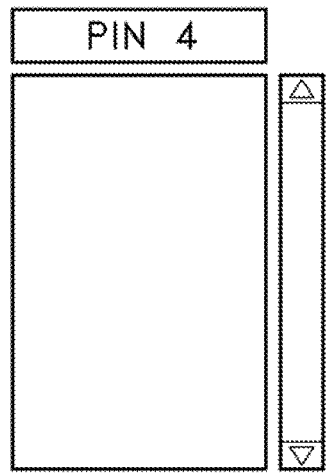
Figure 43:
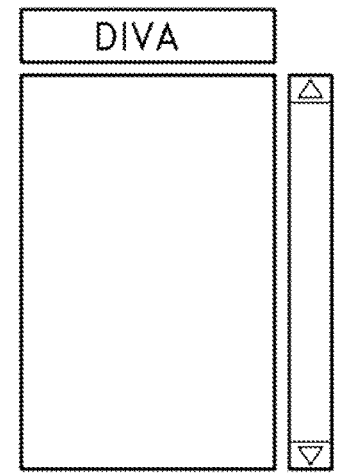
Figure 43:
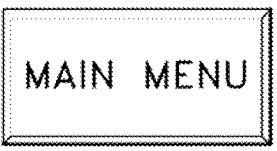
Figure 43:
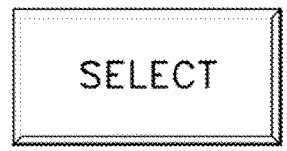
Figure 43:
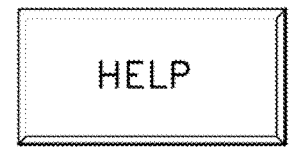
Figure 44:
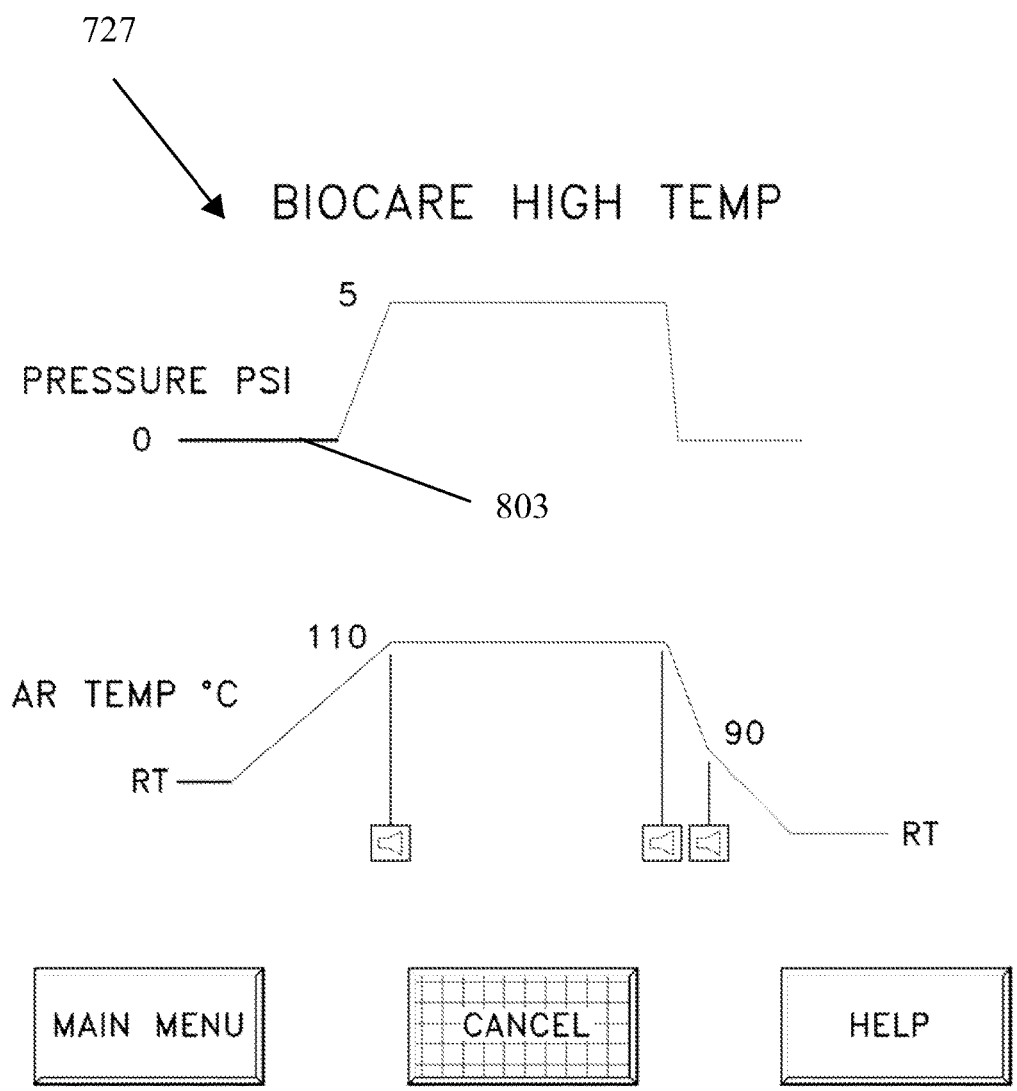
FIG. 44 is an example of a high temp screen tracking the pressure and temperature of a system for a user interface system in accordance with embodiments of the present invention.
Figure 45:
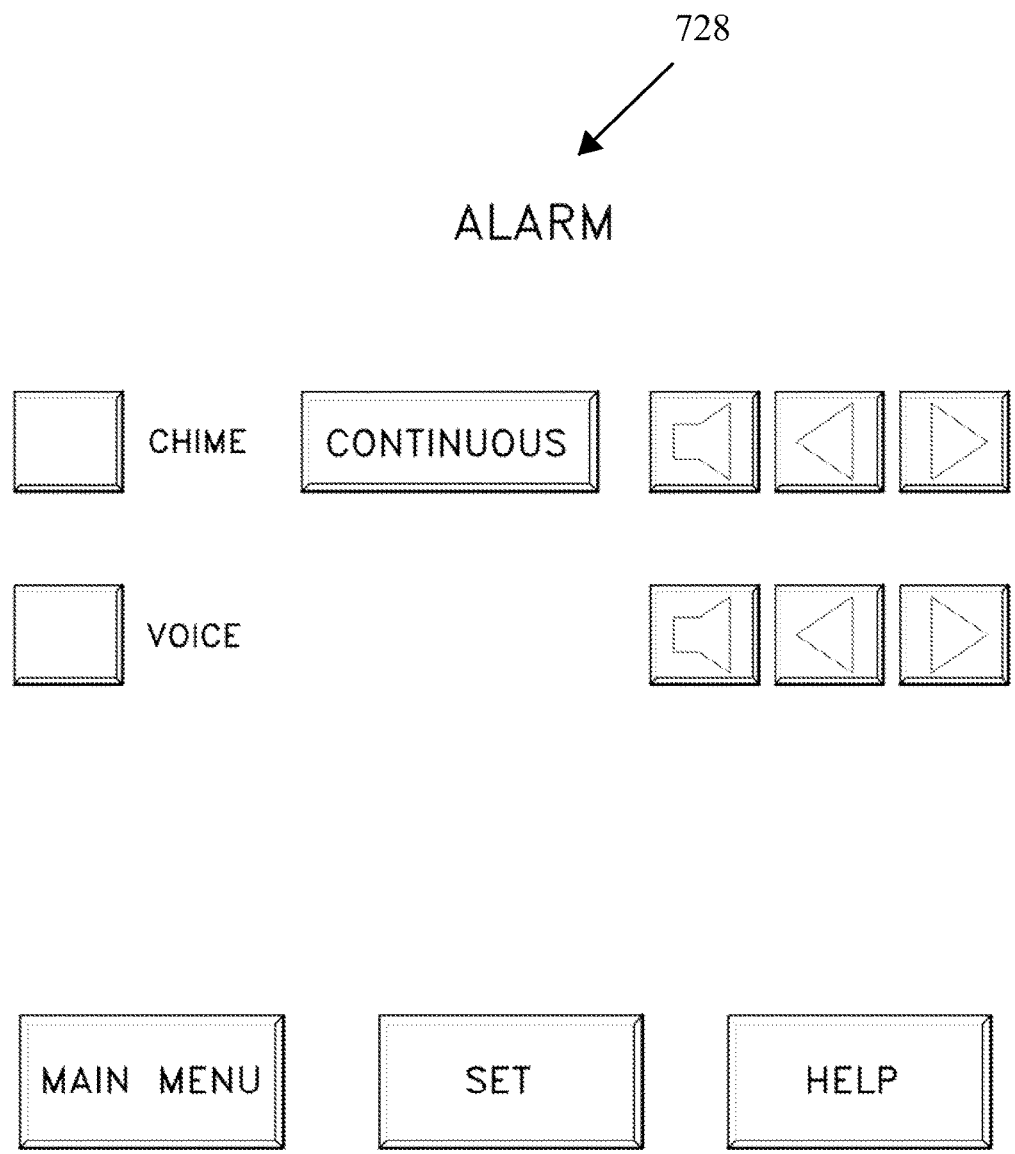
FIG. 45 is an example of an alarm screen for a user interface system in accordance with embodiments of the present invention.
Figure 46:
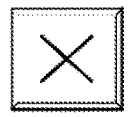
FIG. 46 is an example of an alternative alarm screen for a user interface system in accordance with embodiments of the present invention.
Figure 46:
Figure 46:
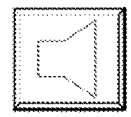
Figure 46:
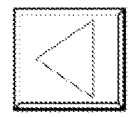
Figure 46:
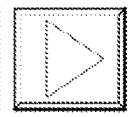
Figure 46:
Figure 46:
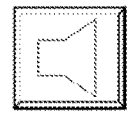
Figure 46:
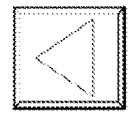
Figure 46:
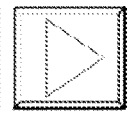
Figure 46:
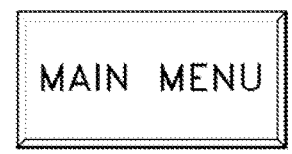
Figure 46:
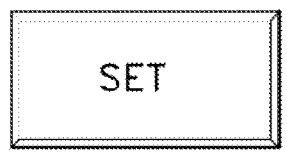
Figure 46:
Figure 47:
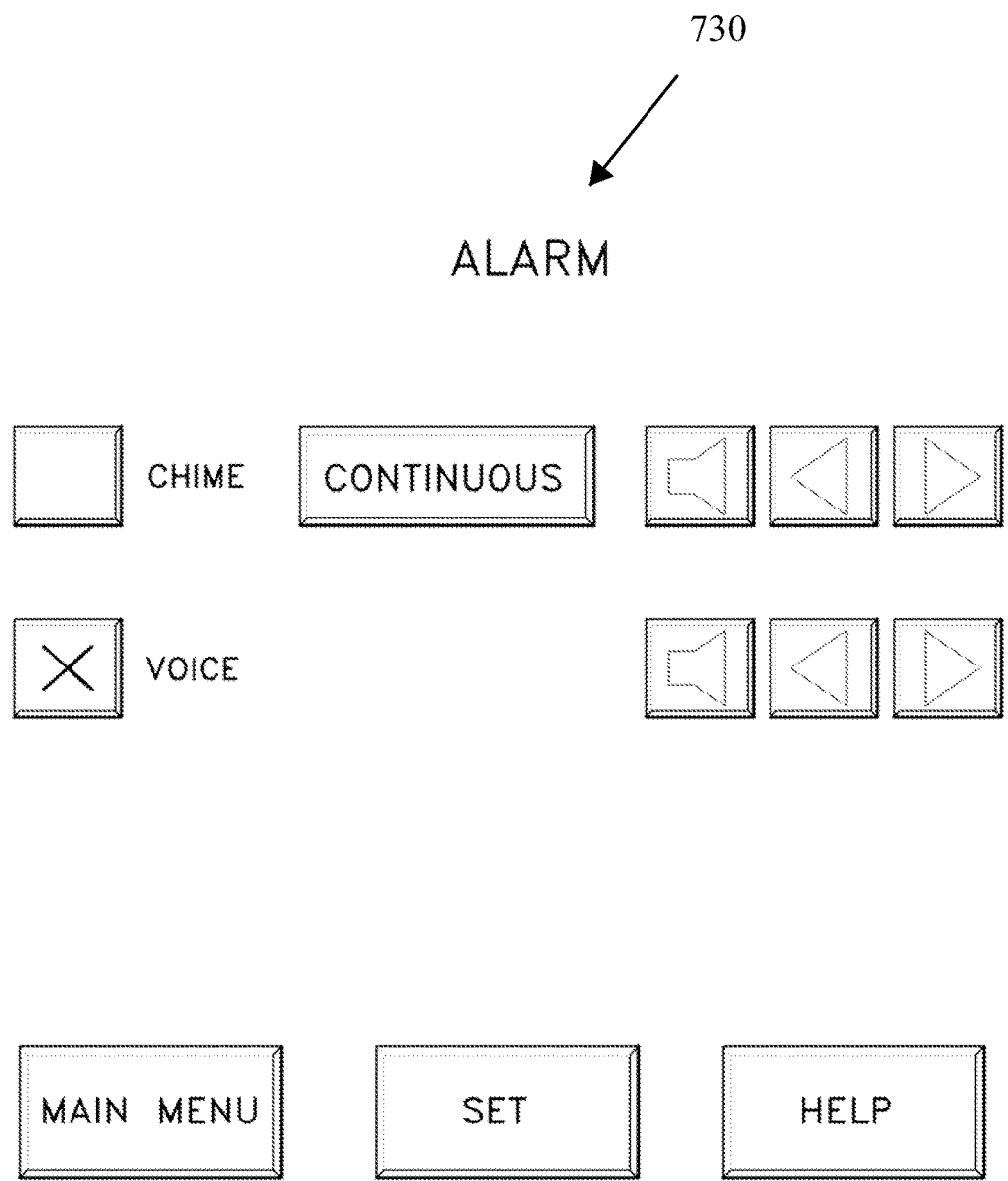
FIG. 47 is an example of an alternative alarm screen for a user interface system in accordance with embodiments of the present invention.
Figure 48:
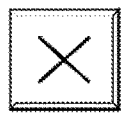
FIG. 48 is an example of an alternative alarm screen for a user interface system in accordance with embodiments of the present invention.
Figure 48:
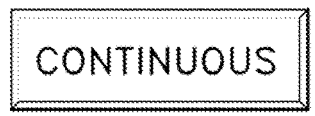
Figure 48:
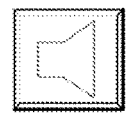
Figure 48:
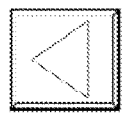
Figure 48:
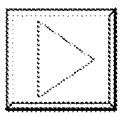
Figure 48:
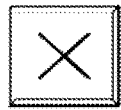
Figure 48:
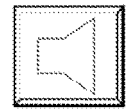
Figure 48:
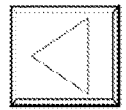
Figure 48:
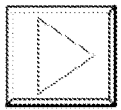
Figure 48:
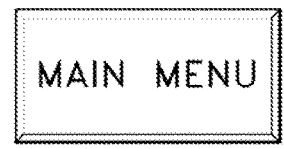
Figure 48:
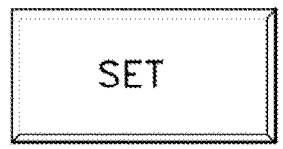
Figure 48:
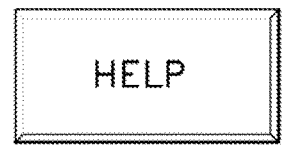
Figure 49:
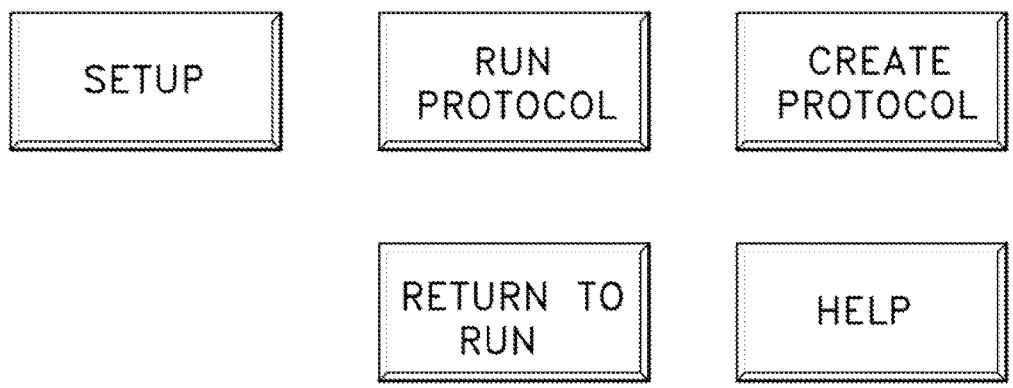
FIG. 49 is an example of an intermediary screen for a user interface system in accordance with embodiments of the present invention.
Figure 50:
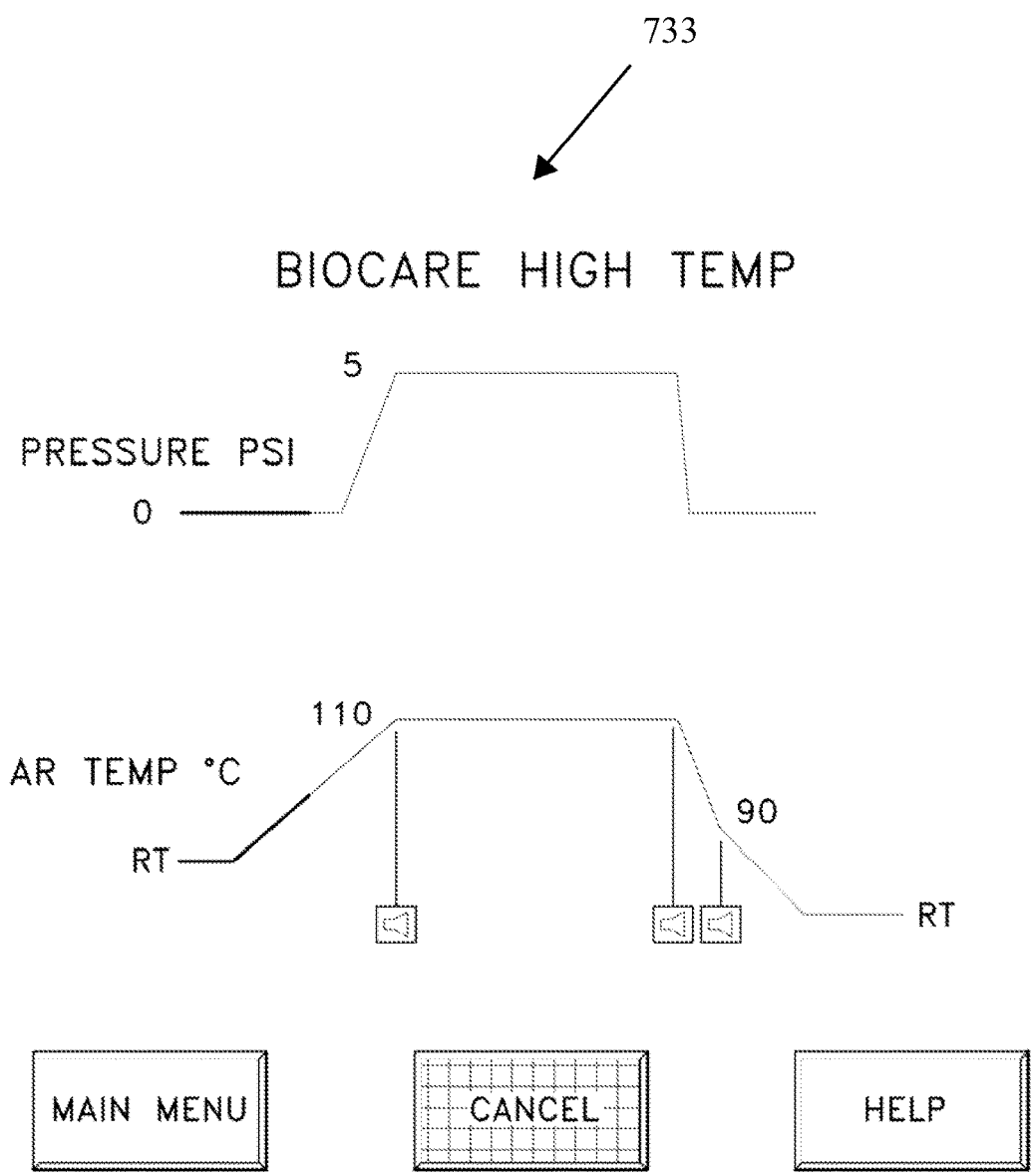
FIG. 50 is an alternative example of a high temp screen for a user interface system in accordance with embodiments of the present invention.
Figure 51:
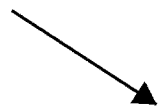
FIG. 51 is an example of a notification to cancel screen for a user interface system in accordance with embodiments of the present invention.
Figure 51:
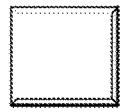
Figure 51:
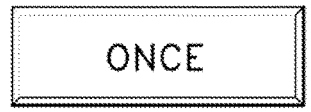
Figure 51:
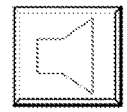
Figure 51:
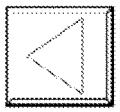
Figure 51:
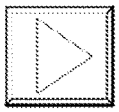
Figure 51:
Figure 51:
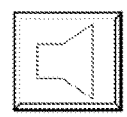
Figure 51:
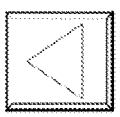
Figure 51:
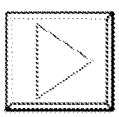
Figure 51:
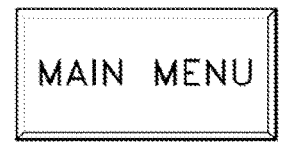
Figure 51:
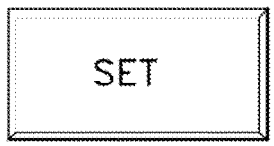
Figure 51:
Figure 52:
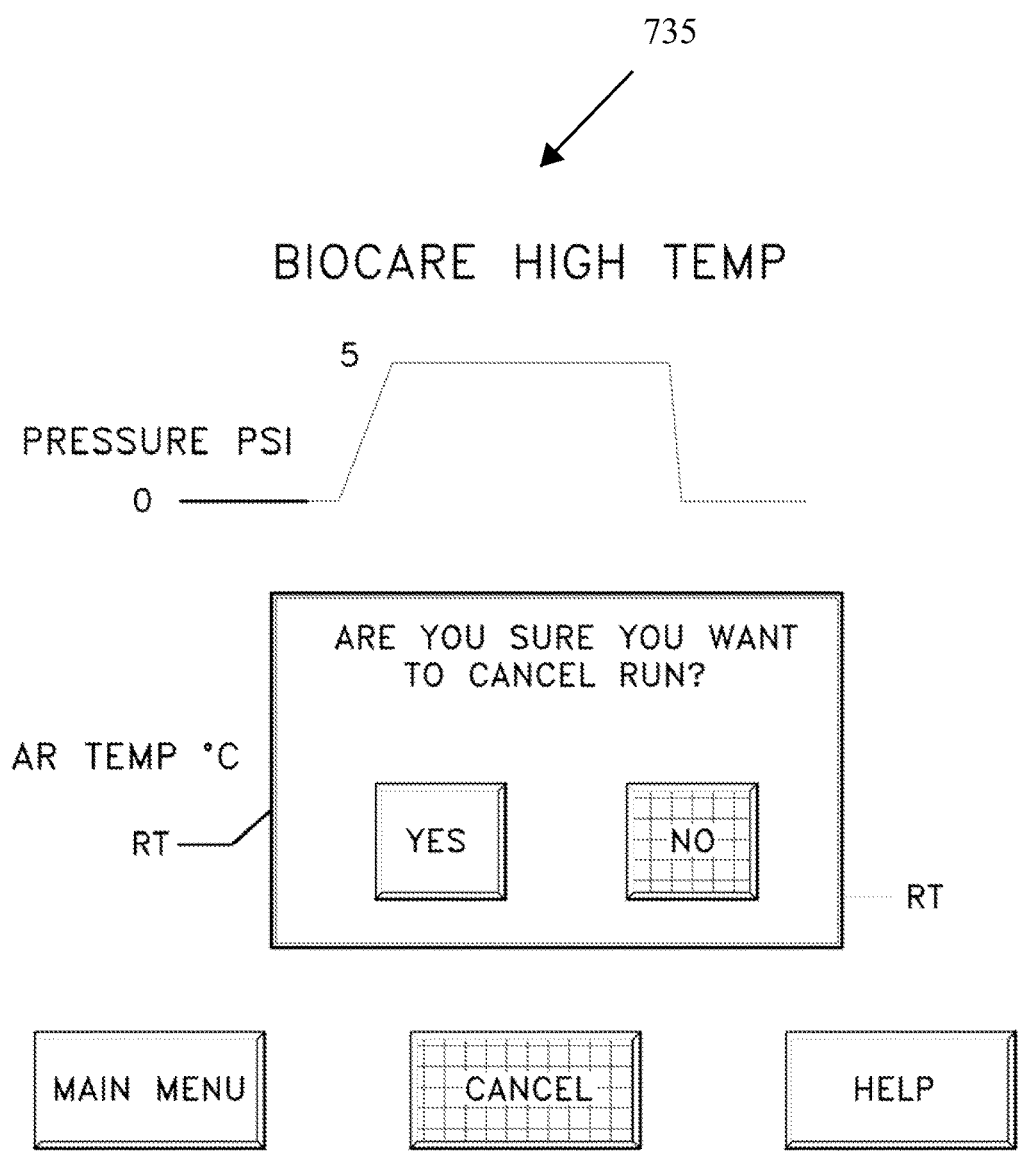
FIG. 52 is an example of an alternative alarm screen for a user interface system in accordance with embodiments of the present invention.
Figure 54:
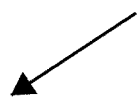
FIG. 54 is an example of a setup date/time screen for a user interface system in accordance with embodiments of the present invention.

FIG. 40 shows an example of a recommended protocol screen (723) giving options for selection of tissue type, antibody type, and antigen retrieval solution type as well as providing main menu and help options. FIG. 41 shows an example of a recommended protocol screen (724) where a user has selected prostate as a tissue type. FIG. 42 shows an example of a recommended protocol screen (725) where a user has selected a PIN 4 antibody type. FIG. 43 shows an example of a recommended protocol screen (726) where a user has selected a DIVA antigen retrieval solution type. FIG. 44 shows an example of a high temperature screen (727) where a graphic representation may provide tracking of the pressure during at least one processing run and where a graphic representation may provide tracking of a temperature during at least one processing run along with alarms may be displayed. Of course, any type of element or parameter can be displayed in a display tracker (803) including but not limited to time, temperature, pressure, alarm times, any combination thereof, and the like and may perhaps show the status of a program run or even a continuous status of a program run. Embodiments may provide remotely viewing the status of the program run via a remotely viewable display tracker such as with a remote device as discussed herein. A main menu, cancel, and/or help options may also be provided in the screen of FIG. 44. FIG. 45 shows an example of an alarm screen (728) providing options for a chime, voice, continuous, up and down, main menu, set, and help options. FIG. 46 shows an example of an alarm screen (729) where a chime alarm has been selected by a user. FIG. 47 shows an example of an alarm screen (730) where a voice alarm has been selected by a user. FIG. 48 shows an example of an alarm screen (731) where a chime alarm and a voice alarm have been selected by a user. FIG. 49 is an example of an intermediary screen (732) showing setup, run protocol, create protocol, return to run, and help options. FIG. 50 is an example of a high temperature screen (733) where a graphic representation may provide tracking of the pressure during at least one processing run and where a graphic representation may provide tracking of a temperature during at least one processing run along with alarms may be displayed. FIG. 51 shows an example of an alarm screen (734) where chime, once, voice, and the like options may be displayed for user selection. FIG. 52 shows an example of a cancel element as a cancel screen (735) during a processing run where a cancel selection has been made and the user has been prompted to make sure that they want to cancel the run. FIG. 53 shows an example of a new protocol screen (736) where a user may be prompted to enter a new protocol name and providing main menu, save, and help options. FIG. 54 shows an example of a setup date-time screen (737) providing options to: set the date format in US, EU, enter current time; set a time format in 12 hour, 24 hour, HH:MM:SS, MM:SS formats as well as main menu, set, and help options.

Embodiments of the present invention may provide a semi-automated biological specimen antigen retrieval pressure cooker device comprising a sealable heating pressure chamber (80); a heater (81) configured to heat an internal space of a sealable heating pressure chamber; an internal pressure sensor (407) of a sealable heating pressure chamber; a slide placement (424) located in a sealable heating pressure chamber configured to receive a plurality of slides each supporting a biological sample; a programmable process controller (100) of a sealable heating pressure chamber capable of receiving at least one user-selected protocol (709) for at least one program run (800); a starter element (801) of a programmable process controller to begin at least one program run in a sealable heating pressure chamber; and perhaps even a substantially user-disencumbering autonomous processing component of said plurality of slides each supporting said biological sample in said sealable heating pressure chamber. Methods may include semi-automatically retrieving antigens from biological specimens comprising the steps of: providing a plurality of slides each supporting a biological sample; providing a sealable heating pressure chamber capable of receiving a plurality of slides each supporting a biological sample; placing a plurality of slides each supporting a biological sample in a sealable heating pressure chamber; user-selecting process protocol on a programmable controller of a sealable heating pressure chamber to provide a selected protocol for at least one program run of a plurality of slides each supporting a biological sample; user-starting a selected protocol for at least one program run of a plurality of slides each supporting a biological sample in a sealable heating pressure chamber; substantially user-disencumbering autonomously processing a plurality of slides each supporting said biological sample after a step of user starting a selected protocol; heating a plurality of slides supporting a biological sample; sensing an internal pressure of a sealable heating pressure chamber; and perhaps even providing antigen retrieved biological samples supported on a plurality of slides.

Remarkably, in the past, pressure cooker type antigen retrieval devices may have required user monitoring of the device so that a user may have had to be near an antigen retrieval device during the processing run. Accordingly, the present invention provides, in embodiments, a substantially user-disencumbering autonomous processing component of biological samples supported by a plurality of slides in a sealable heating pressure chamber to provide substantially user-disencumbering autonomously processing of the biological samples on the slides. A system may provide user mobility during a program run such as while a set of slides with biological samples thereon are being processed to remove paraffin or perhaps for antigen retrieval. Thus, one example of a substantially user-disencumbering autonomous processing component may include a remotely monitoring processing component (106) of the slides perhaps to allow a user to remotely monitor the system while a system may autonomously process the samples. Systems may provide a variably responsive processing component to which a device may be capable of variably responsive processing or perhaps even variably automatically responsive processing of the slides perhaps with little to no input from a user. A system may be capable of sensing and reacting to certain element, variables, changes or the like.

Further walk away remote features may provide a remote device or even a remote timer which may provide locational freedom to a user so that the system doesn't have to be user monitored during a run. For example, FIG. 9 shows an embodiment of an operation of a remote device as discussed herein. A remote device may be a remote time, a remote alarm, a plurality of remote alarms, a remote error indicator, a remote card, any combination thereof, and the like. A remote card, a wireless alert, a text message, or the like may be used as an alarm or perhaps even some sort of remote access may be provided so that a user can be remotely aware of and even alerted during a run if needed. As experiments are conducted, embodiments of the present invention may provide thorough tracking of the system protocols, parameters, and the like. For example, many aspects and parameters of a antigen retrieval system such as but not limited to temperature, pressure, quantity, and the like may be tracked throughout the process and various reports may be available throughout or even after a system run. It may be desirable to track system operation for lab practices for CAP requirements and the like. A USB port may be provided to enable the laboratory to utilize flash drives to track and save run data. However, in embodiments, it may be desirable to provide a virus protected system.

In other embodiments, the present invention may provide smart error handling and perhaps even alarms responsive thereof in monitoring the system parameters of a heat induced antigen retrieval systems. For example, if a system is monitored correctly, it may detect, evaluate, and perhaps even correct any errors without compromising a run of the system and the like. In an embodiment, detection of low fluid levels within a system may be important so that the fluids can be refreshed before compromising the run. In addition, temperature detection perhaps with temperature probes, may allow precise device parameters to be adjusted during a run again so that the biological samples are not adversely affected. This can be done for any system parameter or protocol to provide efficient and effective antigen retrieval systems.

Thus, other non-limiting examples of a substantially user-disencumbering autonomous processing component may include a system which can provide at least one of the following features: automatically shutting off a sealable heating pressure chamber perhaps with an automatic shutoff; automatically controlling pressure in a sealable heating pressure chamber perhaps with an automatic pressure control; automatically controlling temperature a sealable heating pressure chamber perhaps with automatic temperature control; remotely user controlling a sealable heating pressure chamber perhaps with user-mobility input component; automatically smart system error handling a sealable heating pressure chamber perhaps with a smart system error handler, quality control processing a plurality of slides each supporting a biological sample perhaps with a quality control processing component; any combination thereof, and the like.

As discussed herein, a quality control processing component may, include but is not limited to, automatic recordation of an initial pH of a pH solution, automatic recordation of a post-run pH of pH solution, automatic recordation of temperature during a run, automatic recordation of pressure during a run, automatic recordation of tracked data during a run, any combination thereof, and the like.

As mentioned, embodiments of the present invention may include a heating device for heating biological specimens perhaps for antigen retrieval processing. A heating device may be an electric pressure cooker with a pressure gauge and a temperature sensor perhaps connected to a controller with a temperature display and a temperature alert. A controller may be arranged to heat a specimen at a selectable temperature for a selectable time period. A quality control process may include placing a heat sensitive pH indicating retrieval solution in a device and perhaps even placing a heat and pressure sensitive steam strip in the device. When a set temperature has been reached, the actual temperature and pressure may be recorded. When a device such as a cooker may be opened after heating, a pH indicating solution may be checked for color change that may indicate a pH change, and a steam strip may be checked for color change that may indicate that a predetermined temperature and perhaps even pressure levels have been reached.

In embodiments, the present invention may provide nonpareilly operating a sealable heating pressure chamber perhaps with a nonpareil operating element. A nonpareil operating element may be any kind of element or even operating function which may be unparalleled from past pressure chamber operations perhaps even from past pressure cookers used for antigen retrieval of biological samples. Nonpareil may be an individual component or it may be a combination of a plurality of components which provide nonpareil system operations. Nonpareil operation may include, but is not limited to, temperature sensing an internal liquid in a sealable heating pressure chamber perhaps with a internal liquid sensor (200); temperature sensing an actual liquid temperature of an internal liquid in a sealable heating pressure chamber; optimally locating a temperature sensor to provide an optimally located temperature sensor (423) in an internal liquid of a sealable heating pressure chamber. An optimal location of a temperature sensor may include substantially centering a temperature sensor in an internal liquid of a sealable heating pressure chamber. Alternatively a temperature sensor may be located away from a heat source of a sealable heating pressure chamber. A temperature sensor may include, but is not limited to, digital sensor, thermometer, automatic sensor, manual sensor, any combination thereof, and the like. At least one liquid such as but not limited to an antigen retrieval solution (61) may be provided in a sealable heating pressure chamber (80) or may even be provided in a slide container (88). Therefore, liquid may be an internal liquid. Liquid may include, but is not limited to, water, antigen-retrieval solution, pH solutions, solutions, any combination thereof, and the like.

Specifically, some embodiments of the present invention may provide a more accurate temperature measurement of the solution as contained in a device such as in a vessel, cooker, or the like. In the past, temperature within a heat induced antigen retrieval device may have only been measured at a surface level such as at the heat source like at the heating pad or the like. However, this type of measurement may not have accurately indicated the solution temperature or perhaps even may not have had an internal solution regulation of a system. Therefore, embodiments of the present invention may provide a solution temperature measurement element of which the actual solution or fluid temperature may be measured within a system. For example, this may be accomplished by placing a temperature sensor within the fluid or liquid of a vessel. The location of a temperature sensor or other type of temperature measurement element may be important within a solution in a vessel device. A temperature measurement within a solution that may be located near a heat element may not be as desirable as a location perhaps near a center of a solution or that may be some distance away from a heat element. The heat element may adversely affect a temperature reading within a solution if such measurement or sensor or the like is too close to the heat element. A temperature sensor may include but is not limited to a digital sensor, a thermometer, a manual sensor, and the like. In some embodiments, an internal temperature sensor may be displayed and the temperature even recorded onto some type of display system. As a non-limiting example, an internal temperature of a system may be regulated between about 90° C. to about 125° C.

Nonpareil operation of a sealable heating pressure chamber may include a rapid slide cooling element perhaps to provide rapidly cooling of a plurality of slides supporting a plurality of biological samples. Rapidly or even faster cooling may increase efficiency of a antigen retrieval process. For example, a rapid slide cooling element may include, but is not limited to, a fan (416), active cooling, refrigeration, a heat transfer element, any combination thereof, and the like.

Nonpareil operation of a sealable heating pressure chamber may include safety nonpareilly operating a sealable heating pressure chamber perhaps with a safety element such as but not limited to a lock (651), interlock, device lock, safety lock, lid lock, drain lock, combinations thereof, and the like. Alternatively, nonpareil operation of a sealable heating pressure chamber may include optimally protocol processing biological samples with an optimal processing protocol. As mentioned above, many different types of protocol may be used with an antigen retrieval system and may provide a user-selected protocol (804) perhaps selected from a protocol screen (709).

In some embodiments, it may be desirable to provide a low pressure heating system with perhaps immunohistochemistry heat retrieval procedures which may provide another example of nonpareil operation of a sealable heating pressure chamber. For example, a low pressure system may include a pressure which is less than about 7.5 psi. Therefore, a system can run at a much lower pressure while surprisingly achieving similar results as compared to higher pressure systems. Low pressure protocol may be provided as an option in a protocol screen (716) for processing of biological samples in a sealable heating pressure chamber. This may be achieved by accurate measurement of the internal fluid temperatures of the system. It may be important though to have accurate monitoring of the pressure and temperature to prevent over retrieving (such as heating too long or at too high a temperature) of biological specimens and the like.

Yet another example of nonpareilly operating a sealable heating pressure chamber may include a pressure range controller. In embodiments, an antigen retrieval process may have a controlled pressure range. As discussed herein, this may include providing a low pressure antigen retrieval system. If the pressure is limited to a certain range, then the temperature may be used as the dependent variable perhaps based on the pressure of the system. Thus, a pressure sensor may control a heat induced antigen retrieval process by perhaps limiting the heating operation so that the maximum allowed full operating pressure can be maintained.

Figure 55:
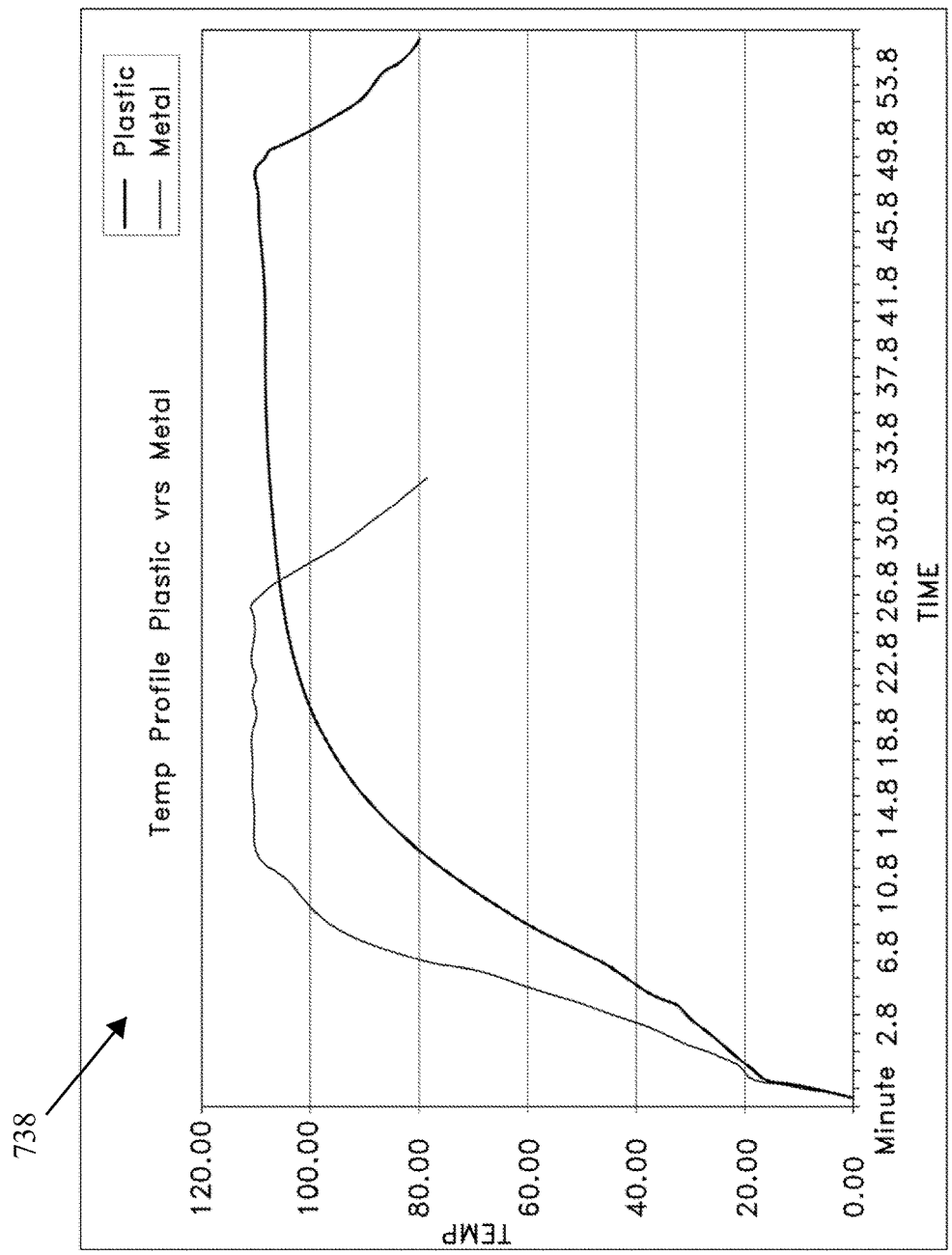
FIG. 55 is a graph of a temperature profile of plastic versus metal in accordance with embodiments of the present invention.

In embodiments, the present invention may provide quick, fast heating up and perhaps even cooling off of a biological specimen or the like in heat retrieval procedures perhaps as a nonpareilly operated system. Nonpareil operation of a system may thus include increasing thermal conductivity to said plurality of slides each supporting said biological sample perhaps with an increased thermal conductivity slide element. As one example, it may be desirable to use a slide holder (410) which may be a metal slide support, a metal slide container or perhaps even a metal tissue retrieval container which may allow heating and cooling at an increased rate. A metal component may increase thermal conductivity and therefore may have an increased heating or perhaps even a cooling process. Types of metal may include, but is not limited to, aluminum, gold, silver, platinum, palladium, stainless steel, any combination thereof, or the like. With a heat induced antigen retrieval systems, a biological specimen, perhaps on a slide, may be placed in a metal tissue retrieval container. The metal container and specimen may then be introduced into a sealable heating pressure chamber device which may apply a specified temperature and pressure control to expose or retrieve the biological specimens antigens for further processing. In an embodiment, a slide may be directly placed into a metal tissue retrieval container which may further increase heating and cooling and thus increase the sample processing. A holder or even a container may be a holder of a slide or may even be a container which may hold the process solution. An increase of thermal conductivity of a slide element may increase temperature efficiency by about 50% or higher perhaps when using metal holders or containers within antigen retrieval systems in comparison to plastic supports such as but not limited to a plastic tissue TEK container. As one example, FIG. 55 shows a temperature profile of plastic versus metal (738).

The present invention may provide a rapid slide heating element such as a recycling heating element which may be accomplished with an air circulating pump (209) or other systems for recycling heat in a sealable heating pressure chamber.

As mentioned above, a controller may be used to control processing of a biological specimen or the like. Embodiments of the present invention may provide automatically dynamically processing biological samples in a sealable heating pressure chamber perhaps with a dynamically responsive processor (31) perhaps with a computerized machine. By dynamically responsive, a processor may react to or even be receptive to a parameter, a sensed parameter, a change, a dynamic, or the like by constantly refreshing, continuously monitoring, or perhaps even ever-changing its system. A computer device may be connected to a sealable heating pressure chamber with an indirect connection, a direct connection, a wireless connection, a wired connection, or the like. A dynamically responsive processor may be a remotely dynamically responsive processor perhaps with a remote device as discussed herein. Remotely dynamic responsive processing may provide a efficient and perhaps even quick user response. Remotely dynamic responsive processing may provide responsiveness to an input or parameter from a remote processor such a remote computer, computerized machine and the like. A dynamically responsive processor may include recommending a protocol for a biological sample perhaps based on at least one user input. A user input may include, but is not limited to, type of sample, temperature, pressure, time, solution, selection of a pre-programmed protocol, selection of a recommended protocol, expert system for specific parameters, any combination thereof, and the like and as may be discussed herein.

A dynamically responsive processor may provide automatically adjusting an alarm for a processing run perhaps even during the processing run and perhaps even in response to a change in the processing run. For example, a smart error handler may be utilized for smart error handling processing, an automatic responsive alarm element may be utilized for creating an alarm based on at least one processing parameter, or even an automatic correction system may be used to automatically correct at least one processing parameter as discussed herein. A processing parameter may include, but is not limited to, a fluid level, a low fluid level, a completion time, a temperature, a maximum temperature, a pressure, a maximum pressure, a minimum temperature, a minimum pressure, a pH, a protocol, deparaffinization, antigen retrieval, any combination thereof, and the like. Another non-limiting example of a dynamically responsive processor may include a visual preview display perhaps based on at least one user-selected protocol so that a user may visually preview at least one processing run. This visual preview may be dynamically response by changing the preview or even the processing run visual graphics in response to a change in the processing run.

It may be desirable to provide faster heating methods and perhaps even better control of biological samples in the various systems as discussed herein. Use of feed forward, feedback, and perhaps even combinations thereof may be used in a control loop (904) in controlling a system and may even be provided in a dynamically responsive processing system (900). As shown conceptually in FIG. 56, a parameter sensor (901) may sense at least one parameter (902) and may automatically predictively adjust (in a feed forward sense) or may adjust (in a feedback sense) at least one processing run perhaps with a predictive program run adjuster or a program run adjuster (906) perhaps through a controller (905) and relay the adjustment to a system (907). When one or more output variables of a system may follow a parameter over time, a controller may manipulate inputs to a system to obtain the desired effect on the output of the system.

In a feedback sense, system control may be monitored and perhaps even adjusted for example by sensing a temperature, perhaps even an internal temperature, of a system during processing and adjusting at least one or multiple system parameters based on the sensed temperature. System parameters may include but are not limited to heat, pressure, time, pH, predictive time adjustment, a predictive temperature adjustment, a predictive pH adjustment and a predictive pressure adjustment, heat adjustment, a pressure adjustment, a time adjustment, a pH adjustment, and the like and may be based on any kind of sensed or tracked parameter. For example, a computer system or other processing system can take an internal temperature reading while specimens are processing and may calculate necessary adjustments to perhaps change the heat of the solution (e.g., if the heat is too high, the system will lower the heating temperature and vice versa). The parameter sensing and feedback thereof may also provide a feed forward type of prediction of how much more temperature or any other parameter such as how much time it will take to achieve a desired temperature or other result. For example, if a system knows what an internal solution temperature is, then it may calculate the next steps if the heat needs to be decreased or increased and perhaps even the time it will take for such adjustments. In embodiments, utilization of predictive algorithms may set current inputs of a specimen heating system for perhaps immunohistochemistry heat retrieval procedures.

Figure 56:
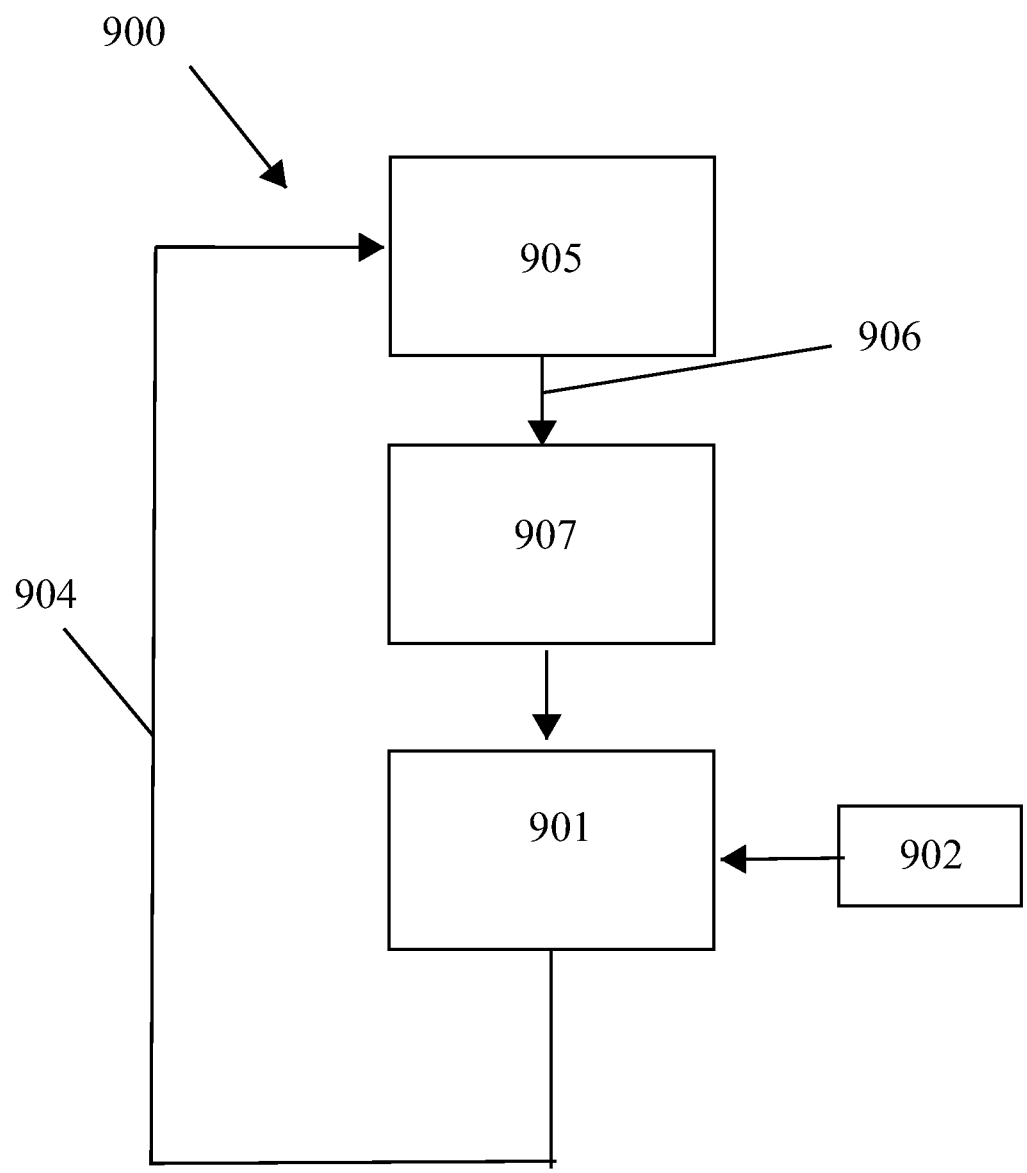
FIG. 56 is a conceptual representation of a control loop in accordance with embodiments of the present invention.

With respect to temperature sensing, embodiments of the present invention may provide dynamically responsive processing which may include automatically correcting a temperature of a pressure chamber perhaps with a temperature sensing correction element which may be understood from FIG. 56 at a conceptual level. A temperature probe may measure the temperature of an antigen retrieval solution perhaps even during operation or even processing of a specimen. For example, manual placement of a temperature sensor may be used with a heat induced antigen retrieval device. Alternatively, an auto sensor may be placed in any part of a container such as inside the solution containing element. The actual solution temperature (e.g. the internal temperature) may be assessed with a temperature sensor. As discussed above, it may be desirable to keep a sensor away from the heat supply or heat element of a system. Embodiments may also include a temperature correction system which may be used based on where a temperature sensor may be located perhaps providing a locational temperature sensor and calculating an actual temperature of a chamber. For example, if a temperature sensor were located near a heat supply, a temperature correction system may calculate a calculated internal solution temperature which may accurately reflect the internal solution temperature. A temperature correction system may even use two sensors within a heat induced antigen retrieval device so that an accurate internal solution temperature may be calculated, evaluated and perhaps even recorded. One sensor may be located at or near a heat source while another sensor may be located away from the heat source, perhaps at a non-heat source. Sensors may be located within or perhaps even outside of a solution and calculations thereof may be completed via a software system responsive to the sensor or sensors.

Examples of a heating device are discussed herein and may include a Decloaking Chamber, a Decloaker, a pressure cooker, a rice cooker, a heating device, and the like. A heating device may include, but is not limited to: a pressure chamber such as an internal chamber; a lid to cover and seal the pressure chamber; a sealing gasket that may seal the pressure chamber from pressure loss as well as the outer housing from incidental moisture; a display which may display pressure, temperature, time, protocol information, graphical display of real-time run progress, process error or system warning indicators (see software interface map), and the like; specimen containers which may hold a slide holder, slides (perhaps with biological samples), and even a pH indicating solution (e.g., antigen retrieval solution); a timer and data transfer device which may provide a remote indication of the time remaining in the operating cycle of the instrument and uploads all stored run data from the instrument and downloads same to a host computer for report generation and archiving; any permutation or combination of the above; and the like.

In embodiments, the present invention may provide a gravity flow drain tube to assist in the drainage of solutions that may be in a vessel. An automatic shutoff operation may be tied in with a gravity flow drain tube so that if solutions are being removed from a vessel, the device may be turned off. It may also be desirable to provide a safety interlock to prevent operation of an antigen retrieval system perhaps while a drain tube is being installed or perhaps even during drainage use. For example, a drain tube may be any kind of tubing connected to a device or vessel allowing removal of liquids into a separate container or otherwise disposed.

In embodiments, heat induced antigen retrieval systems may be configured to receive multiple biological samples on slides or may even be capable of receiving one or even just a few biological samples. For example, a decloaker system may be made to accept several slides with biological specimens thereon or alternatively, a smaller system may be made for processing of just one or even two slides. As an example, an instrument may be designed as a mini-Decloaker or perhaps a "Mini D" which may be a single slide, sealed chamber intended for Heat Induced Epitope Retrieval, HIER, perhaps using heat above 100° C. to create pressure. It may also be intended for deparaffinization of the slides at temperatures between about 60 and about 100° C. Two paired slides may be heated from a common thermal source. A common supply may be used to fill and empty individual chambers with AR and perhaps even wash solutions. The temperature could be maintained in the "Mini D" from about 25° C. to about 110° C. with pressures up to about 7 psi. The deparaffinization and HEIR processes may be greatly reduced in time to completion perhaps using this device and even proprietary solutions.

The pH indicating retrieval solution may be arranged to change color at a predetermined temperature range to indicate pH change. Examples of pH indicating retrieval solutions may include those sold under the trademarks "REVEAL" and "BORGDECLOAKER" by BioCare Medical of California. The "REVEAL" retrieval solution may be arranged to change from a yellow color at room temperature and a pH of 6.0 to an orange color at between about 80-125° C. to indicate a pH range of about 6.4 to 6.5. The "BORGDECLOAKER" retrieval solution may be arranged to change from perhaps a light purple color at room temperature at a pH of about 9.5 to a gray color at between about 80-125° C. to indicate a pH range of about 8.4 to 8.6. Since the pH of the pH indicating retrieval solution may change at an elevated temperature range of 80-125° C., the color change may represent a corresponding pH change. The pH ranges of the "REVEAL" and "BORGDECLOAKER" retrieval solutions may be narrow enough for accuracy.

In embodiments, a special protocol timing or even solution may be provided to speed up processing and even protocol. A variety of heat retrieval (HIER) solutions may be used as retrieval buffers including but not limited to citrate buffer, EDTA, Tris buffer, and the like. Retrieval buffers may also be used in combination with a light enzyme digestion to perhaps obtain optimal pretreatment and IHC staining results. A combination of digestion and heat retrieval may be particularly effective for certain antibodies in over-fixed tissue. These combinations may be specific for each antibody and may be clone-dependent. For optimal staining, different procedure modifications may be used for different antibody-antigen combinations. If tissues are properly fixed, optimization of antibody titers and perhaps even overnight incubation such as at about 4° C., may provide optimum results with perhaps citrate or a Tris buffer type retrieval buffer.

In embodiments, it was found that about 30 to about 60 minutes of steam may be equivalent to about 10 to about 20 minutes of microwaving, or may even be equivalent to about 5 to about 10 minutes of using a pressure cooker. A pressure cooker retrieval method minute for minute may be more effective than steam or microwaving. Low temperature retrieval methods may include incubation at about 75 to about 80° C. for approximately between about 12 to about 16 hours. In embodiments, low temperature retrieval methods that may work well with those tissues that have a tendency to fall off the slide such as to but not limited to brain, bone, cartilage and the like. Morphology may also be adapted perhaps with steam heat at a temperature of approximately 95° C. and perhaps even steaming for between about 45 to about 60 minutes. A pressure cooker temperature may be about 120° C. and may be fast and convenient. Because a solution is under pressure, it may not boil; hence it may provide less tissue loss. In embodiments, pressure cooker methods may provide a walk-away method and can be used with different slide containers and holders. It may be important to adjust a pressure cooker method based on heat artifacts and tissues in some embodiments. Pressure cooker methods may also be used with low temperature methods as mentioned above. Low temperature methods may be gentle and may yield good morphology. Low temperature methods may require longer process time and may be slower than others. Nonpareil operations may thus include an increased process run to which at least one process run may be efficiently processed. For example, a process run may take about 35 minutes.

Another example of nonpareilly operating a sealable heating pressure chamber may include quality control processing said plurality of slides each supporting a biological sample perhaps with a quality control element. A non-limiting example of a quality control element may include a pH indicator, such as a pH strip (62), that may be modified so that it may be color coded for each type of buffer used. These indicators may allow for monitoring the pH and may even aid in quality control during retrieval procedures. As discussed herein, embodiments may also include a steam monitor strip for use with a pressure cooker system. For example, if a monitor strip turns a charcoal gray-black that may indicate the proper heat and pressure was obtained.

Specific enzyme procedures for digestion for various antibodies may be included in various embodiments. For example, trypsin may be desired for retrieval of keratin AE1/AE3. Another example may include a high molecular weight cytokeratin antibody which may be used for basal cells and prostate biopsies. With this antibody, embodiments may include use of a high Tris pH buffer retrieval solution perhaps followed by a one minute digestion to achieve optimal staining and perhaps even without regard to a fixation time.

If a non-pH indicating retrieval solution may be used, for example, because of user preference, a pH strip may be placed in the retrieval solution. A step may be skipped if the non-pH indicating retrieval solution may be used. As a backup and to provide redundancy for reliability, the pH strip may also be placed in a pH indicating retrieval solution.

In a conventional pH strip system, a color chart calibrated for room temperature testing may be provided. However, heating a pH strip may turn it darker than at room temperature for the same pH change. If the pH strip in the cooker is matched with a conventional color chart after heating, the chart may indicate a higher pH, when the actual pH may be lower. Since the color change of the pH strip may be different at elevated temperatures than at room temperature, a heat adjusted color chart may be provided. The heat adjusted color chart may have a color range which may be darkened to compensate for the darkening effect of the heat, and may thus be arranged to accurately measure pH at between about 80 and about 125° C. in embodiments of the present heating process.

If the pH strip may be used instead or concurrently, it may be compared to the heat adjusted color chart to read and record the actual pH reached. The pH strip can also be used with other types of retrieval solutions, whether home-brewed or commercial solutions, which do not change color at elevated temperatures. The actual pH may be tracked, monitored, and even recorded to fulfill the pH recording requirement of governing body regulations.

The heat and pressure sensitive steam strip may also be checked for the proper color change which may indicate that a predetermined temperature and pressure have been adequately reached. This may backs up the reading of the digital temperature display and the pressure gauge for reliability and accuracy.

Accordingly, in various embodiments, the present heating device may be arranged to heat biological specimens to a selectable temperature. It may heat the specimens under pressure. It may activate an alert when the set temperature has been reached to perhaps notify the user to record the actual temperature for quality control as required by laboratory governing body operating standards. It may automatically adjust the total heating time to compensate for different amounts of materials. It may enable recording of the actual pressure inside the cooker for quality control. It may enable a recording of the pH of the specimens perhaps at the set temperature for quality control. It may accurately indicate the pH of the specimens perhaps at the set temperature. It may provide redundancy in pH indication, temperature indication, and pressure indication for reliability. It may also increase safety.

As discussed, an antigen retrieval system, in embodiments, may include software to operate and perhaps even control the system. As an example, factory preprogrammed protocols or even recommended protocols may be included in the software operating system. As mentioned herein, embodiments may provide an expert system approach to which a computer system can associate a particular tissue or antibody or the like with a retrieval solution database. As shown in FIGS. 45-48, embodiments of the invention may provide user selectable alarms perhaps through sounds, beeps, chimes, voice, volume or the like. In other embodiments, the present invention may provide a visual preview of a protocol such as that shown as an example in FIG. 50. The present invention may then provide a graphical interface or similar type of visual display of how the system protocols and parameters may operate. A user may then get a visual of the projected run of the biological sample process, such as a visual of how the temperature will be adjusted, how the temperature will be adjusted, any projected alarms, and perhaps even the timeframe thereof. A graphical interface may also represent the projected system parameters. Software systems of the present invention may also include a foolproof checklist to perhaps avoid user errors such as not proceeding with the process until certain steps are completed and the like. This may include checking the temperature, checking the fluid flow, loading containers, and the like.

In alternative embodiments, an antigen retrieval system may relate to temperature aspects including but not limited to temperature controller limits, a heater element over temperature thermal fuse, cool touch housing, indirect steam vent, temperature signal feedback sensing cutout, and the like. Pressure aspects may include but are not limited to pressure controller limits, pressure relief valves, pressure release valve (bleed), and the like. Electrical aspects may include power fuses, double isolation high-voltage insulation, on-board over current fuse, ground-fault interrupt circuitry, conformal coating of PCBs, update timer shutdown circuit (perhaps if the system is not updated continuously as in the case of a failure in the computer/controller, the system shuts down), door open and door locked sensors and the like. The mechanical aspects may include a lid lock perhaps for use during operation and even during a power failure, a drain lock to perhaps prevent operation of a system when draining or even a drain hose and the like.

As can be easily understood from the foregoing, the basic concepts of the present invention may be embodied in a variety of ways. It involves both biological specimen heating techniques as well as devices to accomplish the appropriate heating device. In this application, the biological specimen heating techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims that will be included in any subsequent patent application.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure and may be relied upon when drafting the claims for any subsequent patent application. It should be understood that such language changes and broader or more detailed claiming may be accomplished at a later date (such as by any required deadline) or in the event the applicant subsequently seeks a patent filing based on this filing. With this understanding, the reader should be aware that this disclosure is to be understood to support any subsequently filed patent application that may seek examination of as broad a base of claims as deemed within the applicant's right and may be designed to yield a patent covering numerous aspects of the invention both independently and as an overall system.

Further, each of the various elements of the invention and claims may also be achieved in a variety of manners. Additionally, when used or implied, an element is to be understood as encompassing individual as well as plural structures that may or may not be physically connected. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "heater" should be understood to encompass disclosure of the act of "heating"—whether explicitly discussed or not— and, conversely, were there effectively disclosure of the act of "heating", such a disclosure should be understood to encompass disclosure of a "heater" and even a "means for heating." Such changes and alternative terms are to be understood to be explicitly included in the description. Further, each such means (whether explicitly so described or not) should be understood as encompassing all elements that can perform the given function, and all descriptions of elements that perform a described function should be understood as a non-limiting example of means for performing that function.

Any patents, publications, or other references mentioned in this application for patent are hereby incorporated by reference. Any priority case(s) claimed by this application is hereby appended and hereby incorporated by reference. In addition, as to each term used it should be understood that unless its utilization in this application is inconsistent with a broadly supporting interpretation, common dictionary definitions should be understood as incorporated for each term and all definitions, alternative terms, and synonyms such as contained in the Random House Webster's Unabridged Dictionary, second edition are hereby incorporated by reference. Finally, all references listed in any information disclosure statement or other information statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

Thus, the applicant(s) should be understood to have support to claim and make a statement of invention to at least: i) each of the heating devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) each system, method, and element shown or described as now applied to any specific field or devices mentioned, x) methods and apparatuses substantially as described hereinbefore and with reference to any of the accompanying examples, xi) an apparatus for performing the methods described herein comprising means for performing the steps, xii) the various combinations and permutations of each of the elements disclosed, xiii) each potentially dependent claim or concept as a dependency on each and every one of the independent claims or concepts presented, and xiv) all inventions described herein.

In addition and as to computer or machine aspects and each aspect amenable to programming or other electronic automation, the applicant(s) should be understood to have support to claim and make a statement of invention to at least: xv) processes performed with the aid of or on a computer or machine as described throughout the above discussion, xvi) a programmable apparatus as described throughout the above discussion, xvii) a computer readable memory encoded with data to direct a computer comprising means or elements which function as described throughout the above discussion, xviii) a computer configured as herein disclosed and described, xix) individual or combined subroutines and programs as herein disclosed and described, xx) a carrier medium carrying computer readable code for control of a computer to carry out separately each and every individual and combined method described herein or in any claim, xxi) a computer program to perform separately each and every individual and combined method disclosed, xxii) a computer program containing all and each combination of means for performing each and every individual and combined step disclosed, xxiii) a storage medium storing each computer program disclosed, xxiv) a signal carrying a computer program disclosed, xxv) the related methods disclosed and described, xxvi) similar, equivalent, and even implicit variations of each of these systems and methods, xxvii) those alternative designs which accomplish each of the functions shown as are disclosed and described, xxviii) those alternative designs and methods which accomplish each of the functions shown as are implicit to accomplish that which is disclosed and described, xxix) each feature, component, and step shown as separate and independent inventions, and xxx) the various combinations and permutations of each of the above.

With regard to claims whether now or later presented for examination, it should be understood that for practical reasons and so as to avoid great expansion of the examination burden, the applicant may at any time present only initial claims or perhaps only initial claims with only initial dependencies. The office and any third persons interested in potential scope of this or subsequent applications should understand that broader claims may be presented at a later date in this case, in a case claiming the benefit of this case, or in any continuation in spite of any preliminary amendments, other amendments, claim language, or arguments presented, thus throughout the pendency of any case there is no intention to disclaim or surrender any potential subject matter. It should be understood that if or when broader claims are presented, such may require that any relevant prior art that may have been considered at any prior time may need to be re-visited since it is possible that to the extent any amendments, claim language, or arguments presented in this or any subsequent application are considered as made to avoid such prior art, such reasons may be eliminated by later presented claims or the like. Both the examiner and any person otherwise interested in existing or later potential coverage, or considering if there has at any time been any possibility of an indication of disclaimer or surrender of potential coverage, should be aware that no such surrender or disclaimer is ever intended or ever exists in this or any subsequent application. Limitations such as arose in *Hakim v. Cannon Avent Group, PLC,* 479 F.3d 1313 (Fed. Cir 2007), or the like are expressly not intended in this or any subsequent related matter. In addition, support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. In drafting any claims at any time whether in this application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible. The use of the phrase, "or any other claim" is used to provide support for any claim to be dependent on any other claim, such as another dependent claim, another independent claim, a previously listed claim, a subsequently listed claim, and the like. As one clarifying example, if a claim were dependent "on claim 20 or any other claim" or the like, it could be re-drafted as dependent on claim 1, claim 15, or even claim 25 (if such were to exist) if desired and still fall with the disclosure. It should be understood that this phrase also provides support for any combination of elements in the claims and even incorporates any desired proper antecedent basis for certain claim combinations such as with combinations of method, apparatus, process, and the like claims.

Finally, any claims set forth at any time are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

We claim:

1. A method for semi-automatically retrieving antigens from biological specimens comprising the steps of:
   providing a plurality of slides each supporting a biological sample;
   providing a sealable heating pressure chamber capable of receiving said plurality of slides each supporting said biological sample;
   placing said plurality of slides each supporting said biological sample in a multi-slide container;
   adding at least one antigen retrieval solution to said multi-slide container containing said plurality of slides each supporting said biological sample;
   placing said multi-slide container containing said plurality of slides each supporting said biological sample into said sealable heating pressure chamber;
   displaying options on a user interface of a programmable controller of said sealable heating pressure chamber, wherein said options comprise a pre-programmed protocol and a create new protocol;
   user selecting said pre-programmed protocol or user creating said new protocol on said user interface of said programmable controller of said sealable heating pressure chamber to provide a selected protocol for at least one program run of said plurality of slides each supporting said biological sample, wherein said selected protocol is based on said user selected pre-programmed protocol or said user created new protocol;
   user-starting said selected protocol for said at least one program run of said plurality of slides each supporting said biological sample in said sealable heating pressure chamber;
   automatically displaying a run status of said selected protocol;
   automatically processing said biological samples on each of said plurality of slides after said step of user starting said selected protocol;
   automatically heating said plurality of slides each supporting said biological sample;
   automatically sensing an internal pressure of said sealable heating pressure chamber;
   automatically recording an internal chamber temperature and said internal pressure at various times during said at least one program run; and
   providing antigen retrieved biological samples supported on said plurality of slides.

2. A method for semi-automatically retrieving antigens from biological specimens according to claim 1 further comprising the step of generating a run report for said at least one program run.

3. A method for semi-automatically retrieving antigens from biological specimens according to claim 1 and further comprising the step of remotely monitoring said processing of said biological samples with a remote device.

4. A method for semi-automatically retrieving antigens from biological specimens according to claim 1 wherein said step of automatically processing said biological samples on each of said plurality of slides comprises a step selected from a group consisting of: automatically shutting off said sealable heating pressure chamber, automatically controlling pressure in said sealable heating pressure chamber, automatically controlling temperature said sealable heating pressure chamber, remotely user controlling said sealable heating pressure chamber; automatically smart system error handling said sealable heating pressure chamber, and any combination thereof.

5. A method for semi-automatically retrieving antigens from biological specimens according to claim 1 further comprising the step of increasing thermal conductivity to said plurality of slides each supporting said biological sample.

6. A method for semi-automatically retrieving antigens from biological specimens according to claim 5 wherein said step of increasing thermal conductivity to said plurality of slides each supporting said biological sample comprises the step of providing metal slide supports for said plurality of slides each supporting said biological sample.

7. A method for semi-automatically retrieving antigens from biological specimens according to claim 1 and further comprising a step of user-selecting a process protocol wherein said process protocol is selected from a group consisting of pre-heating protocol, a temperature setting, pressure setting, a pre-programmed protocol, a newly created protocol, an alarm protocol, a tissue type, an antibody type, an antigen retrieval solution, a ramp, a soak, a high temperature protocol, a low temperature protocol, a pre-start checklist, a delay start time, and any combination thereof.

8. A method for semi-automatically retrieving antigens from biological specimens according to claim 1 wherein said biological sample is selected from a group consisting of an embedded biological sample, a biological tissue sample, a biological fixed sample, a formalin-fixed sample, and a paraffin embedded biological tissue sample.

9. A method for semi-automatically retrieving antigens from biological specimens according to claim 1 wherein said user interface comprises elements selected from the group consisting of a task bar, system setup, set alarm, a run protocol, an expert system, export reports, pretest checklist, run completed, run canceled, login screen, welcome, protocol manager, login control, export in process, user manager, change protocol, confirm delete, create new protocol, create new antibody, create new user, preheat settings, and any combination thereof.

10. A method for semi-automatically retrieving antigens from biological specimens according to claim 1 and further comprising the step of circulating air with an air circulating pump in said sealable heating pressure chamber.

11. A method for semi-automatically retrieving antigens from biological specimens according to claim 1 wherein said step of automatically processing said biological samples on each of said plurality of slides after said step of user starting said selected protocol comprises the step of automatically correcting at least one processing parameter during said program run.

12. A method for semi-automatically retrieving antigens from biological specimens according to claim 1 wherein said step of automatically processing said biological samples on each of said plurality of slides after said step of user starting said selected protocol comprises feedback processing said plurality of slides each supporting said biological sample in said sealable heating pressure chamber.

13. A method for semi-automatically retrieving antigens from biological specimens according to claim 1 wherein said step of automatically processing said biological samples on each of said plurality of slides after said step of user starting said selected protocol comprises feed forward processing said plurality of slides each supporting said biological sample in said sealable heating pressure chamber.

14. A method for semi-automatically retrieving antigens from biological specimens according to claim 1 wherein said step of automatically processing said biological samples on each of said plurality of slides after said step of user starting said selected protocol comprises automatically predictively adjusting said at least one program run.

15. A method for semi-automatically retrieving antigens from biological specimens according to claim 14 wherein said step of automatically predictively adjusting at least one program run comprises selecting a predictive adjustment from a group consisting of a predictive time adjustment, a predictive temperature adjustment, a predictive pH adjustment and a predictive pressure adjustment.

* * * * *